United States Patent
Casal Álvarez et al.

(10) Patent No.: US 10,829,560 B2
(45) Date of Patent: Nov. 10, 2020

(54) AGENTS BINDING SPECIFICALLY TO HUMAN CADHERIN-17, HUMAN CADHERIN-5, HUMAN CADHERIN-6 AND HUMAN CADHERIN-20 RGD MOTIF

(71) Applicant: CONSEJO SUPERIOR DE INVESTIGACIONES CIENTÍFICAS, Madrid (ES)

(72) Inventors: José Ignacio Casal Álvarez, Madrid (ES); Rubén Álvaro Bartolome Conde, Madrid (ES)

(73) Assignee: CONSEJO SUPERIOR DE INVESTIGACIONES CIENTIFICAS, Madrid (ES)

( * ) Notice: Subject to any disclaimer, the term of this patent is extended or adjusted under 35 U.S.C. 154(b) by 0 days.

(21) Appl. No.: 15/565,937

(22) PCT Filed: Apr. 20, 2015

(86) PCT No.: PCT/EP2015/058527
§ 371 (c)(1),
(2) Date: Oct. 12, 2017

(87) PCT Pub. No.: WO2016/169581
PCT Pub. Date: Oct. 27, 2016

(65) Prior Publication Data
US 2019/0048090 A1 Feb. 14, 2019

(51) Int. Cl.
| | |
|---|---|
| C07K 16/30 | (2006.01) |
| A61P 35/00 | (2006.01) |
| C12N 15/62 | (2006.01) |
| C07K 16/28 | (2006.01) |
| G01N 33/574 | (2006.01) |
| C12N 5/12 | (2006.01) |
| C12N 15/85 | (2006.01) |

(52) U.S. Cl.
CPC .......... *C07K 16/2896* (2013.01); *A61P 35/00* (2018.01); *C07K 16/30* (2013.01); *C12N 5/12* (2013.01); *C12N 15/62* (2013.01); *G01N 33/57484* (2013.01); *C07K 2317/33* (2013.01); *C07K 2317/34* (2013.01); *C07K 2317/55* (2013.01); *C07K 2317/56* (2013.01); *C07K 2317/76* (2013.01); *C07K 2317/92* (2013.01); *C12N 2015/8518* (2013.01); *G01N 33/57438* (2013.01); *G01N 33/57446* (2013.01)

(58) Field of Classification Search
CPC ..... C07K 16/2896; C07K 16/30; A61P 35/00; C12N 5/12; C12N 15/62
USPC .................................................. 424/133.1
See application file for complete search history.

(56) References Cited

U.S. PATENT DOCUMENTS

2012/0114672 A1* 5/2012 Rohlff .................... C07K 16/28
424/174.1

FOREIGN PATENT DOCUMENTS

| JP | 2012523848 | | 10/2012 |
|---|---|---|---|
| JP | 2013505702 | A | 2/2013 |
| JP | 2014530019 | | 11/2014 |
| WO | 03038096 | A1 | 8/2003 |
| WO | 2005110039 | A2 | 11/2005 |
| WO | 2011037271 | A1 | 3/2011 |
| WO | 2013055101 | A1 | 4/2013 |

OTHER PUBLICATIONS

Almagro & Fransson, Frontiers in Bioscience 2008; 13:1619-33.*
De Genst et al., Dev Comp Immunol 2006; 30:187-98.*
Yoshinaga et al., J. Biochem 2008; 143: 593-601.*
Wang, et al., Anti-Cadherin-17 antibody Modulates Beta-Catenin Signaling and Tumorigenicity of Hepatocellular Carcinoma, PLOS One, Sep. 2013, vol. 8, Issue (e72386).
Lin, et al., Targeting Cadherin-17 Inactivates Ras/Raf/MEK/ERK Signaling and Inhibits Cell proliferation in Gastric Cancer, PLOS One, Jan. 2014, vol. 9, Issue 1, e85296.
Cuesta, et al., Multivalent Antibodies: When Design Surpasses Evolution, Trends in Biotechnology 28 (2010) 355-362.
Cole, et al., The Jpred 3 Secondary Structure Prediction Server, Nucleic Acids Research, 2008, vol. 36, W197-W201.
Bartolome, et al., An RGD Motif Present in Cadherin 17 Induces Integrin Activation and Tumor Growth, Journal of Biological Chemistry, Dec. 12, 2014, vol. 289, No. 50, pp. 34801-34814.
Bartolome et al., Cadherin-17 interacts with a2b1 integrin to regulate cell proliferation and adhesion in colorectal cancer cells causing liver metastasis, Oncogene (2013), 1-12.
James W. Stave and Klaus Lindpaintner, Antibody and Antigen Contact Residues Define Epitope and Paratope Size and Structure, The Journal of Immunlogy, Published Jun. 24, 2013, doi:10.4049/jimmunol.1203198.
Ruben A. Bartolome, et al., Monoclonal Antibodies Directed against Cadherin RGD Exhibit Therapeutic Activity against Melanoma and Colorectal Cancer Metastasis, Clinical Cancer Research, Published Online First Sep. 15, 2017; DOI: 10:1158/1078-0432, CCR-17-14444.

* cited by examiner

*Primary Examiner* — Yan Xiao
(74) *Attorney, Agent, or Firm* — Caesar Rivise, PC

(57) ABSTRACT

The disclosure relates to agents binding specifically to human cadherin 17 (CDH17), and/or to human cadherin 5 (CDH5), and/or to human cadherin 6 (CDH6), and/or to human cadherin 20 (CDH20). The disclosure also relates to the use of these agents in therapy, methods for diagnosis and/or prognosis and/or stratification of a cancer in a subject, and pharmaceutical compositions comprising said agents. The disclosure also relates to cancer markers and markers of metastasis.

9 Claims, 22 Drawing Sheets

Specification includes a Sequence Listing.

AGENTS BINDING SPECIFICALLY TO HUMAN CADHERIN-17, HUMAN CADHERIN-5, HUMAN CADHERIN-6 AND HUMAN CADHERIN-20 RGD MOTIF

FIELD OF THE INVENTION

The present invention relates to the field of cancer therapies. In particular, the invention relates to agents binding specifically to human cadherin-17, human cadherin-5, human cadherin-6 and/or human cadherin-20 as well as to methods and uses of said agents.

BACKGROUND OF THE INVENTION

Cadherin 17 (CDH17), also known as liver-intestine cadherin (LI-cadherin), is a non-canonical, 7D-domain cadherin. Its sequence is formed by 7 extracellular domains and a very short cytoplasmic domain. CDH17 is present in foetal liver and gastrointestinal tract, exhibiting elevated expression during embryogenesis. The gene is silenced in adult healthy liver and gut. However, CDH17 is expressed again in gastric cancer, oesophagus carcinoma, pancreatic cancer and hepatocarcinoma. In primary colon cancer tumours, poorly-differentiated tumours, as well as in lymph nodes, CDH17 is expressed at low levels.

More than 90% of tumour samples from colorectal cancer patients show expression of cadherin-17 (CDH17). There is a significant association between high expression of CDH17 with liver metastasis and poor survival of the patients. CDH17 expression is increased in patients with metastasis and correlated with poor prognosis, suggesting an association between CDH17 expression and final hepatic colonization during late stages of metastasis.

CDH17 expression was increased in highly-metastatic KM12SM colon cancer cells. An exhaustive proteomic analysis of cell membrane proteins in these cells detected only 5 integrin subunits: $\alpha 2$, $\alpha 6$, $\alpha v$, $\beta 1$ and $\beta 4$. No expression of other integrins in epithelial colon cancer cells has been described, except some $\beta 6$ integrin constructs. CDH17 was part of a large protein complex containing, among other proteins, $\alpha 2\beta 1$ and $\alpha 6\beta 4$ integrins in colorectal cancer cells. Although $\alpha 6\beta 4$ integrin was present in the complex, only the interaction with $\alpha 2\beta 1$ triggered the integrin signalling pathway and caused the activation of the focal adhesion kinase (FAK), Ras, ERK1/2 and cyclin D1 to increase cell adhesion and proliferation. It has been described that $\alpha 2$ integrin mediates collagen type IV-dependent activation of focal adhesion kinase (FAK) and mediates selective liver metastasis.

Lin et al. (2014, PLoS One 9:e85296) described that the knockdown of CDH17 inhibited cell proliferation, migration, adhesion and colony formation, and also induced a cell cycle arrest and apoptosis in AGS human GC cells. Their results demonstrated the capacity of CDH17 to regulate the activity of Ras/Raf/MEK/ERK pathway for cell proliferation in GC, and suggest that CDH17 can serve as an attractive therapeutic target for future research.

Wang et al. (2014, PLoS One 8:e72386) investigated the therapeutic potential of a monoclonal antibody (Lic5) that targets the CDH17 antigen in HCC. In vitro experiments showed Lic5 could markedly reduce CDH17 expression in a dose-dependent manner, suppress $\beta$-catenin signalling, and induce cleavages of apoptotic enzymes caspase-8 and -9 in HCC cells. Treatment of animals in subcutaneous HCC xenograft model similarly demonstrated significant tumour growth inhibition using Lic5 antibody alone, or in combination with conventional chemotherapy regimen.

Given the limited amount of targeted therapies for CDH17-expressing tumours, there is still a need in the art to provide agents specifically recognising CDH17 that are suitable for the diagnosis, prognosis and/or treatment of a cancer concomitant with cells expressing CDH17.

BRIEF DESCRIPTION OF THE INVENTION

The authors of the present invention have found that the human 7D-cadherin, CDH17, contains an RGD site with capacity to act as a new ligand for integrin binding. This conclusion was obtained from the following observations: i) interaction of CDH17 with $\alpha 2\beta 1$ integrin required the presence of the RGD binding site (Example 2), ii) the capacity of the RGD motif to specifically bind $\alpha 2\beta 1$ integrin in colon cancer cells was supported by different binding and cell adhesion assays including siRNA experiments (Example 3), iii) CDH17-RGD ectodomain was able to bind colon cancer cells and activate $\beta 1$ integrin when added exogenously (Example 3), and iv) after in vivo inoculation, tumour cells expressing mutant CDH17 RAD showed a considerable delay in tumour growth and liver colonization (Example 6). In summary, RGD works as a switch that regulates the integrin activation in colon cancer metastatic cells. Additionally the inventors have generated a series of agents that bind specifically to the RGD motif of CDH17, as well as peptides that compete with CDH17 for the interaction with $\alpha 2\beta 1$ integrin. They have also observed that there are also RGD motifs in other cadherins, such as CDH5 and CDH6, and based on this observation they have also generated agents that bind specifically to the RGD motifs in these cadherins.

Thus, in an aspect, the invention relates to an agent binding specifically to an epitope comprising residues 603 to 605 of human cadherin 17 (CDH17), and/or to an epitope comprising residues 236 to 238 or residues 299 to 301 of human cadherin 5 (CDH5), and/or to an epitope comprising residues 83 to 85 of human cadherin 6 (CDH6), and/or to an epitope comprising residues 89 to 91 of human cadherin 20 (CDH20), wherein said agent is an immunoglobulin agent or a non-immunoglobulin agent selected from the group consisting of a peptide aptamer, a nucleic acid aptamer, a DARPin, an affibody, and an anticalin.

In another aspect, the invention relates to an antibody construct comprising the antigen-binding fragment according to the invention, wherein the antibody construct is selected from the group consisting of scFv, scFv-Fc, minibody, (scFv)2 and diabody.

In another aspect, the invention relates to a nucleic acid selected form the group consisting of:
a) a nucleic acid encoding the agent according to the invention or the antibody construct according to the invention, and
b) a complementary nucleic acid of a nucleic acid as defined in a).

In another aspect, the invention relates to an expression cassette comprising the nucleic acid according to the invention.

In another aspect, the invention relates to a vector comprising the nucleic acid or the expression cassette according to the invention.

In another aspect, the invention relates to a cell comprising the nucleic acid according to the invention, or the expression cassette according to the invention, or the vector according to the invention.

In another aspect, the invention relates to the hybridoma cell line with reference PA383-25.4.1, deposited under Accession number DSM ACC3266 on 9 Apr. 2015 at the Leibniz-Institut DSMZ—Deutsche Sammlung von Mikroorganismen and Zellkulturen GmbH.

In another aspect, the invention relates to a peptide comprising the sequence RGD selected from the group consisting of LRGDT (SEQ ID NO: 14), LRGDS (SEQ ID NO: 15), LRGDY (SEQ ID NO: 16), and DRGDG (SEQ ID NO: 17), or a variant thereof having at least 70% sequence identity with said sequences.

In another aspect, the invention relates to an agent according to the invention, or an antibody construct according to the invention, or a peptide according to the invention, or a polypeptide comprising the sequence of SEQ ID NO: 14, with the proviso that said polypeptide is not human CDH17, or a polypeptide comprising the sequence of SEQ ID NO 15 and/or the sequence of SEQ ID NO 16, with the proviso that said polypeptide is not human CDH5, or a polypeptide comprising the sequence of SEQ ID NO: 17, with the proviso that said polypeptide is not human CDH6 nor human CDH20, for use as a medicament.

In another aspect, the invention relates to an agent according to the invention, or an antibody construct according to the invention, or a peptide according to the invention, or a polypeptide comprising the sequence of SEQ ID NO: 14, with the proviso that said polypeptide is not human CDH17, or a polypeptide comprising the sequence of SEQ ID NO 15 and/or the sequence of SEQ ID NO 16, with the proviso that said polypeptide is not human CDH5, or a polypeptide comprising the sequence of SEQ ID NO: 17, with the proviso that said polypeptide is not human CDH6 nor human CDH20, for use in the treatment of cancer.

In another aspect, the invention relates to an in vitro method for diagnosing and/or prognosing and/or stratifying a cancer in a subject, comprising:
  i) contacting the agent or the antibody construct according to the invention with a biological sample from said subject;
  ii) separating said agent or antibody construct not bound to the sample;
  iii) detecting and/or quantifying the level of said agent or antibody construct bound to CDH17 and/or CDH5 and/or CDH6 and/or CDH20 in said biological sample;
  iv) comparing the level of said agent or antibody construct bound to CDH17 and/or CDH5 and/or CDH6 and/or CDH20 detected in step (iii) with that of a reference value; and
  v) correlating the result obtained with the presence and/or clinical outcome and/or stage of said cancer.

In another aspect, the invention relates to a pharmaceutical composition comprising a therapeutically effective amount of an agent according to the invention, or an antibody construct according to the invention, or a peptide according to the invention, or a polypeptide comprising the sequence of SEQ ID NO: 14, with the proviso that said polypeptide is not human CDH17, or a polypeptide comprising the sequence of SEQ ID NO 15 and/or the sequence of SEQ ID NO 16, with the proviso that said polypeptide is not human CDH5, or a polypeptide comprising the sequence of SEQ ID NO: 17, with the proviso that said polypeptide is not human CDH6 nor human CDH20, together with a pharmaceutically acceptable excipient or carrier.

In another aspect, the invention relates to the use of an epitope comprising residues 603 to 605 of human cadherin 17 (CDH17), and/or an epitope comprising residues 236 to 238 or residues 299 to 301 of human cadherin 5 (CDH5), and/or an epitope comprising residues 83 to 85 of human cadherin 6 (CDH6) and/or an epitope comprising residues 89 to 91 of human cadherin 20 (CDH20) as a marker of a cancer wherein cells expressing CDH17 and/or CDH5 and/or CDH6 and/or CDH20 participate.

In another aspect, the invention relates to the use of an epitope comprising residues 603 to 605 of human cadherin 17 (CDH17), and/or an epitope comprising residues 236 to 238 or residues 299 to 301 of human cadherin 5 (CDH5), and/or an epitope comprising residues 83 to 85 of human cadherin 6 (CDH6) and/or an epitope comprising residues 89 to 91 of human cadherin 20 (CDH20) as a metastatic marker of a cancer wherein cells expressing CDH17 and/or CDH5 and/or CDH6 and/or CDH20 participate.

DETAILED DESCRIPTION OF THE INVENTION

Definitions

Figure 1:
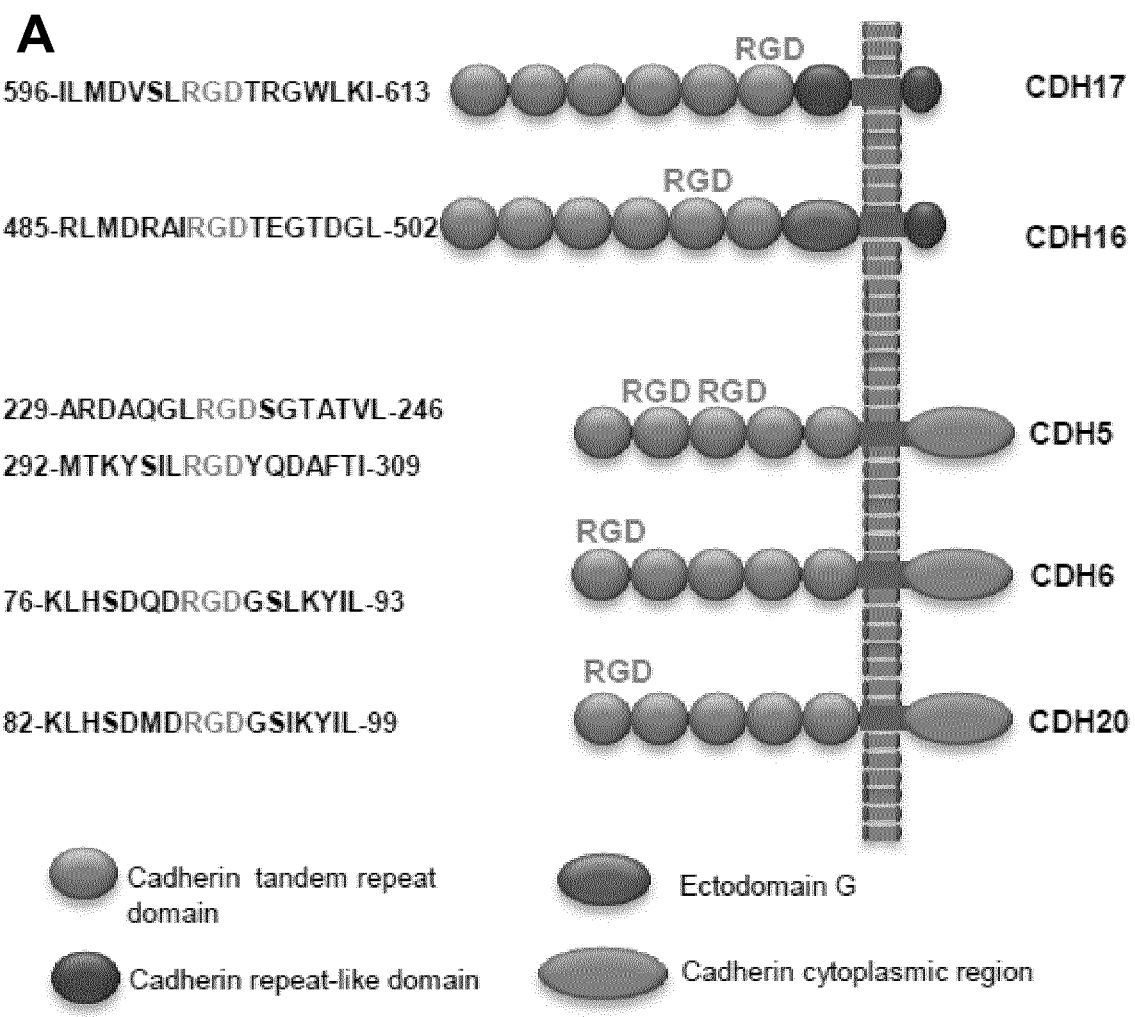
FIG. 1. Sequence analysis of the cadherin protein family reveals RGD motif in several cadherins. (A) Structure of five cadherins containing RGD motifs (right) and the flanking sequences of such motifs (left). (B) CDH16, CDH6, CDH20 were not detected and CDH5 barely detected in KM12SM and RKO cells by western blot (CDH5, CDH16) or PCR amplification assays (CDH6, CDH20). As positive controls we used breast cancer (MCF7), kidney clear cell carcinoma (786-O) and SK-MEL-103 and A375 melanoma cell lines.
Figure 1:
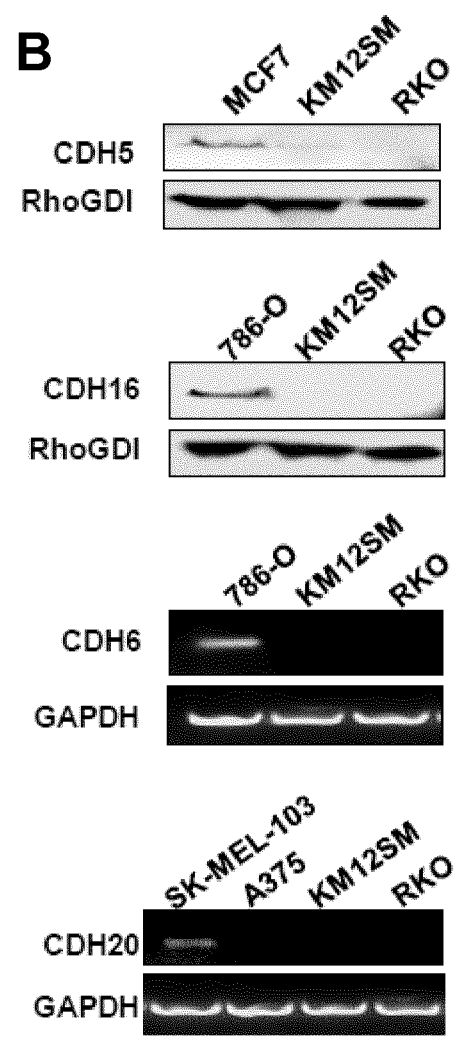

As used herein, the terms "agent" or "binding agent" are used indistinctively and refer to a molecule with capacity of binding specifically to its cognate target and show little or no binding to other molecules. In general, it is considered that an agent has high affinity for its cognate target whereas it has low affinities for other molecules. In the context of the invention, the agent may be an immunoglobulin agent or a non-immunoglobulin agent.

As used herein, the term "immunoglobulin agent" refers to a polypeptide binding agent having a structure based on an immunoglobulin domain or fold. Proteins having the immunoglobulin domain or fold include cell surface antigen receptors, co-receptors and co-stimulatory molecules of the immune system, molecules involved in antigen presentation to lymphocytes, cell adhesion molecules, certain cytokine receptors and intracellular muscle proteins. Particularly, the invention relates to immunoglobulin agents selected from an antibody or an antigen-binding fragment of said antibody.

The term "antibody", as used herein, refers to a glycoprotein that exhibits specific binding activity for a particular protein, which is referred to as "antigen". The term "antibody" comprises whole monoclonal antibodies or polyclonal antibodies, or fragments thereof, and includes human antibodies, antibodies, humanised antibodies, chimeric antibodies and antibodies of a non-human origin, such as murine antibodies, camelid antibodies and immunoglobulin new antigen receptor (IgNAR). "Monoclonal antibodies" are homogenous, highly specific antibody populations directed against a single site or antigenic "determinant". "Polyclonal antibodies" include heterogeneous antibody populations directed against different antigenic determinants. The antibodies may be of any isotype. The choice of isotype typically will be guided by the desired effector functions, such as ADCC induction. Exemplary isotypes are IgG1, IgG2, IgG3, and IgG4.

It is well known that the basic structural unit of an antibody comprises a tetramer. Each tetramer is constituted by two identical pairs of polypeptide chains, each of which is composed by a light chain (25 KDa) and by a heavy chain (50-75 KDa). The amino-terminal region of each chain includes a variable region of about 100-110 or more amino acids, which is involved in antigen recognition. The carboxy-terminal region of each chain comprises the constant region that mediates the effector function. The variable regions of each pair of light and heavy chains form the binding site of the antibody. Therefore, an intact antibody has two binding sites. Light chains are classified as κ or λ. Heavy chains are classified as γ, μ, α, δ and ε, and they define the isotype of the antibody as respectively IgG, IgM, IgA, IgD or IgE.

The variable regions of each pair of light and heavy chains form the binding site of the antibody. They are characterized by the same general structure constituted by relatively preserved regions called frameworks (FR) joined by three hyper-variable regions called complementarity determining regions (CDR). The term "complementarity determining region" or "CDR", as used herein, refers to the region within an antibody where this protein complements an antigen's shape. Thus, CDRs determine the protein's affinity (roughly, bonding strength) and specificity for specific antigens. The CDRs of the two chains of each pair are aligned by the framework regions, acquiring the function of binding a specific epitope. Consequently, both the heavy chain and the light chain are characterized by three CDRs, respectively CDR-H1, CDR-H2, CDR-H3 and CDR-L1, CDR-L2, CDR-L3.

By "humanised antibody" is meant an antibody derived from a non-human antibody, typically a murine antibody, that retains the antigen-binding properties of the parent antibody, but which is less immunogenic in humans. This may be achieved by various methods, including (a) grafting the entire non-human variable domains onto human constant regions to generate chimeric antibodies; (b) grafting only the non-human complementarity determining regions (CDRs) into human framework and constant regions with or without retention of critical framework residues; and (c) transplanting the entire non-human variable domains, but "cloaking" them with a human-like section by replacement of surface residues. Methods for humanizing non-human antibodies have been described in the art. Preferably, a humanised antibody has one or more amino acid residues introduced into it from a source which is non-human. These non-human amino acid residues are often referred to as "import" residues, which are typically taken from an "import" variable domain. It is further important that antibodies are humanised with retention of high affinity for the antigen and other favourable biological properties. To achieve this goal, humanised antibodies are prepared by a process of analysis of the parental sequences and various conceptual humanised products using three-dimensional models of the parental and humanised sequences. A further step in this approach, to make an antibody more similar to humans, is to prepare the so called primatised antibodies, i.e. a recombinant antibody which has been engineered to contain the variable heavy and light domains of a monkey (or other primate) antibody, in particular, a cynomolgus monkey antibody, and which contains human constant domain sequences, preferably the human immunoglobulin gamma 1 or gamma 4 constant domain (or PE variant).

By "human antibody" is meant an antibody containing entirely human light and heavy chains as well as constant regions, produced by any of the known standard methods.

By "murine antibody" is meant an antibody containing entirely murine light and heavy chains as well as constant regions, produced by any of the known standard methods.

The term "hybridoma", as used herein, refers to the hybrid cell line formed by fusing a specific antibody-producing B cell with a myeloma (B cell cancer) cell that is selected for its ability to grow in tissue culture and for an absence of antibody chain synthesis. The antibodies produced by the hybridoma are usually of a single specificity and are therefore monoclonal antibodies (in contrast to polyclonal antibodies).

The term "antibody fragment", as used herein, refers to a fragment of an antibody such as, for example, Fv, Fab, F(ab')2, and Fab' fragments. Various techniques have been developed for the production of antibody fragments. Traditionally, these fragments were derived via proteolytic digestion of intact antibodies but more recently these fragments can be produced directly by recombinant host cells. Papain digestion of antibodies produces two identical antigen-binding fragments, called "Fab" fragments, each with a single antigen-binding site, and a residual "Fc" fragment, which name reflects its ability to crystallize readily. Pepsin treatment yields an F(ab')$_2$ fragment that has two antigen-binding sites and is still capable of cross-linking antigen. "Fv" is the minimum antibody fragment which contains a complete antigen-recognition and antigen-binding site. This region consists of a dimer of one heavy chain and one light chain variable domain in tight, non-covalent association. It is in this configuration that the three hypervariable regions of each variable domain interact to define an antigen-binding site on the surface of the $V_H$-$V_L$ dimer. Collectively, the six CDRs confer antigen-binding specificity to the antibody. However, even a single variable domain (or half of an Fv comprising only three CDRs specific for an antigen) has the ability to recognize and bind the antigen, although with lower affinity than the entire binding site. The Fab fragment also contains the constant domain of the light chain and the first constant domain (CH1) of the heavy chain. Fab' fragments differ from Fab fragments by the addition of a few residues at the carboxy terminus of the heavy chain CH1 domain including one or more cysteines from the antibody hinge region.

The term "antibody construct", as used herein, refers to constructs based on antibody binding domains that are typically generated by genetic engineering techniques. Examples of antibody constructs include scFv, scFv-Fc, minibody, (scFv)$_2$ and diabody. These and other antibody constructs are reviewed in Cuesta et al., 2010 (Trends Biotechnol. 28:355-62), and are included herein by reference.

The term "heavy chain antibody", as used herein, refers to an antibody which consists only of two heavy chains and lacks the two light chains usually found in antibodies. Examples of heavy chain antibodies include the immunoglobulin new antigen receptor (IgNAR) of cartilaginous fishes, such as sharks, and the camelid antibody expressed in camelids, such as dromedaries, camels, llamas and alpacas. IgNARs have five constant domains (CH) per chain instead of the usual three, several disulfide bonds in unusual positions, and the CDR3 forms an extended loop covering the site which binds to a light chain in other antibodies. The heavy chains of the camelid antibodies have lost one of their constant domains (CH1) and underwent modifications in the variable domain (VH), both structural elements necessary for the binding of light chains.

As used herein, the term "non-immunoglobulin agent" refers to binding agents other than immunoglobulins that are based on different molecular natures, topologies or scaffolds. The term scaffold is meant to describe a protein framework that can carry altered amino acids or sequence insertions that confer on protein variants different functions, usually for binding specific targets. Examples of such non-immunoglobulin agents are well known in the art, and include without limitation peptide aptamers, nucleic acid aptamers, DARPins, affibodies, and anticalins. DARPins, affibodies, anticalins, and other protein scaffolds are reviewed in Binz et al., 2005 (Nat. Biotech. 23:1257-68), and are included herein by reference. The term "peptide aptamer" refers to a short variable peptide domain that is attached at both ends to a protein scaffold, and that binds to a specific target molecule. The variable loop length is typically composed of ten to twenty amino acids, and the scaffold may be any protein which has good solubility and compacity properties. Currently, the bacterial protein Thioredoxin-A is the most used scaffold protein, the variable loop being inserted within the reducing active site, which is a Cys-Gly-Pro-Cys loop (SEQ ID NO: 30) in the wild protein, the two Cys lateral chains being able to form a disulfide bridge. The term "nucleic acid aptamer" or "DNA aptamer", as used herein, refers to a short strand of DNA that has been engineered through repeated rounds of selection to bind to specific molecular targets.

The term "nucleic acid", as used herein, refers to polymers formed by the repetition of monomers called nucleotides linked by phosphodiester bonds. The term includes both DNA and RNA.

The term "linear peptide", as used herein, refers to a peptide comprising between 3 and 20 amino acids, having amino and carboxy-terminal free ends and being linear.

The term "cyclic peptide", as used herein, refers to refers to a peptide comprising between 3 and 20 amino acids, and being constrained by cyclisation at either the backbone or a side chain of the peptide.

The term "branched peptide", as used herein, refers to a peptide comprising between 3 and 20 amino acids, and at least an isopeptide bond. An "isopeptide bond" is an amide bond that is not present on the main chain of a peptide, and thereby forms an additional "branched" peptidic chain.

The terms "identical" or "percent identity" in the context of two or more CDR sequences, peptides or polypeptides, refer to two or more sequences or subsequences that are the same or have a specified percentage of amino acid residues that are the same, when compared and aligned (introducing gaps, if necessary) for maximum correspondence, not considering any conservative amino acid substitutions as part of the sequence identity. The percent identity can be measured using sequence comparison software or algorithms or by visual inspection. Various algorithms and software are known in the art that can be used to obtain alignments of amino acid or nucleotide sequences. One such non-limiting example of a sequence alignment algorithm is the algorithm incorporated into the NBLAST and XBLAST programs (Altschul et al., 1991, Nucleic Acids Res., 25:3389-3402). In certain embodiments, Gapped BLAST can be used. BLAST-2, WU-BLAST-2, ALIGN, ALIGN-2 (Genentech, South San Francisco, Calif.) or Megalign (DNASTAR) are additional publicly available software programs that can be used to align sequences. In certain embodiments, the percent identity between two nucleotide sequences is determined using the GAP program in GCG software (e.g., using a NWSgap-dna.CMP matrix and a gap weight of 40, 50, 60, 70, or 90 and a length weight of 1, 2, 3, 4, 5, or 6). In certain alternative embodiments, the GAP program in the GCG software package can be used to determine the percent identity between two amino acid sequences (e.g., using either a Blossum 62 matrix or a PAM250 matrix, and a gap weight of 16, 14, 12, 10, 8, 6, or 4 and a length weight of 1, 2, 3, 4, 5). Alternatively, in certain embodiments, the percent identity between nucleotide or amino acid sequences is determined using the algorithm of Myers and Miller (CABIOS, 4:11-17 (1989)). For example, the percent identity can be determined using the ALIGN program (version 2.0) and using a PAM120 with residue table, a gap length penalty of 12 and a gap penalty of 4. Appropriate parameters for maximal alignment by particular alignment software can be determined by one skilled in the art. In certain embodiments, the default parameters of the alignment software are used. In certain embodiments, the percentage identity "X" of a first amino acid sequence to a second sequence amino acid is calculated as 100×(Y/Z), where Y is the number of amino acid residues scored as identical matches in the alignment of the first and second sequences (as aligned by visual inspection or a particular sequence alignment program) and Z is the total number of residues in the second sequence. If the second sequence is longer than the first sequence, then the percent identity may be determined only in the region of overlap between said first and second sequences. In this case, the same formula as above can be used but using as Z value the length of the region wherein the first and second sequence overlaps, said region having a length which is substantially the same as the length of the first sequence.

As a non-limiting example, whether any particular polynucleotide has a certain percentage sequence identity (e.g., is at least 70% identical, at least 75% identical, at least 80% identical, at least 85% identical, at least 90% identical, and in some embodiments, at least 95%, 96%, 97%, 98%, or 99% identical) to a reference sequence can, in certain embodiments, be determined using the Bestfit program (Wisconsin Sequence Analysis Package, Version 8 for Unix, Genetics Computer Group, University Research Park, 575 Science Drive, Madison, Wis. 53711). Bestfit uses the local homology algorithm of Smith and Waterman, Advances in Applied Mathematics 2: 482 489 (1981), to find the best segment of homology between two sequences. When using Bestfit or any other sequence alignment program to determine whether a particular sequence is, for instance, 95% identical to a reference sequence according to the present invention, the parameters are set such that the percentage of identity is calculated over the full length of the reference amino acid sequence and that gaps in homology of up to 5% of the total number of amino acids in the reference sequence are allowed.

In some embodiments, two CDR sequences, peptides or polypeptides of the invention are substantially identical, meaning they have at least 70%, at least 75%, at least 80%, at least 85%, at least 90%, and in some embodiments at least 95%, 96%, 97%, 98%, 99% amino acid residue identity, when compared and aligned for maximum correspondence, as measured using a sequence comparison algorithm or by visual inspection. Identity can exist over a region of the sequences that is at least about 3, about 4, about 5, about 10, about 20, about 40-60 residues in length or any integral value there between, and can be over a longer region than 60-80 residues, for example, at least about 90-100 residues, and in some embodiments, the sequences are substantially identical over the full length of the sequences being compared.

The term "epitope", also known as antigenic determinant, refers to a part of an antigen that is recognised by the immune system, specifically by antibodies, B cells, or T cells, although in the context of the present invention this concept is also extended to recognition by non-immunoglobulin binding agents. For example, the epitope is the specific piece of the antigen that an antibody binds to.

The term "cadherin 17" or "CDH-17" or "CDH17", as used herein, refers to a protein consisting of an extracellular region, containing 7 cadherin domains, and a transmembrane region but lacking the conserved cytoplasmic domain, that is present in the gastrointestinal tract and pancreatic ducts. It is also known as intestinal peptide-associated transporter HPT-1, liver-intestine cadherin and LI-cadherin. The human CDH-17 is depicted under UniProt accession No. Q12864 (version 131, 11 Mar. 2015).

The term "cadherin 5" or "CDH-5" or "CDH5", as used herein, refers to a calcium-dependent cell—cell adhesion glycoprotein composed of five extracellular cadherin repeats, a transmembrane region and a highly conserved cytoplasmic tail that plays a role in intercellular junctions. It is also known as type 2 cadherin, vascular endothelial cadherin, VE-cadherin and CD144. The human CDH-5 is depicted under UniProt accession No. P33151 (version 138, 11 Mar. 2015).

The term "cadherin 6" or "CDH-6" or "CDH6", as used herein, refers to a a calcium dependent cell-cell adhesion glycoprotein composed of five extracellular cadherin repeats, a transmembrane region and a highly conserved cytoplasmic tail. It is also known as kidney cadherin or K-cadherin. The human CDH-6 is depicted under UniProt accession No. P55285 (version 133, 11 Mar. 2015).

The term "cadherin 20" or "CDH-20" or "CDH20", as used herein, refers to a calcium dependent cell-cell adhesion glycoprotein composed of five extracellular cadherin repeats, a transmembrane region and a cytoplasmic tail, lacking an HAV cell adhesion recognition sequence specific for classic cadherins. The human CDH-20 is depicted under UniProt accession No. Q9HBT6 (version 113, 31 Mar. 2015).

As used herein, the term "cancer wherein cells expressing CDH17 and/or CDH5 and/or CDH6 and/or CDH20 participate" refers to a cancer in which cells expressing CDH17 and/or CDH5 and/or CDH6 and/or CDH20 are directly or indirectly involved. The involvement of these types of cells is independent of CDH17 and/or CDH5 and/or CDH6 and/or CDH20 being or not responsible for the cancer. For example, CDH17 and/or CDH5 and/or CDH6 and/or CDH20 may be expressed in an altered way, location or distribution, or in altered amount, for example a higher value, with respect to normal or reference physiological conditions or reference values. As such, the term "cancer wherein cells expressing CDH17 and/or CDH5 and/or CDH6 and/or CDH20 participate" is substantially equivalent to "cancer concomitant with cells expressing CDH17 and/or CDH5 and/or CDH6 and/or CDH20", or "cancer wherein cells expressing CDH17 and/or CDH5 and/or CDH6 and/or CDH20 are directly or indirectly implied", or similar. Examples of cancers wherein cells expressing CDH17 and/or CDH5 and/or CDH6 and/or CDH20 participate include, without limitation, melanoma, breast cancer, and gastrointestinal cancers, such as colon cancer, pancreatic cancer, liver cancer, gastric cancer, and oesophagus carcinoma.

As cancers progress, they may metastasize. The term "metastasis" or "metastatic disease", as used herein, refers to the spread of a cancer or disease from one organ or part to another not directly connected with it. When tumour cells metastasize, the new tumour is called a secondary or metastatic tumour, and its cells are similar to those in the original tumour.

The term "marker" or "tumour marker" or "cancer marker", as used herein, refers to a biomarker found in a biological fluid, such as blood or urine, or in body tissues, such as tumour tissue, that can be elevated in cancer.

The term "treatment" or "therapy" can be used indistinctly and refer to clinical intervention in an attempt to prevent, cure, delay, reduce the severity of, or ameliorate one or more symptoms of the disease or disorder or recurring disease or disorder, or in order to prolong the survival of a patient beyond that expected in the absence of such treatment.

The term "sample" or "biological sample" is intended to refer to biological material isolated from a subject. The biological sample can contain any biological material suitable for detecting the desired biomarker and can comprise cell and/or non-cell material of the subject. The sample can be isolated from any suitable tissue or biological fluid such as for example, tumour tissue, blood, saliva, plasma, serum, urine, cerebrospinal liquid (CSF), faeces, a buccal or buccalpharyngeal swab, a surgical specimen, and a specimen obtained from a biopsy.

The term "subject", as used herein, refers to all animals classified as mammals and includes, without limitation, domestic and farm animals, primates and humans, e.g., human beings, non-human primates, cows, horses, pigs, sheep, goats, dogs, cats, or rodents. Preferably, the subject is a male or female human of any age or race.

The term "determining", as used herein, relates to the determination of any parameter that can be useful in the diagnosis, prognosis or stratification of a cancer in a subject. As will be understood by those skilled in the art, the determination of a parameter, although preferred to be, need not be correct for 100% of the subjects to be diagnosed or evaluated. The term, however, requires that a statistically significant portion of subjects can be identified as presenting a given parameter.

Whether a subject is statistically significant can be determined without further ado by the person skilled in the art using various well known statistic evaluation tools, e.g., determination of confidence intervals, p-value determination, Student's t-test, Mann-Whitney test, etc. Details are found in Dowdy and Wearden, Statistics for Research, John Wiley & Sons, New York 1983. Preferred confidence intervals are at least 50%, at least 60%, at least 70%, at least 80%, at least 90%, or at least 95%. The p-values are, preferably, 0.05, 0.01, 0.005 or lower.

1. Binding Agents

In a first aspect, the invention relates to an agent binding specifically to an epitope comprising residues 603 to 605 of human cadherin 17 (CDH17), hereinafter referred to as "the first binding agent of the invention", wherein said agent is an immunoglobulin agent or a non-immunoglobulin agent selected from the group consisting of a peptide aptamer, a nucleic acid aptamer, a DARPin, an affibody, and an anticalin.

In a particular embodiment, the epitope to which the agent binds comprises or consists of the sequence shown in SEQ ID NO: 14 (LRGDT). This sequence corresponds to residues 602 to 606 of human CDH17. It will be understood that the epitope to which the agent binds may comprise at least 1 residue, or at least 2 residues, or at least 3 residues, or at least 4 residues, or at least 5 residues, or at least 6 residues, or at least 7 residues, or at least 8 residues, or at least 9 residues, or at least 10 residues or more residues of the corresponding amino acid sequence of CDH17 at the N-terminus, or at the C-terminus, or both at the N- and C-terminus of the sequence shown in SEQ ID NO: 14 (LRGDT). In a preferred embodiment, the epitope to which the agent binds comprises or consists of the sequence shown in SEQ ID NO: 1 (VSLRGDTRG).

In a second aspect, the invention relates to an agent binding specifically to an epitope comprising residues 236 to 238 and/or residues 299 to 301 of human cadherin 5 (CDH5), hereinafter referred to as "the second binding agent of the invention", wherein said agent is an immunoglobulin agent or a non-immunoglobulin agent selected from the group consisting of a peptide aptamer, a nucleic acid aptamer, a DARPin, an affibody, and an anticalin.

The invention contemplates agents according to the second binding agent of the invention specifically binding to an epitope comprising residues 236 to 238 of human CDH-5 only, or specifically binding to residues 299 to 301 of human CDH5 only, or specifically binding to both epitopes, not necessarily simultaneously.

In a third aspect, the invention relates to an agent binding specifically to an epitope comprising residues 83 to 85 of human cadherin 6 (CDH6), hereinafter referred to as "the third binding agent of the invention", wherein said agent is an immunoglobulin agent or a non-immunoglobulin agent selected from the group consisting of a peptide aptamer, a nucleic acid aptamer, a DARPin, an affibody, and an anticalin.

In a fourth aspect, the invention relates to an agent binding specifically to an epitope comprising residues 89 to 91 of human cadherin 20 (CDH20), hereinafter referred to as "the fourth binding agent of the invention", wherein said agent is an immunoglobulin agent or a non-immunoglobulin agent selected from the group consisting of a peptide aptamer, a nucleic acid aptamer, a DARPin, an affibody, and an anticalin.

The invention also contemplates binding agents according to the first or second binding agents of the invention that are able to specifically bind to an epitope comprising residues 603 to 605 of human CDH17 and to an epitope comprising residues 236 to 238 and/or residues 299 to 301 of human CDH5. Binding agents according to the first or third binding agents of the invention that are able to specifically bind to an epitope comprising residues 603 to 605 of human CDH17 and to an epitope comprising residues 83 to 85 of human CDH6 are also contemplated. Binding agents according to the first or fourth binding agents of the invention that are able to specifically bind to an epitope comprising residues 603 to 605 of human CDH17 and to an epitope comprising residues 89 to 91 of human CDH20 are also contemplated. Binding agents according to the second or third binding agents of the invention that are able to specifically bind to an epitope comprising residues 236 to 238 and/or residues 299 to 301 of human CDH5 and to an epitope comprising residues 83 to 85 of human CDH6 are also contemplated. Binding agents according to the second or fourth binding agents of the invention that are able to specifically bind to an epitope comprising residues 236 to 238 and/or residues 299 to 301 of human CDH5 and to an epitope comprising residues 89 to 91 of human CDH20 are also contemplated. Binding agents according to the third or fourth binding agents of the invention that are able to specifically bind to an epitope comprising residues 83 to 85 of human CDH6 and to an epitope comprising residues 89 to 91 of human CDH20 are also contemplated.

Binding agents according to the first, second and third binding agents of the invention that are able to specifically bind to an epitope comprising residues 603 to 605 of human CDH17, and to an epitope comprising residues 236 to 238 and/or residues 299 to 301 of human CDH5, and to an epitope comprising residues 83 to 85 of human CDH6 are also contemplated. Binding agents according to the first, second and fourth binding agents of the invention that are able to specifically bind to an epitope comprising residues 603 to 605 of human CDH17, and to an epitope comprising residues 236 to 238 and/or residues 299 to 301 of human CDH5, and to an epitope comprising residues 89 to 91 of human CDH20 are also contemplated. Binding agents according to the first, third and fourth binding agents of the invention that are able to specifically bind to an epitope comprising residues 603 to 605 of human CDH17, and to an epitope comprising residues 83 to 85 of human CDH6, and to an epitope comprising residues 89 to 91 of human CDH20 are also contemplated. Binding agents according to the second, third and fourth binding agents of the invention that are able to specifically bind to an epitope comprising residues 236 to 238 and/or residues 299 to 301 of human CDH5, and to an epitope comprising residues 83 to 85 of human CDH6, and to an epitope comprising residues 89 to 91 of human CDH20 are also contemplated.

Binding agents according to the first, second, third and fourth binding agents of the invention that are able to specifically bind to an epitope comprising residues 603 to 605 of human CDH17, and to an epitope comprising residues 236 to 238 and/or residues 299 to 301 of human CDH5, and to an epitope comprising residues 83 to 85 of human CDH6, and to an epitope comprising residues 89 to 91 of human CDH20 are also contemplated.

It also will be understood that the first, second, third and fourth binding agents of the invention need not bind to all the epitopes they recognise simultaneously.

In another particular embodiment of the first, second, third or fourth binding agents of the invention, said agent is an immunoglobulin agent selected from an antibody and an antigen-binding fragment of said antibody. In a preferred embodiment, said antibody-binding fragment is selected from the group consisting of Fv, Fab, F(ab')$_2$, and Fab'.

In another particular embodiment of the first, second, third or fourth binding agents of the invention, said antibody or said antigen-binding fragment comprises or consists of, within the heavy chain:
  a CDR comprising the amino acid sequence shown in SEQ ID NO: 2 [CDR-H1], a CDR comprising the amino acid sequence shown in SEQ ID NO: 3 [CDR-H2], and a CDR comprising the amino acid sequence shown in SEQ ID NO: 4 [CDR-H3], or a functionally equivalent variant of said CDRs,
  or
  a CDR comprising the amino acid sequence shown in SEQ ID NO: 5 [CDR-H1], a CDR comprising the amino acid sequence shown in SEQ ID NO: 6 [CDR-H2], and a CDR comprising the amino acid sequence shown in SEQ ID NO: 7 [CDR-H3], or a functionally equivalent variant of said CDRs.

In a preferred embodiment, said antibody or the said antigen-binding fragment comprises or consists of:
  within the heavy chain, a CDR-H1 comprising the amino acid sequence shown in SEQ ID NO: 2, a CDR-H2 comprising the amino acid sequence shown in SEQ ID NO: 3, and a CDR-H3 comprising the amino acid sequence shown in SEQ ID NO: 4, and within the light chain, a CDR-L1 comprising the amino acid sequence shown in SEQ ID NO: 8, a CDR-L2 comprising the amino acid sequence shown in SEQ ID NO: 9, and a CDR-L3 comprising the amino acid sequence shown in SEQ ID NO: 10, or a functionally equivalent variant of said CDRs,
  or
  within the heavy chain, a CDR comprising the amino acid sequence shown in SEQ ID NO: 5 [CDR-H1], a CDR comprising the amino acid sequence shown in SEQ ID NO: 6 [CDR-H2], and a CDR comprising the amino acid sequence shown in SEQ ID NO: 7 [CDR-H3], and within the light chain, a CDR-L1 comprising the amino acid sequence shown in SEQ ID NO: 11, a CDR-L2 comprising the amino acid sequence shown in SEQ ID NO: 12, and a CDR-L3 comprising the amino acid sequence shown in SEQ ID NO: 13, or a functionally equivalent variant of said CDRs.

It will be immediately apparent for the skilled person that these two sets of CDRs belong to the antibodies sequenced in Example 10, which are also part of the present invention.

The person skilled in the art will understand that the amino acid sequences of the CDRs of the antibody or antibody fragment according to the first, second and third binding agent of the invention can include one or more amino acid substitutions such that, even though the primary sequence of the polypeptide is altered, the capacity of the antibody to bind to an epitope comprising residues 603 to 605 of human CDH17, and/or to an epitope comprising residues 236 to 238 and/or residues 299 to 301 of human CDH5, and/or to an epitope comprising residues 83 to 85 of human CDH6, and/or to an epitope comprising residues 89 to 91 of human CDH20 is maintained. Said substitution may be a conservative substitution, which in general indicates that one amino acid is substituted with another amino acid having similar properties. For example, the substitution of glutamic acid (negatively charged amino acid) with aspartic acid would be a conservative amino acid substitution.

The present invention also contemplates functionally equivalent variants of the sequences of the CDRs of shown in SEQ ID NO: 2 to 13, which fall within the scope of the invention. As it is used herein, the term "functionally equivalent variant of a CDR sequence" refers to a sequence variant of a particular CDR sequence having substantially similar sequence identity with it and substantially maintaining its capacity to bind to its cognate antigen when being part of an antibody or antibody fragment as the ones described herein. For example, a functionally equivalent variant of a CDR sequence may be a polypeptide sequence derivative of said sequence comprising the addition, deletion or substitution of one or more amino acids.

Functionally equivalent variants of a CDR sequence according to the invention include CDR sequences having at least approximately 70%, at least 75%, at least 80%, at least 85%, at least 90%, at least 91%, at least 92%, at least 93%, at least 94%, at least 95%, at least 96%, at least 97%, at least 98% or at least 99% sequence identity with the corresponding amino acid sequences shown in one of SEQ ID NOs: 2 to 13. It is also contemplated that functionally equivalent variants of a CDR sequence comprise additions consisting of at least 1 amino acid, or at least 2 amino acids, or at least 3 amino acids, or at least 4 amino acids, or at least 5 amino acids, or at least 6 amino acids, or at least 7 amino acids, or at least 8 amino acids, or at least 9 amino acids, or at least 10 amino acids or more amino acids at the N-terminus, or at the C-terminus, or both at the N- and C-terminus of the corresponding amino acid sequence shown in one of SEQ ID NOs: 2 to 13. Likewise, it is also contemplated that variants comprise deletions consisting of at least 1 amino acid, or at least 2 amino acids, or at least 3 amino acids, or at least 4 amino acids, or at least 5 amino acids, or at least 6 amino acids, or at least 7 amino acids, or at least 8 amino acids, or at least 9 amino acids, or at least 10 amino acids or more amino acids at the N-terminus, or at the C-terminus, or both at the N- and C-terminus of the corresponding amino acid sequence shown in one of SEQ ID NOs: 2 to 13.

Functionally equivalent variants a CDR sequence according to the invention will preferably maintain at least 50%, at least 60%, at least 70%, at least 75%, at least 80%, at least 85%, at least 90%, at least 91%, at least 92%, at least 93%, at least 94%, at least 95%, at least 96%, at least 97%, at least 98%, at least 99%, at least 100%, at least 105%, at least 110%, at least 115%, at least 120%, at least 125%, at least 130%, at least 135%, at least 140%, at least 145%, at least 150%, at least 200% or more of the capacity of the corresponding amino acid sequence shown in one of SEQ ID NOs: 2 to 13 to bind to its cognate antigen when being part of an antibody or antibody fragment as the ones of the invention. This capacity to bind to its cognate antigen may be determined as a value of affinity, avidity, specificity and/or selectivity of the antibody or antibody fragment to its cognate antigen.

The capacity of the binding agents according to the invention, and in particular of the antibody or antibody fragment as described herein, to bind to an epitope comprising residues 603 to 605 of human CDH17, and/or to an epitope comprising residues 236 to 238 and/or residues 299 to 301 of human CDH5, and/or to an epitope comprising residues 83 to 85 of human CDH6 can be determined by a number of assays that are well known in the art. Preferably, the binding capacity of the binding agents is determined by immunoprecipitation or by an in vitro binding assay, such as radioimmunoassay (RIA), enzyme-linked immunoabsorbent assay (ELISA), surface plasmon resonance or by immunofluorescent techniques such as immunohistochemistry (IHC), fluorescence microscopy or flow cytometry. The affinity of the binding agent of the invention for an epitope comprising residues 603 to 605 of human CDH17, and/or an epitope comprising residues 236 to 238 and/or residues 299 to 301 of human CDH5, and/or an epitope comprising residues 83 to 85 of human CDH6 and/or to an epitope comprising residues 89 to 91 of human CDH20 is at least $10^{-6}$ M, at least $10^{-7}$ M, at least $10^{-8}$ M, at least $10^{-9}$ M, at least $10^{-10}$ M, at least $10^{-11}$, at least $10^{-12}$ M, or more.

In another particular embodiment of the first, second, third or fourth binding agents of the invention, said agent is the antibody produced by the hybridoma cell line with reference PA383-25.4.1, deposited under Accession number DSM ACC3266 on 9 Apr. 2015 at the Leibniz Institut DSMZ—Deutsche Sammlung von Mikroorganismen und Zellkulturen (DSMZ) GmbH or an antigen-binding fragment thereof.

In a preferred embodiment, the antigen-binding fragment of the antibody produced by the hybridoma cell line with reference PA383-25.4.1, deposited under Accession number DSM ACC3266 on 9 Apr. 2015 at the Leibniz Institut DSMZ—Deutsche Sammlung von Mikroorganismen und Zellkulturen (DSMZ) GmbH is selected from from the group consisting of Fv, Fab, F(ab')$_2$, and Fab'.

In another particular embodiment of the first, second, third or fourth binding agents of the invention, said antibody or said antigen-binding fragment is humanised.

In another particular embodiment of the first, second, third or fourth binding agents of the invention, said antibody or said antigen-binding fragment is human.

In another particular embodiment of the first, second, third or fourth binding agents of the invention, said antibody or said antigen-binding fragment is murine.

In another particular embodiment of the first, second, third or fourth binding agents of the invention, said antibody or antigen-binding fragment is an immunoglobulin new antigen receptor (IgNAR).

In another particular embodiment of the first, second, third or fourth binding agents of the invention, said antibody or antigen-binding fragment is a camelid antibody.

In another embodiment of the first, second, third or fourth binding agents of the invention, the agent is a non-immunoglobulin agent selected from the group consisting of a peptide aptamer, a nucleic acid aptamer, a DARPin, an affibody, and an anticalin.

In a preferred embodiment, the non-immunoglobulin agent is a peptide aptamer. In another preferred embodiment, the non-immunoglobulin agent is a nucleic acid aptamer. In another preferred embodiment, the non-immunoglobulin agent is a DARPin. In another preferred embodiment, the non-immunoglobulin agent is an affibody. In another preferred embodiment, the non-immunoglobulin agent is an anticalin.

It will be immediately apparent for the person skilled in the art that the antigen binding fragments described herein may be modified by genetic engineering to yield constructs with modified avidity and/or functionality. There are numerous approaches in the art to obtain antibody constructs, such as those highlighted in Cuesta et al. (cited supra).

Thus, in another aspect, the invention relates to an antibody construct, hereinafter the antibody construct of the invention, comprising the antigen-binding fragment according to the antibody fragments described in relation with the first, second, third or fourth binding agents of the invention, wherein the antibody construct is selected from the group consisting of scFv, scFv-Fc, minibody, (scFv)$_2$ and diabody.

In a particular embodiment, the antibody construct is a scFv. In another particular embodiment, the antibody construct is a scFv-Fc. In another particular embodiment, the antibody construct is a minibody. In another particular embodiment, the antibody construct is a (scFv)$_2$. In another particular embodiment, the antibody construct is a diabody.

In another particular embodiment, the antibody construct is selected from the group consisting of scFv, scFv-Fc, minibody, (scFv)$_2$ and diabody comprises the antigen-binding fragment of the antibody produced by the hybridoma cell line with reference PA383-25.4.1, deposited under Accession number DSM ACC3266 on 9 Apr. 2015 at the Leibniz Institut DSMZ—Deutsche Sammlung von Mikroorganismen and Zellkulturen (DSMZ) GmbH.

Amino acid sequence modification(s) of the binding agents and antibody constructs described herein in positions other than the CDRs or the binding sites are also contemplated. For example, it may be desirable to improve the binding affinity and/or other biological properties of the binding agent. Amino acid sequence variants of the binding agent are prepared by introducing appropriate nucleotide changes into the antibody encoding nucleic acid, or by peptide synthesis. Such modifications include, for example, deletions from, and/or insertions into and/or substitutions of, residues within the amino acid sequences of the binding agent. Any combination of deletion, insertion, and/or substitution is made, provided that the final binding agent possesses the desired characteristics. The amino acid changes may also alter post-translational processes of the protein, such as changing the number or position of glycosylation sites. Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include a peptide with an N-terminal methionyl residue or the antibody polypeptidic chain fused to a cytotoxic polypeptide. Other insertional variants of the molecule include the fusion to the N- or C-terminus of an enzyme, or a polypeptide which increases its serum half-life.

In the particular embodiment of the binding agent being an antibody, another type of amino acid variant of the antibody alters its original glycosylation pattern. By altering is meant deleting one or more carbohydrate moieties found in the molecule, and/or adding one or more glycosylation sites that are not present in it. Glycosylation of polypeptides is typically either N-linked or O-linked. N-linked refers to the attachment of the carbohydrate moiety to the side chain of an asparagine residue. The tripeptide sequences asparagine-X-serine and asparagine-X-threonine, where X is any amino acid except proline, are the recognition sequences for enzymatic attachment of the carbohydrate moiety to the asparagine side chain. Thus, the presence of any of these tripeptide sequences in a polypeptide creates a potential glycosylation site. O-linked glycosylation refers to the attachment of one of the monosaccharides or monosaccharide derivatives N-acetylgalactosamine, galactose, or xylose to a hydroxyamino acid, most commonly serine or threonine, although 5-hydroxyproline or 5-hydroxylysine may also be used. Addition of glycosylation sites to the antibody is conveniently accomplished by altering the amino acid sequence such that it contains one or more of the above-described tripeptide sequences (for N-linked glycosylation sites). The alteration may also be made by the addition of, or substitution by, one or more serine or threonine residues to the sequence of the original antibody (for O-linked glycosylation sites). Nucleic acid molecules encoding amino acid sequence variants of the antibody are prepared by a variety of methods known in the art. These methods include, but are not limited to, isolation from a natural source (in the case of naturally occurring amino acid sequence variants) or preparation by oligonucleotide-mediated (or site-directed) mutagenesis, PCR mutagenesis, and cassette mutagenesis of an earlier prepared variant or a non-variant version of the antibody.

Also, it may be desirable to modify the antibodies described herein in order to improve their effector function, e.g. so as to enhance ADCC and/or CDC of the antibody. This may be achieved by introducing one or more amino acid substitutions in an Fc region of an antibody. Glycosyl groups added to the amino acid backbone of glycoproteins e.g. antibodies are formed by several monosaccharides or monosaccharide derivatives in resulting in a composition which can be different in the same antibody produced in cell from different mammals or tissues. In addition, it has been shown that different composition of glycosyl groups can affect the potency in mediating antigen-dependent cell-mediated cytotoxicity (ADCC) and/or complement dependent cytotoxicity (CDC) of the antibody. Therefore it is possible to improve those properties by mean of studying the pattern of glycosilation of antibodies from different sources.

Other modifications suitable for the antibodies described herein include the introduction of cysteine residue(s) in the Fc region, thereby allowing interchain disulfide bond formation in this region to improve the internalisation capability and/or increase complement-mediated cell killing and antibody-dependent cellular cytotoxicity (ADCC).

In order to increase the serum half-life of the binding agent, one may incorporate a salvage receptor binding epitope into the agent. As used herein, the term "salvage receptor binding epitope" refers to an epitope of the Fc region of an IgG molecule (e.g., IgG1, IgG2, IgG3, or IgG4) that is responsible for increasing the in vivo serum half-life of the IgG molecule.

In another aspect, the invention relates to a nucleic acid, hereinafter "the nucleic acid of the invention", selected form the group consisting of:
a) a nucleic acid encoding the agent according to the first, second and third binding agents of the invention, or the antibody construct according to the invention, and
b) a complementary nucleic acid of a nucleic acid as defined in a).

Said nucleic acid of the invention can contain a regulatory sequence operatively linked for the expression of the nucleotide sequence encoding the binding agent or the antibody construct of the invention, thereby forming a gene construct, hereinafter the "gene construct of the invention". As used herein, the term "operatively linked" means that the binding agent or antibody construct encoded by the nucleic acid sequence of the invention is expressed in the correct reading frame under control of the expression control or regulating sequences. Therefore, in another aspect, the invention provides an expression cassette, hereinafter the "expression cassette of the invention", comprising the gene construct of the invention operatively linked to an expression control sequence. The gene construct of the invention can be obtained through the use of techniques widely known in the prior art.

Control sequences are sequences that control and regulate transcription and, where appropriate, the translation of said antibody, and include promoter sequences, transcriptional regulators encoding sequences, ribosome binding sequences (RBS) and/or transcription terminating sequences. The expression cassette of the present invention may additionally include an enhancer, which may be adjacent to or distant from the promoter sequence and can function to increase transcription from the same. In a particular embodiment, said expression control sequence is functional in prokaryotic cells and organisms, such as bacteria, etc. Whereas in another particular embodiment, said expression control sequence is functional in eukaryotic cells and organisms, for example, insect cells, plant cells, mammalian cells, etc.

Any available promoter can be used in this methodology. In a preferred embodiment of the present invention, the promoter used in the nucleic acid construct of the present invention is active in the specific cell population to be transfected. Illustrative, non-limiting examples of ubiquitous promoters which can be present in the expression cassette of the invention include the human cytomegalovirus promoter (hCMV), SV40 promoter, the EF1-alpha promoter to, and the ubiquitin promoter C. Illustrative, non-limiting examples of cell-type specific promoters and/or tissue specific promoters such as albumin include which is specific for liver, lymphoid-specific promoters, and so on.

Advantageously, the expression cassette of the invention further comprises a marker or gene encoding a motif or phenotype which allows selecting the transformed host cell with said expression cassette. Illustrative examples of said markers that could be present in the expression cassette of the invention include antibiotic resistance genes, genes for resistance to toxic compounds, and in general, all those that allow selecting the genetically transformed cells.

The gene constructs of the invention or the expression cassette of the invention can be inserted into appropriate vectors. Thus, in another aspect, the invention relates to a vector, such as an expression vector, hereinafter "the vector of the invention", comprising said gene constructs or said expression cassettes of the invention. The choice of vector depends on the host cell in which it will be subsequently introduced. As an example, the vector into which is inserted the said nucleic acid sequences may be a plasmid or a vector which, when introduced into a host cell, is integrated or not in the genome of said cell. Obtaining this vector can be performed by conventional methods known to those skilled in the art. In a particular embodiment, said recombinant vector is a vector useful to transfect animal cells.

Said vector can be used to transform, transfect or infect cells susceptible of being transformed, transfected or infected by said vector. Such cells can be prokaryotic or eukaryotic. Therefore, in another aspect, the invention relates to a cell, hereinafter "the cell of the invention", comprising the nucleic acid or the expression cassette or the vector according to the invention. In order to obtain the cell of the invention, the cell may need to be transformed, transfected or infected with the vector of the invention. Said transformed cell, transfected or infected comprises, therefore, a nucleic acid of the invention, a gene construct of the invention or an expression cassette or vector of the invention.

Transformed cells, transfected or infected may be obtained by conventional methods known to those skilled in the art. Cells suitable for performing the invention include, without limitation, mammalian, plant, insect, fungal and bacterial cells. Bacterial cells include, without limitation, cells from Gram positive bacteria such as species of the genus Bacillus, Streptomyces and Staphylococcus and Gram-negative bacterial cells such as cells of the genus *Escherichia* and Pseudomonas. Fungal cells preferably include yeast cells such as Saccharomyces, Pichia pastoris and Hansenula polymorpha. Insect cells include, without limitation, Drosophila cells and Sf9 cells. Plant cells include, among others, cells of crop plants such as cereals, medicinal, ornamental or bulbs. Mammalian cells suitable for the present invention include epithelial cell lines, osteosarcoma cell lines, neuroblastoma cell lines, epithelial carcinomas, glial cells, hepatic cell lines, CHO cells, COS cells, BHK cells, HeLa cells, 911 cells, AT1080 cells, A549 cells, HEK 293 and 293T cells, PER.C6 cells, NTERA-2 human ECCs cells, D3 cells of the mESCs line, human embryonic stem cells such as HS293, hMSCs and BGV01, SHEF1, SHEF2 and HS181, NIH3T3 cells, REH and MCF-7 cells.

In another aspect, the invention relates to the hybridoma cell line with reference PA383-25.4.1, deposited under Accession number DSM ACC3266 on 9 Apr. 2015 at the Leibniz Institut DSMZ—Deutsche Sammiung von Mikroorganismen and Zellkulturen (DSMZ) GmbH hereinafter "the hybridoma cell line of the invention".

In another aspect, the invention relates to a method for producing said antibody of the invention, which comprises growing the cell or the hybridoma cell line of the invention under conditions permitting the production of the binding agent of the invention. The conditions for optimising the culture of said cell will depend on the cell used. If desired, the method for producing the antibody of the invention further includes the isolation and purification of said binding agent.

2. Peptides

In another aspect, the invention relates to a peptide, hereinafter referred to as "the peptide of the invention", comprising the sequence RGD selected from the group consisting of LRGDT (SEQ ID NO: 14), LRGDS (SEQ ID NO: 15), LRGDY (SEQ ID NO: 16), DRGDG (SEQ ID NO: 17) or a variant thereof having at least 70% sequence identity with said sequences.

The skilled person will immediately appreciate that the sequence shown in SEQ ID NO: 14 corresponds to residues 602 to 606 of human CDH17, the sequence shown in SEQ ID NO: 15 corresponds to residues 235 to 239 of human CDH5, the sequence shown in SEQ ID NO: 16 corresponds to residues 298 to 302 of human CDH5, the sequence shown in SEQ ID NO: 17 corresponds to residues 82 to 86 of human CDH6 as well as to residues 88 to 92 of human CDH20.

The present invention also contemplates variants of the peptides comprising the sequences shown in SEQ ID NO: 14 to 17 having at least 70% sequence identity with said sequences. Thus, variants of the peptide of the invention include peptides with sequences having at least approximately 70%, at least 75%, at least 80%, at least 85%, at least 90%, at least 91%, at least 92%, at least 93%, at least 94%, at least 95%, at least 96%, at least 97%, at least 98% or at least 99% sequence identity with the corresponding amino acid sequences shown in one of SEQ ID NOs: 14 to 17.

It is also contemplated that a variant of the peptides shown in SEQ ID NO: 14 to 17 having at least 70% sequence identity with said sequences comprise additions consisting of at least 1 amino acid, or at least 2 amino acids, or at least 3 amino acids, or at least 4 amino acids, or at least 5 amino acids, or at least 6 amino acids, or at least 7 amino acids, or at least 8 amino acids, or at least 9 amino acids, or at least 10 amino acids or more amino acids from the corresponding sequence of CDH17, CDH5 or CDH6 located at the N-terminus, or at the C-terminus, or both at the N- and C-terminus of the amino acid sequence shown in one of SEQ ID NOs: 14 to 17.

In a particular embodiment, the peptide of the invention is selected from the group consisting of SLRGDTR (SEQ ID NO: 32), GLRGDSG (SEQ ID NO: 33), ILRGDYQ (SEQ ID NO: 34), QDRGDGS (SEQ ID NO: 35), and MDRGDGS (SEQ ID NO: 36). In a preferred embodiment, the peptide of the invention is selected from the group consisting of VSLRGDTRG (SEQ ID NO: 1), QGLRGDSGT (SEQ ID NO: 37), SILRGDYQD (SEQ ID NO: 19), DQDRGDGSL (SEQ ID NO: 38), and DMDRGDGSI (SEQ ID NO: 39).

In a particular embodiment, said peptide is a linear peptide. In another particular embodiment, said peptide is a cyclic peptide. In another particular embodiment, said peptide is a branched peptide.

3. Therapeutic Uses

The authors of the present invention have shown that the RGD motif present in CDH17 induces integrin activation and tumour growth, as is shown in Examples 1 to 6. These results were used as bait for the generation of antibodies binding specifically to the RGD motif of CDH17 with capacity to inhibit the activation of β1 integrin (Examples 8 and 10). Thus, these antibodies have a potential therapeutic effect in cancers expressing CDH17, by decreasing tumour growth and metastasis (Example 6).

Since there are also other RGD motifs present in other cadherins, such as CDH5 and CDH6, this observation can also be extrapolated to these cadherins, as is shown in Example 11.

Thus, this motif could be targeted to avoid dissemination of those tumours expressing these cadherins.

Thus, in another aspect, the invention relates to:
an agent according to the invention, or
an antibody construct according to the invention, or
a peptide according to the invention, or
a polypeptide comprising the sequence of SEQ ID NO: 14, with the proviso that said polypeptide is not human CDH17, or
a polypeptide comprising the sequence of SEQ ID NO 15 and/or the sequence of SEQ ID NO 16, with the proviso that said polypeptide is not human CDH5, or
a polypeptide comprising the sequence of SEQ ID NO: 17, with the proviso that said polypeptide is not human CDH6 nor human CDH20, for use as a medicament, hereinafter referred to as "the first medical use of the invention".

In another aspect, the invention relates to:
an agent according to the invention, or
an antibody construct according to the invention, or
a peptide according to the invention, or
a polypeptide comprising the sequence of SEQ ID NO: 14, with the proviso that said polypeptide is not human CDH17, or
a polypeptide comprising the sequence of SEQ ID NO 15 and/or the sequence of SEQ ID NO 16, with the proviso that said polypeptide is not human CDH5, or
a polypeptide comprising the sequence of SEQ ID NO: 17, with the proviso that said polypeptide is not human CDH6 nor human CDH20, for use in the treatment of cancer, hereinafter referred to as "the second medical use of the invention".

This aspect may be reformulated as the use of an agent according to the invention, or an antibody construct according to the invention, or a peptide according to the invention, or a polypeptide comprising the sequence of SEQ ID NO:

14, with the proviso that said polypeptide is not human CDH17, or a polypeptide comprising the sequence of SEQ ID NO 15 and/or the sequence of SEQ ID NO 16, with the proviso that said polypeptide is not human CDH5, or a polypeptide comprising the sequence of SEQ ID NO: 17, with the proviso that said polypeptide is not human CDH6 nor human CDH20, in the fabrication of a medicament for the treatment of cancer. Alternatively, this aspect may also be reformulated as a method for treating a cancer in a subject in need thereof comprising the administration of an agent according to the invention, or an antibody construct according to the invention, or a peptide according to the invention, or a polypeptide comprising the sequence of SEQ ID NO: 14, with the proviso that said polypeptide is not human CDH17, or a polypeptide comprising the sequence of SEQ ID NO 15 and/or the sequence of SEQ ID NO 16, with the proviso that said polypeptide is not human CDH5, or a polypeptide comprising the sequence of SEQ ID NO: 17, with the proviso that said polypeptide is not human CDH6 nor human CDH20, to said subject.

The terms "agent", "antibody construct", and "peptide" have been described in detail previously, and their definitions and particular and preferred embodiments are included herein by reference.

In a particular embodiment of the first and second medical uses of the invention, the polypeptide comprising the sequence of SEQ ID NO: 14, with the proviso that said polypeptide is not human CDH17, is domain 6 of CDH17. In another particular embodiment the polypeptide comprising the sequence of SEQ ID NO 15, with the proviso that said polypeptide is not human CDH5, is a polypeptide comprising or consisting of domain 2 of CHDS. In another particular embodiment the polypeptide comprising the sequence of SEQ ID NO 16, with the proviso that said polypeptide is not human CDH5, is a polypeptide comprising or consisting of domain 3 of CHDS. In another particular embodiment the polypeptide comprising the sequence of SEQ ID NO 15 and the sequence of SEQ ID NO 16, with the proviso that said polypeptide is not human CDH5, is a polypeptide comprising or consisting of domains 2 and 3 of CHDS. In another particular embodiment the polypeptide comprising the sequence of SEQ ID NO 17, with the proviso that said polypeptide is not human CDH6, is a polypeptide comprising or consisting of domain 1 of CDH6. In another particular embodiment the polypeptide comprising the sequence of SEQ ID NO: 17, with the proviso that said polypeptide is not human CDH20, is a polypeptide comprising or consisting of domain 1 of CDH20

In a particular embodiment of the second medical use of the invention, the cancer is a cancer wherein cells expressing CDH17 and/or CDH5 and/or CDH6 and/or CDH20 participate.

In a preferred embodiment, said cancer wherein cells expressing CDH17 and/or CDH5 and/or CDH6 and/or CDH20 participate is selected from melanoma, breast cancer, and a gastrointestinal cancer. In a more preferred embodiment, said gastrointestinal cancer is selected from the group consisting of colon cancer, pancreatic cancer, liver cancer, gastric cancer, and oesophagus carcinoma.

In a more preferred embodiment, said gastrointestinal cancer is colon cancer. In a more preferred embodiment, said gastrointestinal cancer is pancreatic cancer. In a more preferred embodiment, said gastrointestinal cancer is liver cancer. In a more preferred embodiment, said gastrointestinal cancer is gastric cancer. In a more preferred embodiment, said gastrointestinal cancer is oesophagus cancer.

In another preferred embodiment, said cancer wherein cells expressing CDH17 and/or CDH5 and/or CDH6 and/or CDH20 participate is metastatic.

As the person skilled in the art will recognise, these therapeutic applications will comprise the administration of a therapeutically effective amount of the antibody construct, or peptide according to the invention, or the polypeptide comprising the sequence of SEQ ID NO: 14, with the proviso that said polypeptide is not human CDH17, a polypeptide comprising the sequence of SEQ ID NO 15 and/or the sequence of SEQ ID NO 16, with the proviso that said polypeptide is not human CDH5, or a polypeptide comprising the sequence of SEQ ID NO: 17, with the proviso that said polypeptide is not human CDH6 nor human CDH20.

The term "therapeutically effective amount", as used herein, refers to the amount of the agent, antibody construct, or peptide according to the invention, or the polypeptide comprising the sequence of SEQ ID NO: 14, with the proviso that said polypeptide is not human CDH17, a polypeptide comprising the sequence of SEQ ID NO 15 and/or the sequence of SEQ ID NO 16, with the proviso that said polypeptide is not human CDH5, or a polypeptide comprising the sequence of SEQ ID NO: 17, with the proviso that said polypeptide is not human CDH6 nor human CDH20, which is required to achieve an appreciable prevention, cure, delay, reduction of the severity of, or amelioration of one or more symptoms of the disease or condition wherein cells expressing CDH17 and/or CDH5 and/or CDH6 and/or CDH20 participate. The person skilled in the art will be able to determine therapeutically effective amounts of these molecules without undue experimentation by means of conventional techniques well-known in the art, such as those used in Example 6.

Without wishing to be bound by any theory, it is hypothesised that the agent, antibody construct, or peptide according to the invention, or the polypeptide comprising the sequence of SEQ ID NO: 14, with the proviso that said polypeptide is not human CDH17, a polypeptide comprising the sequence of SEQ ID NO 15 and/or the sequence of SEQ ID NO 16, with the proviso that said polypeptide is not human CDH5, or a polypeptide comprising the sequence of SEQ ID NO: 17, with the proviso that said polypeptide is not human CDH6 nor human CDH20, mediate their therapeutic activity by preventing the interaction of the RGD motifs present in CDH17 and/or CDH5 and/or CDH6 and/or CDH20 with the α2β1 integrin, either by directly binding to the RGD motifs or by saturating the binding site of the α2β1 integrin with soluble ligands. In addition, other mechanisms may be involved in the therapeutic effect of these compounds and which would depend on the particular nature of the compound, which may include the activation of ADCC and/or CDC.

4. Methods 4.1. Methods of Diagnosis

In another aspect, the invention relates to an in vitro method for diagnosing a cancer in a subject, hereinafter referred to as "the diagnostic method of the invention", comprising:
  i) contacting the agent or the antibody construct according to the invention with a biological sample from said subject;
  ii) separating said agent or antibody construct not bound to the sample;
  iii) detecting and/or quantifying the level of said agent or antibody construct bound to CDH17 and/or CDH5 and/or CDH6 and/or CDH20 in said biological sample;

iv) comparing the presence and/or amount of said agent or antibody construct bound to CDH17 and/or CDH5 and/or CDH6 and/or CDH20 detected in step (ii) with that of a reference value; and v) correlating the result obtained with the presence of said cancer.

The terms "agent", "antibody construct", and "cancer" have been described in detail previously, and their definitions and particular and preferred embodiments are included herein by reference.

Diagnosing, as used herein, refers both to the process of attempting to determine and/or identify a possible disease in a subject, i.e. the diagnostic procedure, and to the opinion reached by this process, i.e. the diagnostic opinion. As such, it can also be regarded as an attempt at classification of an individual's condition into separate and distinct categories that allow medical decisions about treatment to be made. As will be understood by those skilled in the art, the diagnosis of a cancer, although preferred to be, need not be correct for 100% of the subjects to be diagnosed or evaluated. The term, however, requires that a statistically significant portion of subjects can be identified as suffering liver cancer. Whether a subject is statistically significant can be determined without further ado by the person skilled in the art using various well known statistic evaluation tools, e.g., determination of confidence intervals, p-value determination, Student's t-test, Mann-Whitney test, etc. Details are found in Dowdy and Wearden, Statistics for Research, John Wiley & Sons, New York 1983. Preferred confidence intervals are at least 50%, at least 60%, at least 70%, at least 80%, at least 90%, or at least 95%. The p-values are, preferably, 0.05, 0.01, 0.005 or lower.

In a first step, the diagnostic method of the invention comprises contacting the agent or the antibody construct according to the invention with a biological sample from said subject.

In a particular embodiment, the biological sample is a tumour sample or a sample containing tumour cells. In a preferred embodiment, said tumour sample or sample containing tumour cells contains CDH17 and/or CDH5 and/or CDH6 and/or CDH20.

The agent or the antibody construct according to the invention is applied to the sample in a suitable buffer to allow binding of the agent or antibody construct to CDH17 and/or CDH5 and/or CDH6 and/or CDH20 molecules that may be present in the sample. Non-limiting examples of suitable buffers to allow binding of the agent or antibody construct of the invention include PBS, TBS, phosphate buffer and citrate buffer. The amount of agent or antibody construct of the invention needed to detect CDH17 and/or CDH5 and/or CDH6 and/or CDH20 molecules present in the sample will depend on the size of the sample and the amount of CDH17 and/or CDH5 and/or CDH6 and/or CDH20 present in the same, and can be readily determined by optimisation procedures are common in the art. As an indication, the concentration of the agent or antibody construct is at least 1 fM, at least 10 fM, at least 100 fM, at least 1 pM, at least 10 pM, at least 100 pM, at least 1 nM, at least 10 nM, at least 100 nM, at least 1 μM, at least 10 μM, at least 100 μM or more. Preferably, the concentration of the agent or antibody construct is between 100 fM and 1 μM, more preferably between 1 pM and 100 nM, most preferably between 100 pM and 1 nM.

The agent or antibody construct is incubated with the sample at a suitable temperature and for a time sufficient to allow binding of the agent or antibody construct to CDH17 and/or CDH5 and/or CDH6 and/or CDH20 molecules that may be present in the sample. The temperature is preferably between 20° C. and 37° C. For example, the agent or antibody construct is incubated with the sample for at least 5 min, at least 10 minutes, at least 15 minutes at least 20 minutes, at least 30 minutes, at least 60 minutes, at least 120 min or more.

Once the agent of antibody construct of the invention is bound to the CDH17 and/or CDH5 and/or CDH6 and/or CDH20 molecules that may be present in the sample, in a second step, the diagnostic method of the invention comprises separating said agent or antibody construct not bound to the sample. This step may be carried out by any method suitable for this purpose. For example, sequential washes with a suitable buffer may be carried out on the sample.

In a third step, the diagnostic method of the invention comprises detecting and/or quantifying the level of said agent or antibody construct bound to CDH17 and/or CDH5 and/or CDH6 and/or CDH20 in said biological sample. Since the agent or antibody construct of the invention is not in itself a detectable molecule, the detection step is a step of indirect detection via a second detectable molecule that specifically binds to the agent or antibody construct. Detection of the agent or antibody construct bound to CDH17 and/or CDH5 and/or CDH6 and/or CDH20 can be carried out with virtually any antibody or reagent known to bind with high affinity to the agent or antibody construct of the invention. However, it is preferable to use a specific antibody to the agent or antibody construct, for example polyclonal sera, hybridoma supernatants, or monoclonal antibodies and fragments thereof. The antibody or reagent specific for the agent or antibody construct of the invention is suitably labelled with a detectable reagent. The term "detectable reagent" refers to reagent with capacity to be detected either directly or indirectly. Examples of detectable reagents suitable for the invention include, without limitation, radionuclides, fluorophores, and fluorescent or bioluminescent proteins, and enzymes, which are well-known in the art. This reagent may be detected by, for example, fluorimetry or colorimetry using apparatus suitable for the type of reagents and sample type, which are known to the skilled artisan.

In a particular embodiment, the detection and/or quantification of CDH17 and/or CDH5 and/or CDH6 and/or CDH20 is carried out by means of an immunoassay. In a preferred embodiment, the immunoassay is a chemiluminiscent enzyme immunoassay, more preferably a solid-phase chemiluminiscent enzyme immunoassay. Suitable immunoassays include, without limitation, Western blot, immunoprecipitation, enzyme-linked immunosorbent assay (ELISA), immunoturbidimetry, surface plasmon resonance (SPR), radioimmunoassay (RIA), chemiluminiscent enzyme immunoassay, and immunology multiplex assay.

As a result of the third step, a value of the level of the agent or antibody construct bound to CDH17 and/or CDH5 and/or CDH6 and/or CDH20 present in the sample is obtained.

In a fourth step, the diagnostic method of the invention comprises comparing the level of said agent or antibody construct bound to CDH17 and/or CDH5 and/or CDH6 and/or CDH20 detected in step (iii) with that of a reference value.

The term "reference value" refers to a predetermined criteria used as a reference for evaluating the values or data obtained from the samples collected from a subject. The reference value or reference level can be an absolute value, a relative value, a value that has an upper or a lower limit, a range of values, an average value, a median value, a mean value, or a value as compared to a particular control or baseline value. The reference value according to the diagnostic method of the invention can be obtained from the values of the level of agent or antibody construct bound to CDH17 and/or CDH5 and/or CDH6 and/or CDH20 present in a sample obtained from one or more healthy subjects or subjects who do not suffer from said cancer.

In the context of the invention, the level of agent or antibody construct bound to CDH17 and/or CDH5 and/or CDH6 and/or CDH20 is considered to be "increased" when the level of said agent or antibody construct bound to CDH17 and/or CDH5 and/or CDH6 and/or CDH20 in a sample is higher than a reference value. The level of an agent or antibody construct bound to CDH17 and/or CDH5 and/or CDH6 and/or CDH20 is considered to be higher than its reference value when it is at least 1.5%, at least 2%, at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 100%, at least 110%, at least 120%, at least 130%, at least 140%, at least 150%, or higher than its reference value.

Likewise, the level of a an agent or antibody construct bound to CDH17 and/or CDH5 and/or CDH6 and/or CDH20 is considered to be "decreased" when the level of said agent or antibody construct bound to CDH17 and/or CDH5 and/or CDH6 and/or CDH20 in a sample is lower than a reference value. The level of said agent or antibody construct bound to CDH17 and/or CDH5 and/or CDH6 and/or CDH20 is considered to be lower than its reference value when it is at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 100%, at least 110%, at least 120%, at least 130%, at least 140%, at least 150%, or lower than its reference value.

In a last step, the diagnostic method of the invention comprises correlating the result obtained with the presence of said cancer.

In a particular embodiment, an increased level of an agent or antibody construct bound to CDH17 and/or CDH5 and/or CDH6 and/or CDH20 when compared to its reference value is indicative of the presence of said cancer and/or of metastasis in said cancer.

In another particular embodiment, the biological sample is a blood, serum or plasma sample.

4.2. Methods of Prognosis

In another aspect, the invention relates to an in vitro method for prognosing a cancer in a subject, hereinafter "the prognostic method of the invention", comprising:
  i) contacting the agent or the antibody construct according to the invention with a biological sample from said subject;
  ii) separating said agent or antibody construct not bound to the sample;
  iii) detecting and/or quantifying the level of said agent or antibody construct bound to CDH17 and/or CDH5 and/or CDH6 and/or CDH20 in said biological sample;
  iv) comparing the presence and/or amount of said agent or antibody construct bound to CDH17 and/or CDH5 and/or CDH6 and/or CDH20 detected in step (ii) with that of a reference value; and
  v) correlating the result obtained with the clinical outcome of said cancer.

The terms "agent", "antibody construct", and "cancer" have been described in detail previously, and their definitions and particular and preferred embodiments are included herein by reference.

This aspect puts into practice steps (i) to (v) of the diagnostic method of the invention and thus, its definitions and particular embodiments apply equally to the prognostic method of the invention.

The term "prognosing", as used herein, refers to the determination of the likelihood that a cancer patient will have a particular clinical outcome, whether positive or negative. In the present invention "clinical outcome" is understood as the expected course of a disease. It denotes the doctor's prediction of how a subject's disease will progress, and whether there is chance of recovery, disability or mortality. The prognostic methods of the present invention can be used clinically to make treatment decisions by choosing the most appropriate treatment modalities for any particular patient. As will be understood by those skilled in the art, the prognosis of a cancer, although preferred to be, need not be correct for 100% of the subjects to be diagnosed or evaluated. The term, however, requires that a statistically significant portion of subjects can be identified as suffering liver cancer. Whether a subject is statistically significant can be determined without further ado by the person skilled in the art using various well known statistic evaluation tools, e.g., determination of confidence intervals, p-value determination, Student's t-test, Mann-Whitney test, etc. Details are found in Dowdy and Wearden, Statistics for Research, John Wiley & Sons, New York 1983. Preferred confidence intervals are at least 50%, at least 60%, at least 70%, at least 80%, at least 90%, or at least 95%. The p-values are, preferably, 0.05, 0.01, 0.005 or lower.

The term "reference value" refers to a predetermined criteria used as a reference for evaluating the values or data obtained from the samples collected from a subject. The reference value or reference level can be an absolute value, a relative value, a value that has an upper or a lower limit, a range of values, an average value, a median value, a mean value, or a value as compared to a particular control or baseline value. The reference value according to the prognostic method of the invention can be obtained from the values of the level of agent or antibody construct bound to CDH17 and/or CDH5 and/or CDH6 and/or CDH20 present in a sample or pool of samples obtained from subjects suffering from said cancer that have been classified as having a positive clinical outcome or a negative clinical outcome.

4.3. Methods of Stratification

In another aspect, the invention relates to an in vitro method for stratifying a cancer in a subject, hereinafter "the method of cancer stratification of the invention", comprising:
  i) contacting the agent or the antibody construct according to the invention with a biological sample from said subject;
  ii) separating said agent or antibody construct not bound to the sample;
  iii) detecting and/or quantifying the level of said agent or antibody construct bound to CDH17 and/or CDH5 and/or CDH6 and/or CDH20 in said biological sample;
  iv) comparing the presence and/or amount of said agent or antibody construct bound to CDH17 and/or CDH5 and/or CDH6 and/or CDH20 detected in step (ii) with that of a reference value; and
  v) correlating the result obtained with the stage of said cancer.

The terms "agent", "antibody construct", and "cancer" have been described in detail previously, and their definitions and particular and preferred embodiments are included herein by reference.

This aspect puts into practice steps (i) to (v) of the diagnostic method of the invention and thus, its definitions and particularities apply equally to the method of cancer stratification of the invention.

The term "stratifying", as used herein, refers to the determination of the extent to which a cancer has developed by spreading. A cancer may be classified according to the Overall Stage Grouping into the following stages:

Stage 0: carcinoma in situ.
Stage I: cancers are localized to one part of the body.
Stage II: cancers are locally advanced.
Stage III: cancers are also locally advanced. Whether a cancer is designated as Stage II or Stage III can depend on the specific type of cancer.
Stage IV: cancers have often metastasized, or spread to other organs or throughout the body.

As will be understood by those skilled in the art, the prognosis of a cancer, although preferred to be, need not be correct for 100% of the subjects to be diagnosed or evaluated. The term, however, requires that a statistically significant portion of subjects can be identified as suffering liver cancer. Whether a subject is statistically significant can be determined without further ado by the person skilled in the art using various well known statistic evaluation tools, e.g., determination of confidence intervals, p-value determination, Student's t-test, Mann-Whitney test, etc. Details are found in Dowdy and Wearden, Statistics for Research, John Wiley & Sons, New York 1983. Preferred confidence intervals are at least 50%, at least 60%, at least 70%, at least 80%, at least 90%, or at least 95%. The p-values are, preferably, 0.05, 0.01, 0.005 or lower.

The term "reference value" refers to a predetermined criteria used as a reference for evaluating the values or data obtained from the samples collected from a subject. The reference value or reference level can be an absolute value, a relative value, a value that has an upper or a lower limit, a range of values, an average value, a median value, a mean value, or a value as compared to a particular control or baseline value. The reference value according to the method of cancer stratification of the invention can be obtained from the values of the level of agent or antibody construct bound to CDH17 and/or CDH5 and/or CDH6 and/or CDH20 present in a sample or sample pool obtained from subjects suffering from said cancer that has been classified as Stage 0, Stage I, Stage II, Stage III, or Stage IV. The skilled person will appreciate that different reference values corresponding to the different stages may be used.

5. Pharmaceutical Compositions

In another aspect, the invention relates to a pharmaceutical composition, hereinafter "the pharmaceutical composition of the invention", comprising a therapeutically effective amount of
an agent according to the invention, or
an antibody construct according to the invention, or
a peptide according to the invention, or
a polypeptide comprising the sequence of SEQ ID NO: 14, with the proviso that said polypeptide is not human CDH17, or
a polypeptide comprising the sequence of SEQ ID NO 15 and/or the sequence of SEQ ID NO 16, with the proviso that said polypeptide is not human CDH5, or
a polypeptide comprising the sequence of SEQ ID NO: 17, with the proviso that said polypeptide is not human CDH6 nor human CDH20
together with a pharmaceutically acceptable excipient or carrier.

The terms "agent", "antibody construct", "peptide", and "polypeptide comprising the sequence of SEQ ID NO: 14 to 17 with the proviso that said polypeptide is not human CDH17, human CDH5, human CDH6 nor human CDH20, respectively" have been described in detail previously, and their definitions and particular and preferred embodiments are included herein by reference.

In a particular embodiment, the pharmaceutical composition of the invention comprises a therapeutically effective amount of the agent, antibody construct, or peptide according to the invention, or of a polypeptide comprising the sequence of SEQ ID NO: 14, with the proviso that said polypeptide is not human CDH17, a polypeptide comprising the sequence of SEQ ID NO 15 and/or the sequence of SEQ ID NO 16, with the proviso that said polypeptide is not human CDH5, or a polypeptide comprising the sequence of SEQ ID NO: 17, with the proviso that said polypeptide is not human CDH6 nor human CDH20, together with a pharmaceutically acceptable excipient, carrier, adjuvant, or vehicle, for administration to a subject. Said pharmaceutical composition can be used for killing or for inducing apoptosis of cells expressing CDH17 and/or CDH5 and/or CDH6 and/or CDH20 upon administration to a subject having a cancer wherein cells expressing CDH17 and/or CDH5 and/or CDH6 and/or CDH20 participate.

The term "therapeutically effective amount" has been described in detail in the context of the medical uses of the invention and its definition and particular embodiments are incorporated herein by reference.

The term "pharmaceutically acceptable carrier", as used herein, is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, use thereof in the compositions is contemplated. Acceptable carriers, excipients, or stabilizers are nontoxic to recipients at the dosages and concentrations employed, and include buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as TWEEN™, PLURONICS™ or polyethylene glycol (PEG).

The agent, antibody construct, or peptide according to the invention, or the polypeptide comprising the sequence of SEQ ID NO: 14, with the proviso that said polypeptide is not human CDH17, a polypeptide comprising the sequence of SEQ ID NO 15 and/or the sequence of SEQ ID NO 16, with the proviso that said polypeptide is not human CDH5, or a polypeptide comprising the sequence of SEQ ID NO: 17, with the proviso that said polypeptide is not human CDH6 nor human CDH20, may be in the same formulation or may be administered in different formulations. Administration can be concurrent or sequential, and may be effective in either order.

In an embodiment, the agent, antibody construct, or peptide according to the invention, or the polypeptide comprising the sequence of SEQ ID NO: 14, with the proviso that said polypeptide is not human CDH17, a polypeptide comprising the sequence of SEQ ID NO 15 and/or the sequence of SEQ ID NO 16, with the proviso that said polypeptide is not human CDH5, or a polypeptide comprising the sequence of SEQ ID NO: 17, with the proviso that said polypeptide is not human CDH6 nor human CDH20 is prepared with carriers that will protect said compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. These can be prepared according to methods well-known to those skilled in the art.

In another particular embodiment, the route of administration of the pharmaceutical composition of the invention is intratumoural or parenteral.

The term "parenteral" as used herein includes intravenous, intraperitoneal, intramuscular, subcutaneous, rectal or vaginal administration. The intravenous form of parenteral administration is generally preferred. In addition, the pharmaceutical composition of the invention may suitably be administered by pulse infusion, e.g., with declining doses. Preferably the dosing is given by injections, most preferably intravenous or subcutaneous injections, depending in part on whether the administration is brief or chronic.

In a preferred embodiment, the pharmaceutical compositions of the invention may be adapted for parenteral administration, such as sterile solutions, suspensions or lyophilized products in the appropriate unit dosage form. Pharmaceutical compositions suitable for injectable use include sterile aqueous solutions (where water soluble) or dispersions and sterile powders for the extemporaneous preparation of sterile injectable solutions or dispersions. For intravenous administration, suitable carriers include physiological saline, bacteriostatic water, CremophorEM (BASF, Parsippany, N.J.) or phosphate buffered saline (PBS). In all cases, the composition must be sterile and should be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, a pharmaceutically acceptable polyol like glycerol, propylene glycol, liquid polyetheylene glycol, and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, and sodium chloride in the composition. Prolonged absorption of the injectable compositions can be brought about by including in the composition an agent which delays absorption, for example, aluminum monostearate and/or gelatin. The mentioned formulations will be prepared using standard methods such as those described or referred to in the Spanish and US Pharmacopoeias and similar reference texts.

Sterile injectable solutions can be prepared by incorporating the active compound (e.g., the agent, antibody construct, peptide or polypeptide) in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

It is especially advantageous to formulate the pharmaceutical compositions, in dosage unit form for ease administration and uniformity of dosage. Dosage unit form as used herein refers to physically discrete units suited as unitary dosages for the subject to be treated; each unit containing a predetermined quantity of active compound (e.g., the agent, antibody construct, peptide or polypeptide) calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals.

Generally an effective administered amount of an antibody of the invention will depend on the relative efficacy of the compound chosen, the severity of the disorder being treated and the weight of the sufferer. However, active compounds will typically be administered once or more times a day for example 1, 2, 3 or 4 times daily, with typical total daily doses in the range of from 0.001 to 1,000 mg/kg body weight/day, preferably about 0.01 to about 100 mg/kg body weight/day, most preferably from about 0.05 to 10 mg/kg body weight/day.

The pharmaceutical compositions can be included in a container, pack, or dispenser together with instructions for administration.

6. Uses

Another aspect of the invention relates to the use of an epitope comprising residues 603 to 605 of human cadherin 17 (CDH17), and/or an epitope comprising residues 236 to 238 or residues 299 to 301 of human cadherin 5 (CDH5), and/or an epitope comprising residues 83 to 85 of human cadherin 6 (CDH6) and/or an epitope comprising residues 89 to 91 of human cadherin 20 (CDH20) as a marker of a cancer wherein cells expressing CDH17 and/or CDH5 and/or CDH6 and/or CDH20 participate, In a particular embodiment, said cancer wherein cells expressing CDH17 and/or CDH5 and/or CDH6 and/or CDH20 participate is melanoma, breast cancer, or a gastrointestinal cancer.

In a preferred embodiment, said gastrointestinal cancer is selected from the group consisting of colon cancer, pancreatic cancer, liver cancer, gastric cancer, and oesophagus carcinoma.

Another aspect of the invention relates to the use of an epitope comprising residues 603 to 605 of human cadherin 17 (CDH17), and/or an epitope comprising residues 236 to 238 or residues 299 to 301 of human cadherin 5 (CDH5), and/or an epitope comprising residues 83 to 85 of human cadherin 6 (CDH6) and/or an epitope comprising residues 89 to 91 of human cadherin 20 (CDH20) as a metastatic marker of a cancer wherein cells expressing CDH17 and/or CDH5 and/or CDH6 and/or CDH20 participate, In a particular embodiment, said cancer wherein cells expressing CDH17 and/or CDH5 and/or CDH6 and/or CDH20 participate is melanoma, breast cancer, or a gastrointestinal cancer.

In a preferred embodiment, said gastrointestinal cancer is selected from the group consisting of colon cancer, pancreatic cancer, liver cancer, gastric cancer, and oesophagus carcinoma.

Various embodiments of the invention will be illustrated by the following examples, which are to be taken to illustrate but not to limit the invention described herein.

EXAMPLES

Materials and Methods
Cell lines, Antibodies and Peptides

KM12SM human colon cancer cells were purchased directly from Dr Fidler's lab (MD Anderson Cancer Center. USA). RKO human colon cancer cells and pancreatic cancer cell lines, BxPc3, Capan-1 and PANC1 were purchased from the American Type Culture Collection (ATCC). 786-O kidney clear cell carcinoma cell line was kindly provided by M. J. Calzada (Hospital de la Princesa, Madrid, Spain). We also used as a control MCF7 breast carcinoma cell line, SK-MEL-103 and A375 melanoma cell lines. All cell lines were used within 6 months of purchase and cultured in Dulbecco's modified Eagle medium (DMEM) (Invitrogen) containing 10% fetal calf serum (FCS) (Invitrogen) and antibiotics at 37° C. in a 5% CO2-humidified atmosphere.

Antibodies anti-CDH6, anti-CDH5, anti-FAK, anti-RhoGDI, anti-α2, β1, α6, β4 and αv integrins were purchased from Santa Cruz Biotechnology. Anti-pFAK, ERK1/2, pERK1/2 and blocking anti-β1 integrin (Lia 1/2.1) were from Cell Signaling. Anti-β1 integrin specific for high affinity conformation (HUTS-21) was from BD Biosciences. Antibodies anti-CDH17 (H-167 and C-17) were purchased from Santa Cruz Biotechnology. LI-cadherin (H-167) is a rabbit polyclonal antibody raised against amino acids 666-832 mapping at the C-terminus of LI-cadherin of human origin. LI-cadherin (C-17) is an affinity purified goat polyclonal antibody raised against a peptide mapping at the C-terminus of LI-cadherin of human origin. Anti CDH17 (#141713) was from R&D systems and was obtained after immunization with the complete extracellular domain of the protein. Polyclonal and monoclonal antibodies anti CDH17 Domain6 were obtained as described below. Synthetic peptide RGDS was purchased from Sigma. Peptides RADS (SEQ ID NO: 18), SILRGDYQD (CDH5) (SEQ ID NO: 19), RAIRRGDTEG (CDH16) (SEQ ID NO: 20) and VSLRGDTRG (CDH17) (SEQ ID NO: 1) were synthesized using solid phase chemistry with a Focus XC instrument (AAPPtec).

Recombinant domains 6 of CHD7 (wt and mutant) were produced in *Escherichia coli* and purified according to standard procedures.

Cloning and Mutagenesis of CDH17, Protein Purification and Transfections

CDH17 mRNA from human colorectal cancer cell line Caco2 was reverse transcribed by Superscript III First Strand Synthesis kit (Invitrogen), and the cDNA was RT-PCR amplified using the primers: 5'-AGCTCGAGGATCT-GAGTTGATCAATCTGCTTAGTG-3' (SEQ ID NO: 21) and 5'-CGGGTACCATGAGATGGTTGTTGCTGAAAT (SEQ ID NO: 22).

AG-3' with the Advantage 2 polymerase (Clontech). PCR product was digested with XhoI and KpnI and cloned into pcDNA3.1. Mutagenesis of CDH17 to change motif 603-RGD-605 into RAD was performed with the QuickChange Lightning Site-Directed Mutagenesis Kit (Agilent Technologies), using the primers: 5'-GGACATAAGCTATTCACT-GAGGGCAGACACAAGAGGTTGG-3' (SEQ ID NO: 23) and 5'-CCAACCTCTTGTGTCTGCCCTCAGT-GAATAGCTTATGTCC-3' (SEQ ID NO: 24). The presence of the mutation was confirmed by DNA sequencing. Cells were transiently transfected with CDH17 wild type (wt) or CDH17 RAD in pcDNA3.1 using JetPrime (Polyplus Transfection). After 48 h, a fraction of the transfectants was lysed and analyzed by western blot to assess the expression of CDH17. Control siRNA and siRNA against CDH17 (SASI_Hs01_00166354) were from Sigma-Aldrich.

The recombinant ectodomains of CDH17 (wt and RAD mutant) were expressed with the baculovirus system in insect cells according to standard procedures. Recombinant domains 6 (wt and mutant) were produced in *E. coli* and purified according to standard procedures.

Reverse Transcription-PCR

For CDH6 and CDH20 amplification, cells were lysed in Trizol Reagent (Ambion). RNA was extracted and reverse transcribed using MoMLV reverse transcriptase (Promega). Amplification of CDH6 was done by PCR using primers 5'-GTCATCACCGACCAGGAAAC-3' (SEQ ID NO: 25) and 5'-TGCAGGGTCTGAATCAACTG-3' (SEQ ID NO: 26). For CDH20 the primers were 5'-AGAG-GAGCTGGGTTTGGAA-3' (SEQ ID NO: 27) and 5'-GCATCTGTGGCTGTCACTTG-3' (SEQ ID NO: 28). The PCR profile was 33 cycles of 30 s at 94° C., 30 s at 56° C. and 45 s at 72° C. with Taq DNA Polymerase (Invitrogen).

Cell Adhesion and Soluble Binding Assays

For cell adhesion, 96-well plates were coated with Matrigel (4 µL/mL) (BD Biosciences) or type IV collagen (5 pg/mL) (Sigma-Aldrich) in coating buffer (0.1 M NaHCO3 pH 8.8) for 20 h and incubated with adhesion medium (0.4% BSA in serum-free DMEM) for 2 h to block unspecific binding. Cell were starved for 5 h without serum, labeled with BCECF-AM (Invitrogen), detached with 2 mM EDTA in PBS, resuspended in serum-free DMEM and $7 \times 10^4$ cells in 100 µL were added to plates in triplicate and then incubated for 25 min. Non-adherent cells were removed by three washes with DMEM. Bound cells were quantified using a fluorescence analyzer (POLARstar Galaxy).

For soluble binding assays, cells were detached, incubated for 40 min with CDH17 ectodomain (10 µg/mL) at 37° C. in Ca2+, Mg2+ and Mn2+-free HBSS medium (Life Technologies), washed, incubated with anti-CDH17 antibodies at 4° C., washed again, incubated with secondary antibodies and analyzed by flow cytometry. For cell adhesions to CDH17 Domain 6 (2-10 µg/mL), adhesion assays in 96 wells microtiter plates were performed as above but in medium containing 1 mM MnCl2 and cells were washed gently, using a multi-channel pipette. For blocking assays, cells were pre-incubated with anti-β1 integrin (5 µg/mL) for 10 min before adhesion.

Affinity Chromatography for α2β1 Integrin

One mg of purified CDH17 Domain 6 wt was coupled to a HiTrap NHS 1 mL column (GE Healthcare). KM12SM cell extracts (20 mg) were loaded into the column, incubated for 10 min and washed with 10 mL of lysis buffer at a flow rate of 0.4 mL/min using an ÄKTA system. Elution was performed with 5 mL of 1.5 mM RGDS peptide (SEQ ID NO: 29).

Cell Separation

Magnetic beads coated with protein G (Invitrogen) were incubated with 10 μg of anti-α2 integrin for 1 h at 4° C. $4\times10^5$ RKO cells, knocked-down, or not, for α2 integrin, were resuspended in 0.5% BSA in PBS and incubated 40 min at 4° C. with the coated beads. Cells were separated magnetically and each population was subjected to western blot analysis using anti-α2 integrin antibodies to assess the efficacy of isolation.

Flow Cytometry

Cells were detached with 2 mM EDTA in PBS, incubated at 4° C. with primary antibodies (10 μg/ml) for 30 min, washed and incubated with Alexa 488 labelled-secondary antibodies (anti-mouse IgG or anti-rabbit IgG, Dako). Fluorescence was analysed in a Coulter Epics XL cytofluorometer. Mean fluorescence intensities for the indicated antibodies are shown inside each panel. As a reference, irrelevant control antibodies (anti-cadherin-11, Santa Cruz Biotechnologies) gave a mean fluorescence intensity of 0.3.

A 50 μL volume containing $2.5\times10^5$ KM12SM cells was mixed with 50 μL of the undiluted supernatant of each hybridoma clone and incubated at RT for 30 min. After incubation, the cells were washed twice with 200 μL of PBS-3% FBS, were centrifuged (4° C., at 1000×g for 10 min), and incubated in the dark at 37° C. for 30 min in the presence of 50 μL of a 1/2000 dilution of Alexa Fluor®488 goat anti-mouse IgG (H+L) (Molecular Probes, Life Technologies). Cells were washed and maintained in the dark until flow cytometry analysis. An internal control was included to monitor unspecific binding, where cells were incubated with normal BALB/c mouse serum (1:100) and analysed using the same secondary reagents and procedures.

Flow cytometry analysis was performed using FACSCalibur™ cell analyser (BD). Cell-Quest software package was used for data acquisition, storage and analysis. At least 10,000 events per sample were acquired and cells were identified on the basis of their specific forward (FSC) and side (SSC) light scattering properties. The relative fluorescence intensity (FL-1) of labelled cells from each assay was determined as the percentage of positive fluorescent cells using a single histogram chart. A marker was set on the histogram distribution of the internal control as the non-specific binding limit.

Cell Aggregation Assays $10^5$ cells were detached with 2 mM EDTA in PBS, resuspended in 100 μL of DMEM and allowed to aggregate for 30 min at 37° C. with constant shaking at 30 rpm. Total cells and cells forming aggregates were counted under microscope in 5 different fields.

Proliferation Assays

KM12SM or RKO cells were seeded at $1\times10^4$ cells/well on 96-well plates and were incubated for 24-48 h at 37° C. in DMEM with 0.5% serum, followed by 1 h incubation with Thyzolyl Blue Tretrazolium Bromide (MTT) (0.6 mg/mL) (Sigma-Aldrich). Cell proliferation was determined by absorbance at 560 nm and comparison with control cells collected at time 0.

Western Blot and Immunoprecipitation

Cells were starved for 4 h and allowed to bind to domain 6 of CDH17-coated plates for 45 min. Then, cells were detached, washed and lysed with 1% Igepal, 100 mM NaCl, 2 mM MgCl2, 10% Glycerol in 50 mM Tris-HCl containing proteases and phosphatases inhibitors. Protein extracts were separated in SDS-PAGE gels, transferred to nitrocellulose membranes and then incubated with primary antibodies (1 μg/ml) followed by incubation with either HRP-anti-mouse IgG (Thermo Scientific) or HRP-anti-rabbit IgG (Sigma-Aldrich). Reactive proteins were visualized with SuperSignal West Pico Chemiluminescent Substrate (Thermo Scientific). Densitometric analyses were carried out using Quantity One (Bio-Rad). For immunoprecipitation, cells were lysed and 500 μg of cell lysate were incubated with the indicated antibodies (5 μg/ml). The immunocomplexes were captured by adding 50 μl of protein G-sepharose beads (Sigma-Aldrich). After washing, samples were resuspended in loading buffer, boiled for 5 min, centrifuged and subsequently loaded on 10% SDS-PAGE gels for western blot analysis.

Immunohistochemistry

A total of 48 patients diagnosed and treated for pancreatic cancer in Fundación Jiménez Diaz (Madrid, Spain) between 2003 and 2013 were used for the study. Informed written consent was obtained from all participants, as required and approved by the Research Ethics Committee of the Hospital Fundación Jimenez Diaz (Madrid). Samples were fixed and stained as previously described.

In Vivo Assays

In vivo assays were performed using Swiss nude mice (Charles River). The Ethical Committee of the Consejo Superior de Investigaciones Cientificas (CSIC, Madrid, Spain) approved the protocols used for experimental work with mice. Liver homing assays were performed as previously described. Briefly, $10^6$ cells, KM12SM or RKO, transfected with vectors encoding for CDH17 wt, RAD or empty vectors (mock) were inoculated intrasplenically in mice (n=3), which were euthanized after 24 h. RNA was isolated from the mouse liver using TRIzol and retrotranscribed. The cDNA was subjected to 30-cycles of PCR with TaqDNA polymerase to amplify human GAPDH, a house-keeping gene. As loading control, amplification of murine β-actin was performed. For xenografts, tumours were induced by subcutaneous injection of $5\times10^6$ cells, KM12SM or RKO, in PBS with 0.1% glucose in nude mice (n=3). After 10 days, mice were euthanized and tumours were excised and weighed.

Statistical Analyses

Data were analysed by one-way ANOVA followed by Tukey-Kramer multiple comparison test. In both analyses the minimum acceptable level of significance was $p<0.05$.

Immunization and Preparation of Mouse Monoclonal Antibodies

Four female Balb/c mice were immunized three times intraperitoneally (ip) using as CDH17 antigen an OVA-conjugated peptide CDH17 (VSLRGDTRG) (SEQ ID NO: 1). First, 50 μg of peptide-OVA emulsified in Freund's complete adjuvant, and the next two injections with 25 μg of peptide-OVA emulsified in Freund's incomplete adjuvant. The period between each immunization was 15 days. Bleeding to determine by indirect ELISA antibody titer anti-peptide in mice was performed 5 days after the third immunization. We also performed an assessment of CIB polyclonal sera from mice immunized in activation assay beta-1 integrin, using an antibody which recognizes the high affinity form of this integrin and measured in the flow cytometer (see below).

Ten days after the first bleeding, the animal (No. 3) was selected as donor for splenocytes and received an injection of 25 µg of peptide-OVA (ip). Three days later, the spleen was removed, taking a blood sample for serum, as positive control in further assays. The cell line of mouse myeloma SP2/O-Ag-14 was chosen for the fusion. The fusion process was carried out according to the procedures described by Galfré and Milstein, and polyethylene glycol (PEG 4000) was used as fusing agent: A myeloma/splenocytes ratio of 1 was used. After fusion, cells were seeded in 96 well plates in complete selective HAT (hypoxanthine-aminopterin-thymidine) at a density of $2 \times 10^5$ cells/well. Starting at the fifth or sixth day after the fusion, clones of hybridomas secreting potential anti-peptide antibodies CDH17 could be observed. The selection of producing clones was carried out according to:

- indirect ELISA against the CDH17 protein expressed in *E. coli*
- indirect ELISA against the peptide VSLRGDTRG (SEQ ID NO: 1) coupled to BSA
- direct flow cytometry against cells KM12SM
- flow cytometry in inhibition assay Indirect ELISA Against the CDH17 RGD Peptide Coupled to BSA Maxisorp 96-well microtiter plates (Nunc) were coated by addition of 50 µL/well of a 1 µg/mL solution of CDH17 RGD peptide (VSLRGDTRG) (SEQ ID NO: 1) coupled to BSA in carbonate buffer (50 mmol/L, pH 9.6) and overnight incubation at 4° C. Coated plates were washed three times with washing buffer (PBS with 0.05% (v/v) Tween-20) and then 150 µL of 2% BSA in PBS was added to each well to reduce non-specific binding. The plate was washed three times with washing buffer and 50 µL of undiluted supernatant of each clone was added to coated wells. The plates were incubated at 37° C. for 2 h and washed three times with washing buffer. Next, 50 pL of a 1/2000 dilution of HRP conjugated goat anti-mouse IgG (Southern Biotechnology) was added to each well and plates were incubated for 1 h at room temperature. Finally, plates were washed 5 times with washing buffer and 100 µL/well of TMB substrate solution (Sigma Aldrich) was added. Colour development was stopped after 10 min by addition of 50 µL/well of $H_2SO_4$ (2N). The absorbance was measured at 450 nm.

Determination of High-Affinity Conformation Status of β1 Integrin.

RKO cells were detached with 2 mm EDTA in PBS, washed with PBS, resuspended in DMEM and incubated with a 9-amino acid peptide containing the RGD motif and the flanking sequences from cadherin 5 (SEQ ID NO: 37 for the RGD motif of domain 2 (CDH5A), and SEQ ID NO: 19 for the RGD motif of domain 3 (CDH5B)), cadherin 6 (SEQ ID NO: 38), cadherin 17 (VSLRGDTRG) (SEQ ID NO: 1), cadherin 20 (SEQ ID NO: 39), and cadherin 16 (SEQ ID NO: 31, RAIRGDTEG) for 25 min at 37° C. in presence of immune sera or control serum (diluted 1:50). After incubation, cells were subjected to flow cytometry assays using anti-β1 integrin in high-affinity conformation antibodies (Huts21, BD Pharmingen) and Alexa 488-coupled anti-mouse IgG antibodies (Abcam). Fluorescence was analysed in a Coulter Epics XL cytofluorometer. Mean fluorescence intensities for the indicated antibodies are shown inside each panel. As a reference, irrelevant control antibodies gave a mean fluorescence intensity of 0.3.

Alternatively, RKO cells were starved for 4 h, detached with EDTA 2 mM in PBS, and incubated in serum-free DMEM with 1 µg/mL of the following peptides: 9 aa peptides including the RGD motifs and the flanking sequences corresponding to the cadherin 17 (SEQ ID NO: 1) and the two motifs present in cadherin-5 (SEQ ID NO: 37 for the RGD motif of domain 2 (CDH5A), and SEQ ID: 19 for the RGD motif of domain 3 (CDH5B)), and 7 aa or 5 aa peptides with 2 aa or 1 aa respectively in each side of the RGD motif corresponding to the sequence of CDH17, SLRGDTR (SEQ ID NO: 32), and LRGDT (SEQ ID NO: 14), respectively. Simultaneously the cells were incubated to the indicated anti-CDH17 RGD monoclonal antibodies (10 µg/mL). After 40 min, cells were washed and subjected to flow cytometry assays using HUTS21 antibody, which binds to β1-integrin in high affinity conformation. Data were collected in a FACScalibur™ cytometer (BD) and represented as % of the β1-integrin activation induced by the 9 aa CDH17 RGD peptide (SEQ ID NO: 1).

Cloning of Antibody Variable Domains from Hybridoma

Anti-cadherin 17_RGD-domain hybridoma cells from clones PA383-12.4.1, PA383-25.4.1 (hybridoma cell line deposited under Accession number DSM ACC3266 on 9 Apr. 2015 at the Leibniz Institut DSMZ—Deutsche Sammlung von Mikroorganismen und Zellkulturen (DSMZ) GmbH), PA383-6.6.1 and PA383-6.5.2 were grown as monolayers at 37° C. and 5% $CO_2$ in RPMI-1640 medium with L-glutamine and sodium bicarbonate (R0883, Sigma Aldrich), supplemented with 10% foetal bovine serum (F7524, Sigma Aldrich), 50 U/ml penicillin and 50 µg/ml streptomycin (P4458, Sigma Aldrich). Hybridoma cells were collected for mRNA extraction and the isotype of each secreted monoclonal antibody (mAb) was determined from supernatants using the IsoQuick™ Kit for Mouse Monoclonal Isotyping (ISOQ5, Sigma Aldrich).

Total RNA of each hybridoma was extracted from $3 \times 10^7$ cells using TRIZOL Reagent (15596-026, Life Technologies) and chloroform (1.02445.1000, Merck), followed by centrifugation to separate the aqueous phase. The mRNA was then isolated by precipitation with 70% ethanol (1.00983.1000, Merck) and purified with RNeasy Mini Kit (74104, QIAGEN) following the manufacturer instructions. Concentration and purity of purified mRNAs was assessed with Nanodrop ND 2000 spectrophotometer (Thermo Scientific), showing valid 260/280 and 260/230 ratios. Integrity of purified mRNA from each hybridoma was confirmed by analysis with Experion™ Automated Electrophoresis System (Bio-Rad).

About 5 µg mRNA obtained from each hybridoma was added to a PCR tube containing 1 µl oligo(dT)$_{20}$ primers (18418-020, Life Technologies), 1 µl dNTPs (R0192, Thermo Scientific) and adding ultrapure water to reach an intermediate reaction volume of 13 µl. After 5 min denaturation at 65° C., 4 µl of 5× first-strand buffer, 1 µl 0.1M DTT, 1 µl RNaseOUT Ribonuclease Inhibitor (10777-019, Life Technologies) and 1 µl SuperScript™ III Reverse Transcriptase (18080-093, Life Technologies) were added to each tube for reverse transcription, reaching a final reaction volume of 20 µl, followed by 1 cycle of 5 min at 25° C., 60 min at 50° C. and 15 min at 70° C. Finally, 1 µl Ribonuclease H (18021-014, Life Technologies) was added to the tube and the reaction was incubated 20 min at 37° C. One microliter of each reaction was analysed by agarose gel electrophoresis.

Several commercial Taq DNA polymerases (Life Technologies) were successfully used for amplifications of VH and VL. For amplification of VL from hybridomas either λ or κ primers were chosen according to the isotype (Krebber et al., 1997. Immunol Methods 201:35-55). PCR reactions were performed in 20 µl volumes, containing 1 µl of cDNA reaction, 0.8 µl of VL_Back and 0.8 µl of VL_For primer mixes for amplification of VL or 0.8 µl of VH_Back and 0.8 µl of VH_For primer mixes for amplification of VH, 2 µl dNTPs (2 mM), 0.5 µl of MgCl2 (25 mM), 4 µl betaine and 2 µl reaction buffer 10× supplied by the manufacturers.

After 3 min denaturation at 94° C., 0.15 µl of KOD (2.5 units/µl) DNA polymerase (71085-3, Novagen) were added, followed by 32 cycles of 30 sec at 94° C., 30 sec at 50° C., 1 min at 72° C., and 1 cycle of 7 min at 72° C. One microliters of each PCR reaction was analyzed by agarose gel electrophoresis. The amplification of VH and VL from hybridoma PA383-25.4.1 deposited under Accession number DSM ACC3266 on 9 Apr. 2015 at the Leibniz Institut DSMZ—Deutsche Sammlung von. Mikroorganismen and Zellkulturen (DSMZ) GmbH, was not possible.

The full length PCR products of VL and VH were purified by preparative agarose gel electrophoresis in combination with the GeneJET™ Gel Extraction Kit (K0691, Thermo Scientific), following manufacturer's instructions.

The gel-purified VL and VH fragments were separately cloned into pGEM®-T Easy Vector System II (A1380, Promega) following manufacturer's instructions and transformed into E. coli JM109™ Competent Cells (A1380, Promega). Colony analysis was performed by PCR reaction.

PCR positive colonies were cultured and grown in luria broth media (1551, Pronadisa) containing ampicillin (A9518, Sigma Aldrich) followed by plasmidic DNA extraction using GeneJET™ Plasmid Miniprep Kit (K0503, Thermo Scientific) according to manufacturer's instructions. The nucleic acid sequences were determined by sequencing using the ABI Prism Big Dye™ Terminator system and the ABI 3730 multicapillary DNA analyzer (Applied Biosystems). Geospiza's FinchTV software was used to view and analyze DNA sequences on Windows.

Expression of CDH5 in Melanoma and Breast Cancer Cell Lines

The indicated human cell lines from breast cancer (MCF7, SKBR3, MDA-MB-231, MDA-MB-468) or melanoma (MeWo, Me157, SK-MEL-28, SK-MEL-103, SK-MEL-147, A373, BLM), as well as immortalized melanocytes (Mel STV), were lysed, and 50 µg of the extracts were resolved by PAGE-SDS and subjected to western blotting using anti-CDH5 antibodies. The same blots were subjected to reprobing and incubated with anti-αTubulin antibodies to assess total amount of protein.

Example 1

Human CDH17 Sequence Contains an RGD Motif

After revising the sequence of 31 human cadherin genes, an RGD motif was found in an extracellular domain of CDH17 and CDH16. Other cadherins containing RGD motifs were VE-cadherin (CDH5), fetal kidney K-cadherin (CDH6) and CDH20. All of them are classified as Type II atypical cadherins. The RGD motif was present in domain 6 of CDH17 and domain 5 of CDH16 (FIG. 1A). Analysis of CDH17 orthologous showed that the RGD motif in CDH17 was exclusively present in some mammals (data not shown). For instance, mouse CDH17 does not contain RGD motif. Flanking sequences of RGD (FIG. 1A) are different from other reported consensus sequences for integrin ligands like fibronectin. To discard additional cadherins in our colon cancer cells, we tested the expression of other RGD cadherins either by western blot or PCR. RKO and KM12SM cells did not express CDH6, CDH16 or CDH20. CDH5 was barely detected in KM12SM cells but not in RKO cells (FIG. 1B). Breast, kidney and melanoma cancer cells were used as positive controls.

The structure of CDH17 is unknown, but the RGD motif is predicted to be exposed using two different bioinformatic approaches. According to Jpred 3 (Cole et al., 2008, Nucl Acids Res 36:W197-201), CDH17 domain 6 matched most significantly with the known structure of CDH1 domain 2. The alignment of both domains showed that the RGD motif matched exposed WRD residues (372-374) in CDH1. Accordingly, NetSurfP software (Petersen et al., 2009, BMC Struct Biol 9:51), which calculates the surface accessibility of protein residues, predicted an exposition of the RGD motif in CDH17. These predictions suggest the accessibility of the RGD motif for protein-protein interactions.

Example 2

Figure 2:
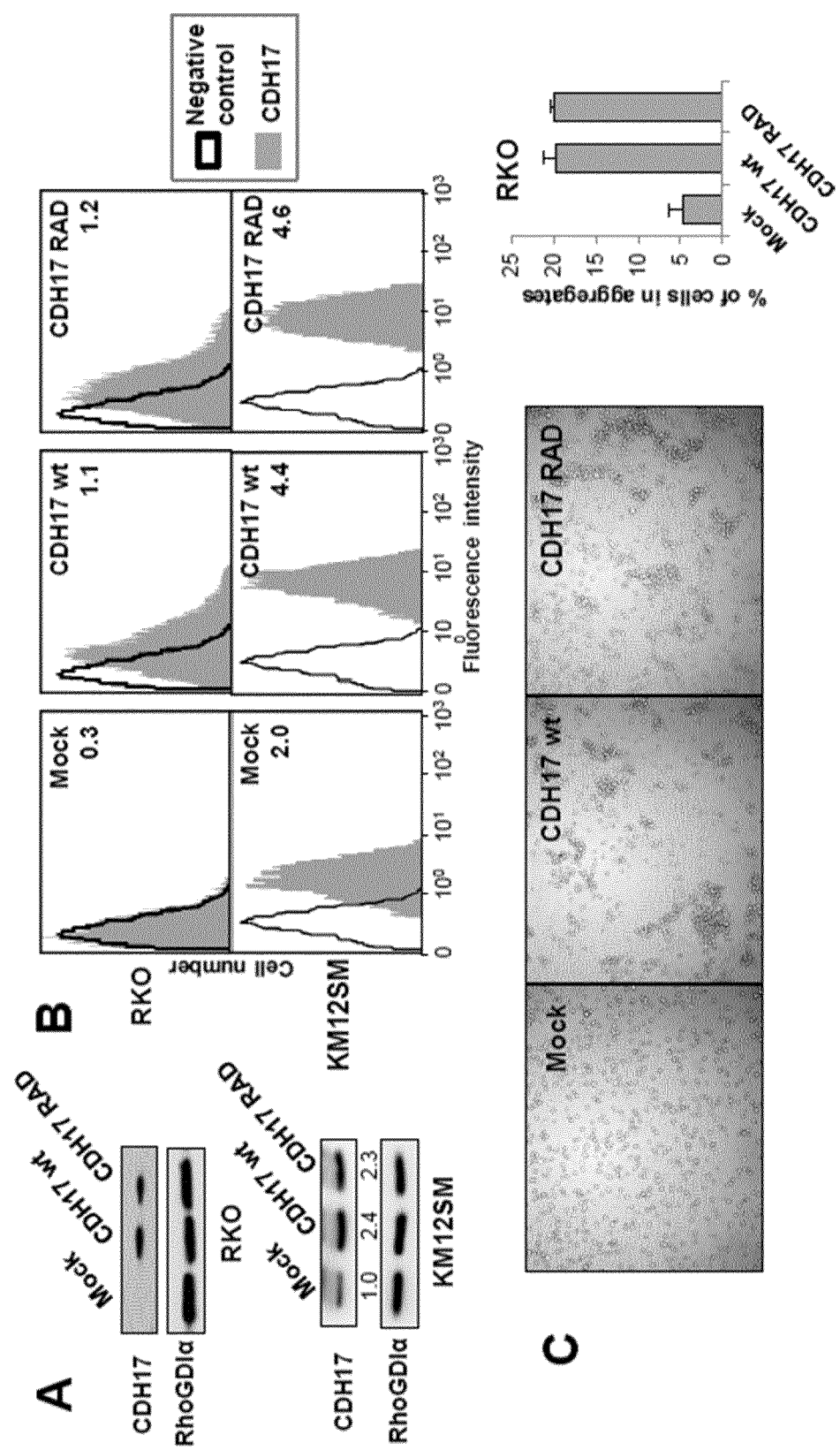
FIG. 2. The presence of CDH17 RGD is required for the increase in cell adhesion and proliferation. (A, B) RKO and KM12SM cells were transfected with vectors encoding for CDH17-wild type (CDH17 wt), a mutant form (CDH17 RAD) or empty vectors (Mock). Transfectants were analyzed by western blot (A) or by flow cytometry (B) to assess the expression of CDH17 in whole lysate and in cell membrane, respectively. (C) RKO transfectants were subjected to cell aggregation assays. Representative pictures and a quantification of cell forming aggregates are shown. (D) Transfectants were subjected to cell adhesion assays on collagen type IV or Matrigel. Adhesion was significantly enhanced by overexpression of CDH17 wild type or decreased by silencing of endogenous CDH17 (, $p<0.01$; *, $p<0.001$). (E) KM12SM transfectants were subjected to cell adhesion assays to Matrigel. Cell adhesion was significantly inhibited by silencing of the indicated proteins, *$p<0.001$). (F) RKO and KM12SM were transfected with siRNAs for the indicated integrin subunits or with a control siRNA. After 48 h, transfectants were lysed, and the extracts analyzed by immunoblotting to assess the interference in the expression. Anti-RhoGDI was used as loading control. (G) Transfectants were incubated in 0.5% serum for 48 h and subjected to MTT assays. Cell proliferation was significantly increased by overexpression of CDH17 wt (, $p<0.01$).
Figure 2:
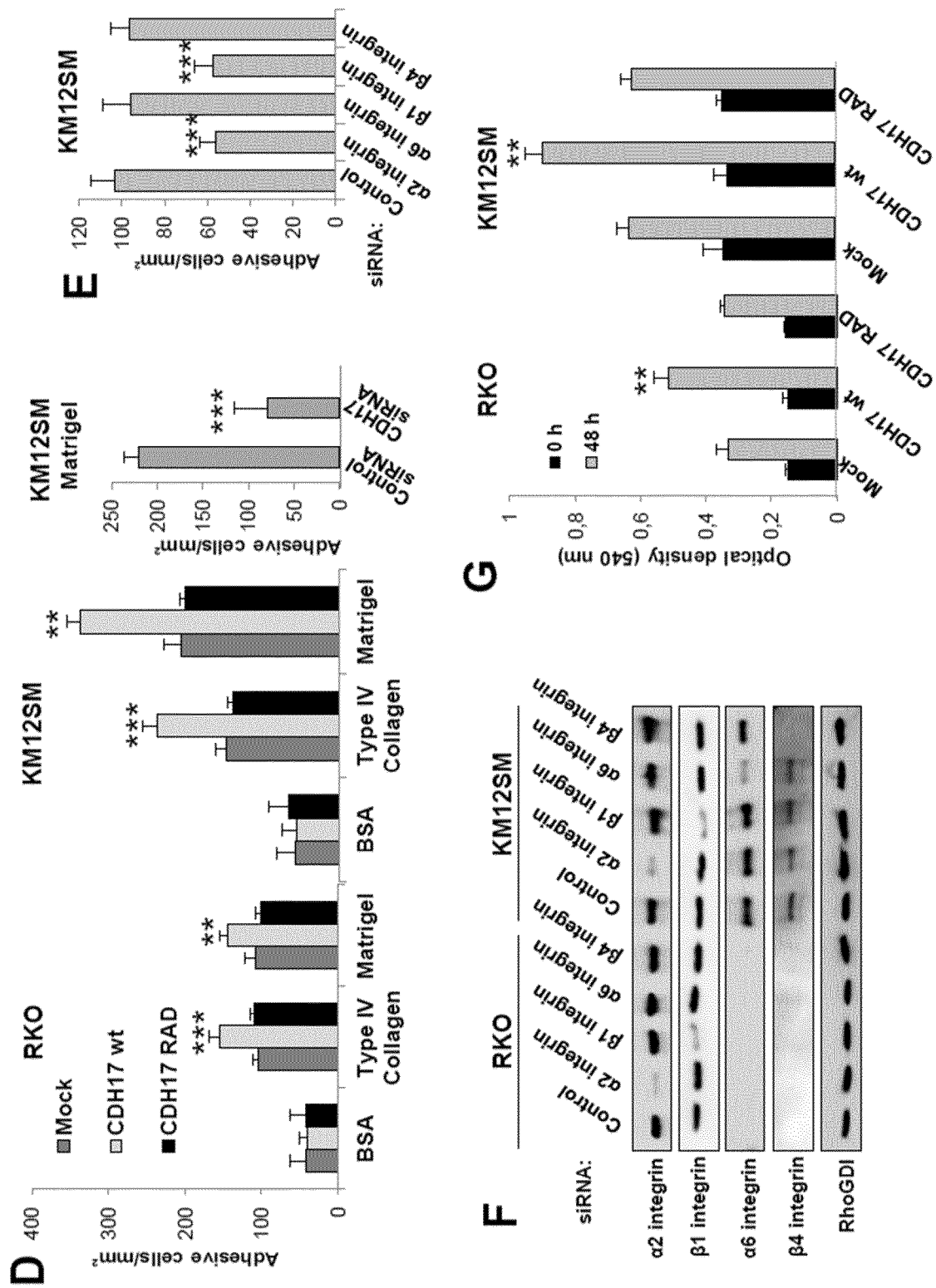

Mutation of RGD in CDH17 Reduces Adhesion and Proliferation in Colorectal Cancer Cells but does not Affect Aggregation To examine the effect of the RGD motif on colorectal cancer cells, vectors encoding for wild type CDH17 (CDH17-wt) or a RAD mutant (CDH17-RAD) were used to transfect KM12SM and RKO human colorectal cancer cells. Poorly-differentiated RKO cells are non-metastatic cells that do not express CDH17, whereas KM12SM are highly-metastatic colon cancer cells expressing CDH17. After transfection, wild-type and RAD mutant CDH17 were over-expressed in both cell lines at similar levels, as detected by western blot and flow cytometry (FIG. 2A, B). First, we tested the aggregation of cells expressing CDH17. RKO CDH17 transfectants showed a significant increase in cell aggregation respect to mock cells after detachment (FIG. 2C). This increase was RGD-independent, as CDH17 RAD transfectants showed the same increase in aggregation. This result suggests a homotypic aggregation capacity for CDH17, as described for other cadherins.

Then, we assessed the capacity of the transfectants for cell adhesion to Matrigel or Collagen Type IV. Overexpression of CDH17-wt in both cell lines increased the adhesion to both types of extracellular matrix (FIG. 2D). In contrast, CDH17-RAD transfectants showed a basal adhesion, as mock transfectants, suggesting that the RGD motif was necessary to increase cell adhesion. Also, CDH17 silencing reduced significantly the adhesion of KM12SM cells (FIG. 2D). Cell adhesion required α2β1 integrin but not α6β4 integrin, as demonstrated by using siRNAs against each integrin subunit in adhesion assays with KM12SM cells (FIG. 2E, F). Finally, cells expressing CDH17-wt showed a significant increase in proliferation, whereas the CDH17-RAD mutant was unable to increase cell proliferation (FIG. 2G). Collectively, these data indicate that the presence of the RGD motif increased cell adhesion and proliferation in colon cancer cells through α2β1 integrin, but does not affect homotypic aggregation.

Example 3

CDH17 RGD Binding Motif is a Ligand for α2β1 Integrin

Figure 3:
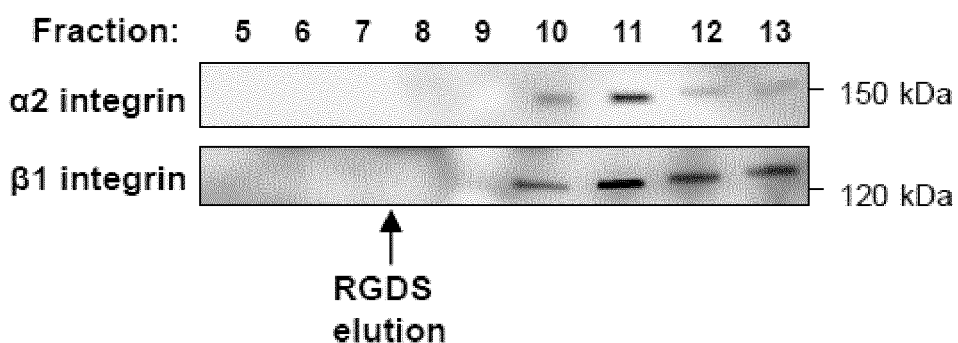
FIG. 3. The CDH17 RGD motif is a ligand of $\alpha2\beta1$ integrin. (A) Binding of $\alpha2\beta1$ integrin to immobilized CDH17 DOM6 wt. KM12SM cells were lysed and loaded onto a 1 mL column of CDH17 DOM6 wt coupled to agarose. After extensive washing, the column was eluted with RGDS peptide. The fractions (1 mL) were precipitated and subjected to western blot using anti-$\alpha2$ and anti-$\beta1$ integrin antibodies. RGDS elution started at fraction number 7. (B) RKO cells transfected with vectors encoding for CDH17 wt, CDH17 RAD or empty vectors (Mock) were lysed, subjected to immunoprecipitation with anti-$\alpha2$ integrin or anti-CDH17 antibodies and analyzed by western blot with the indicated antibodies. (C) Expression of $\alpha v$ integrin in RKO and KM12SM cells, detected by western blot (left) and immunoprecipitation assays with anti-$\alpha v$ integrin, anti- CDH17 or control antibodies, showing the lack of association between this integrin subunit and CDH17 (right). (D) Polyacrylamide gels stained with Coomasie blue showing the expression of purified ectodomain (Ecd, left) or of purified domain 6 (DOM6, right) of CDH17 both wild type (wt) or mutant lacking RGD motif (RAD). (E) Soluble binding assays using CDH17 ectodomain as ligand. Flow cytometry showed that after incubation with the wild type ectodomain, this protein fragment was bound to the cell surface. Mean fluorescence intensity is indicated in each panel. (F) Soluble binding assays using CDH17 ectodomain as ligand in cells silenced for the indicated integrin subunits. Mean fluorescence intensity is indicated for both CDH17 Ecd wt and RAD.
Figure 3:
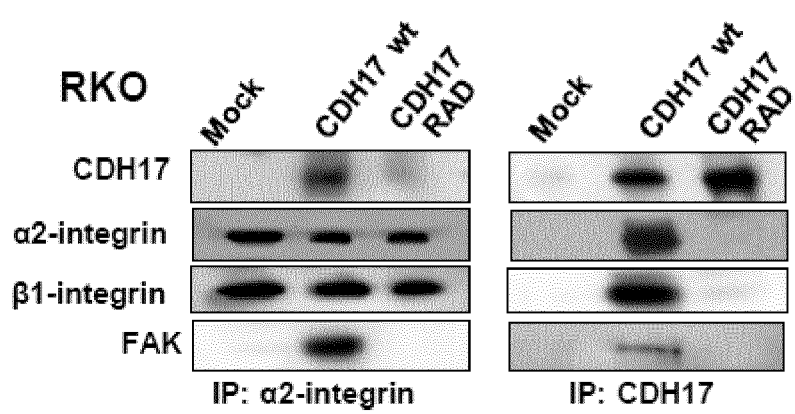
Figure 3:
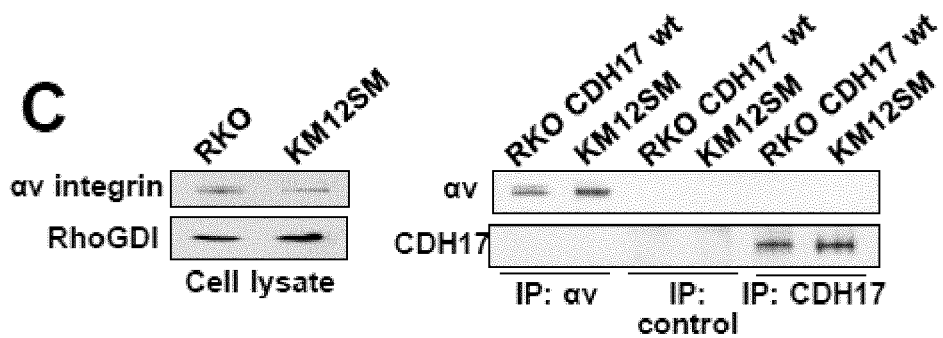
Figure 3:
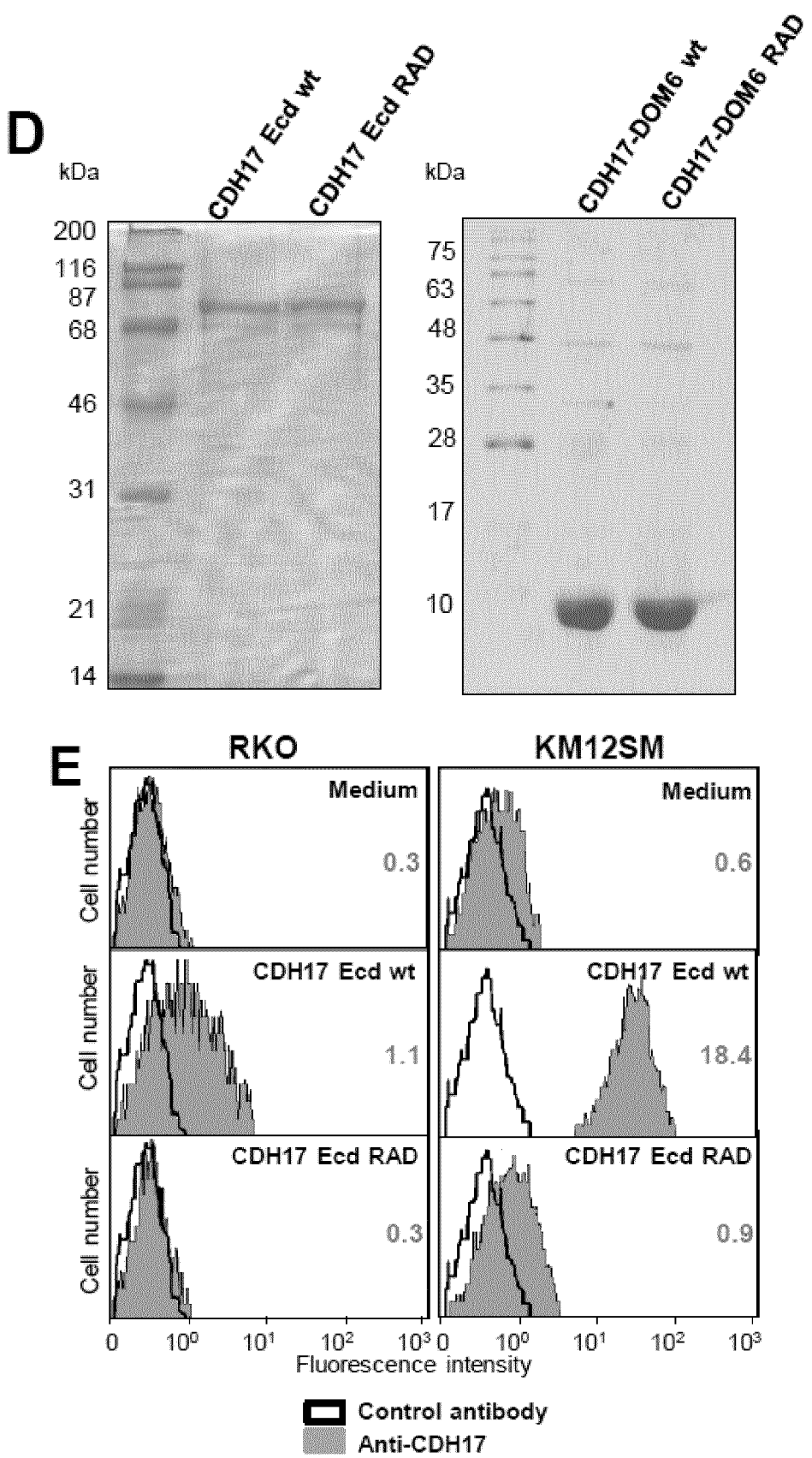
Figure 3:
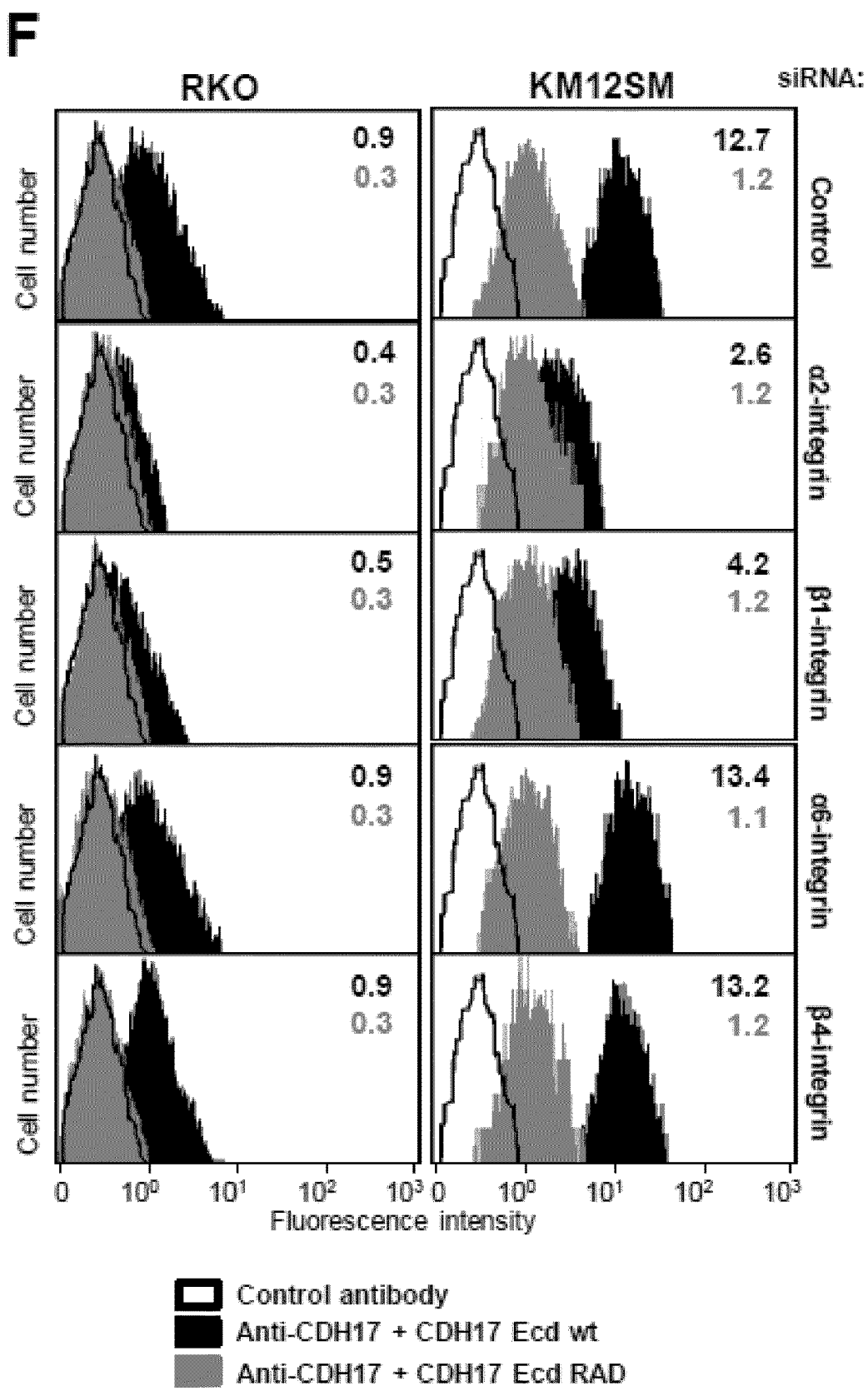

Previously, we showed that CDH17 and α2β1 integrin co-immunoprecipitated together. To prove a direct interaction, we decided to purify α2β1 integrin using affinity chromatography based on the coupling of CDH17 domain 6 wt to Sepharose. KM12SM lysates were loaded on the affinity column, washed extensively and the column eluted with an RGDS peptide. Both α2β1 integrin subunits were detected by western blot in the eluted fractions, confirming the integrin binding to CDH17 and the role of the RGD motif in that binding (FIG. 3A). To confirm that this association was RGD-dependent, CDH17 was co-immunoprecipitated with α2β1 integrin in RKO cells, after transfection with CDH17-wt. In contrast, transfected CDH17-RAD was not detected after immunoprecipitation with a2 integrin and vice versa in RKO (FIG. 3B). The α2β1 integrin was associated with FAK when CDH17-RGD wt was present, but not after RAD mutation. Therefore, in order to start signaling, the binding of the RGD motif was critical for the integrin-FAK association. To discard αv integrin, we carried out further co-immunoprecipitations. We did not detect αv integrin in CDH17-coimmunoprecipitates and vice versa (FIG. 3C).

To evaluate if exogenous CDH17 could be a ligand of integrins we used: i) the purified recombinant CDH17 ectodomain expressed in baculovirus and ii) the recombinant CDH17 domain 6 (571-665) expressed in E. coli. In addition, we prepared RAD mutants of the ectodomain and domain 6 (FIG. 3D). After incubation, the CDH17 ectodomain bound to the cell surface (FIG. 3E). However, the RAD mutant form of the CDH17 ectodomain was unable to bind to cells. To confirm that this binding was specific for α2β1 integrin, we silenced the expression of the α2β1 and α6β4 integrins using siRNAs (FIG. 2D). In both types of cells, RKO and KM12SM, the silencing of α2β1 integrin subunits inhibited the binding of CDH17-RGD ectodomain. However, the silencing of α6β4 integrin subunits did not affect the ability of the CDH17 ectodomain to bind the cell surface (FIG. 3F).

Figure 4:
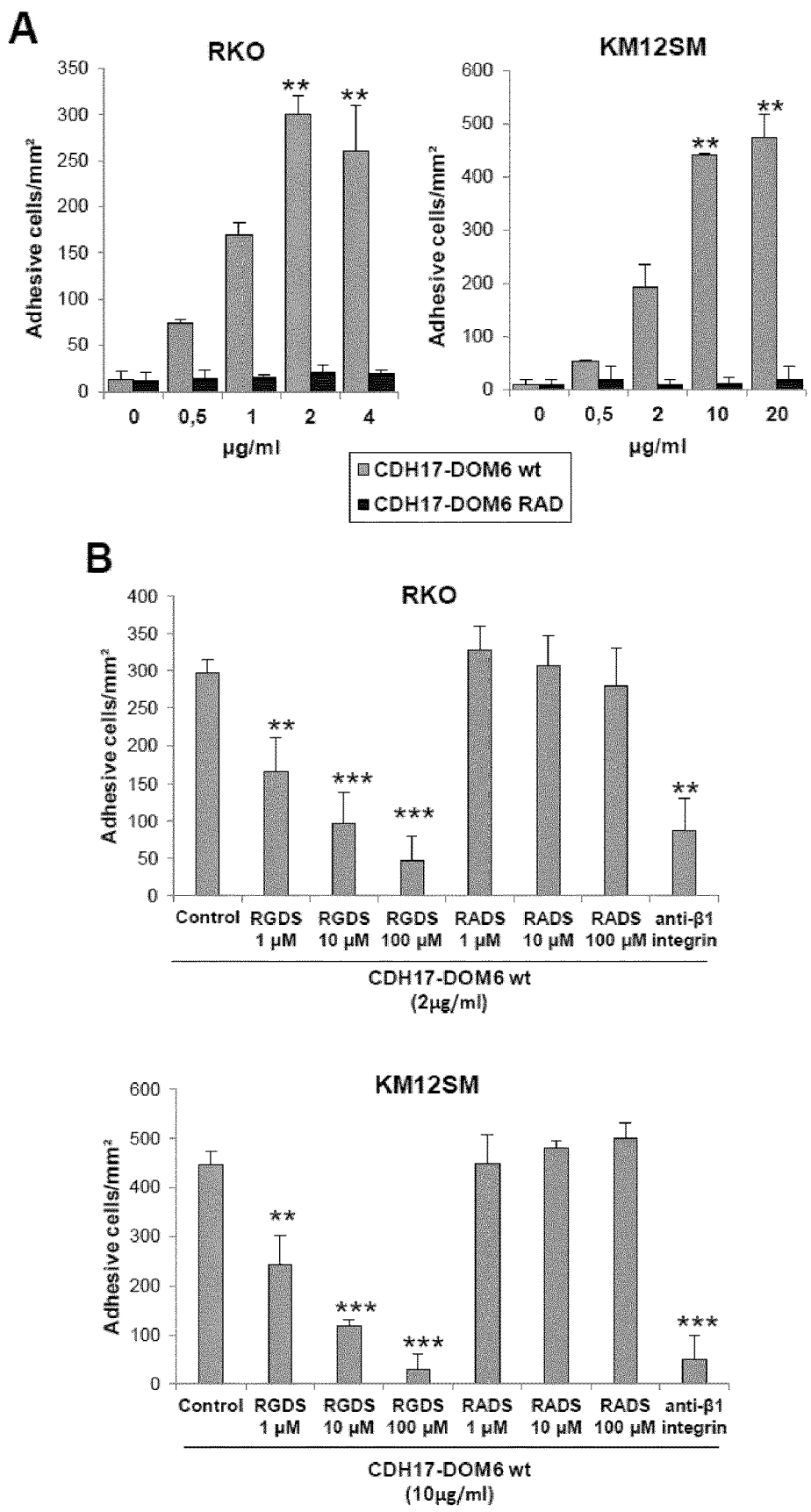
FIG. 4. The CDH17 RGD motif is able to mediate cell adhesion. (A) RKO and KM12SM cells were subjected to cell adhesion assays in plates coated with different concentrations of CDH17-DOM6 wt or CDH17-DOM6 RAD in presence of 1 mM MnCl2. Adhesion was significantly increased in plates coated with CDH17-DOM6 wt compared to plates not coated, or coated with CDH17-DOM6-RAD (**, $p<0.01$). (B) Cell adhesion assays to CDH17 DOM6 wt were done in the presence of the RGDS, RADS peptides or anti-β1 integrin blocking antibodies. Adhesion was significantly inhibited by the addition of peptides or antibodies (*, $p<0.05$; , $p<0.01$; *, $p<0.001$). (C) Cell adhesion assays to CDH17 DOM6 wt with cells silenced for the indicated integrin subunits. Adhesion was significantly inhibited by the silencing of the indicated integrin subunits (, $p<0.01$; *, $p<0.001$).
Figure 4:
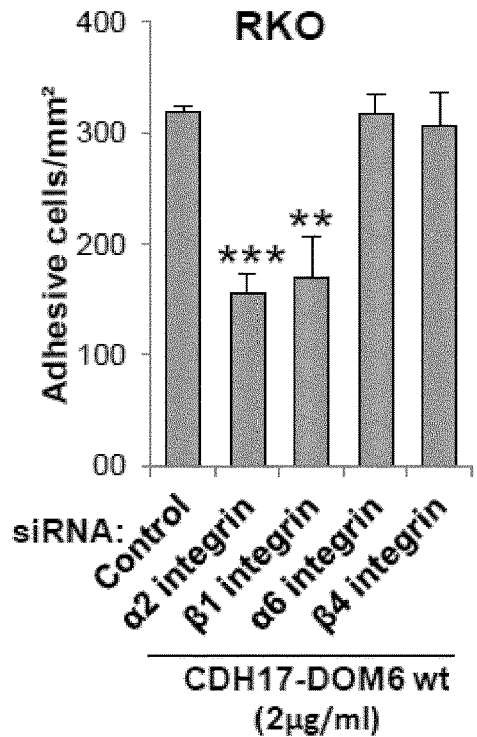
Figure 4:
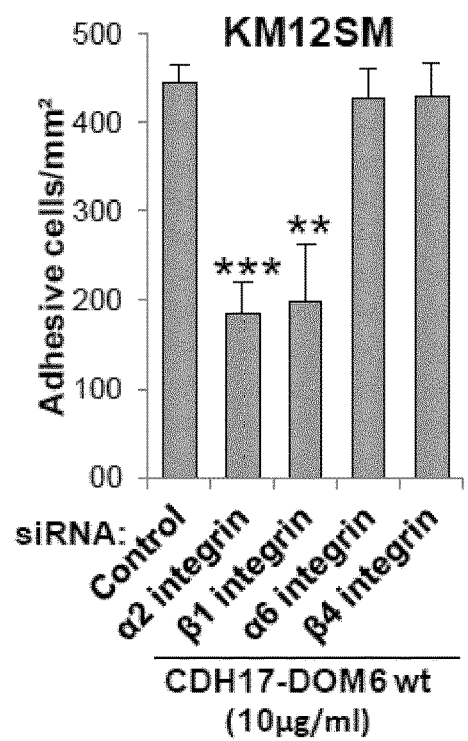

Then, we tested recombinant domain 6 as a ligand on cell adhesion assays. We found that 2 and 10 µg/mL were the optimal doses in RKO and KM12SM, respectively, for promoting cell adhesion to plates coated with domain 6 (FIG. 4A). Moreover, there was a clear dose-dependent effect of the RGDS peptide to inhibit cell adhesion to CDH17 domain 6 wt in both cell lines. The competition started at 1 µM and was similar to that obtained with a blocking antibody anti-β1 integrin (FIG. 4B). In contrast, the RADS peptide did not inhibit cell adhesion (FIG. 4B). This result suggests that the CDH17 domain 6 mediates cell adhesion in a RGD-dependent manner. Again, to confirm that the binding was integrin-dependent, we silenced the expression of the four integrin subunits. Only silencing of α2β1 integrin inhibited significantly the cell adhesion to CDH17 domain 6 (FIG. 4C).

Example 4

Role of the RGD Motif in β1 Integrin Activation

Figure 5:
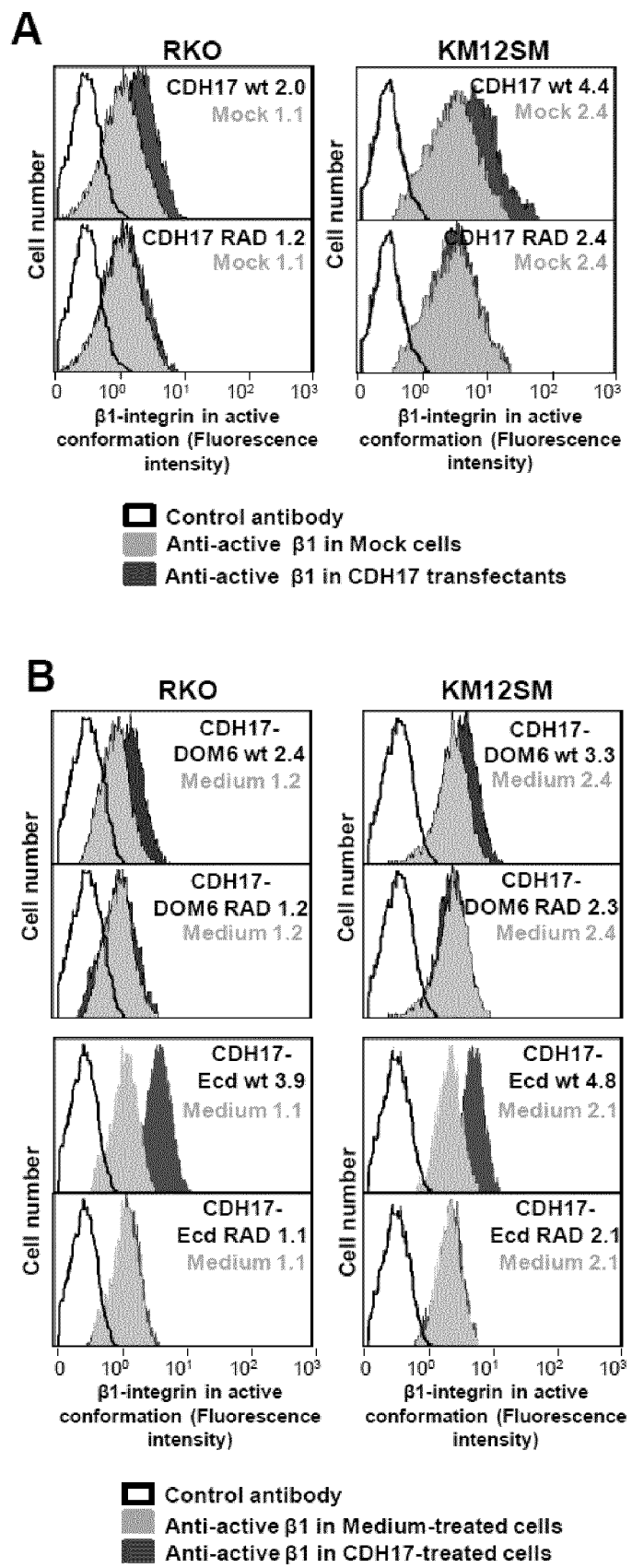
FIG. 5. RGD enhances β1 integrin activation and cell adhesion to Matrigel. (A) RKO and KM12SM cells were transfected with vectors coding to CDH17 wt or RAD or with empty vectors (mock) and subjected to flow cytometry assays with HUTS21 antibody, which recognizes β1 integrin in high affinity conformation, or with a control antibody. Inside each panel, mean fluorescence intensity is showed. (B) RKO and KM12SM cells were exposed to CDH17 DOM6 (2 μg/mL) or Ecd (10 μg/mL) (wt or RAD) or medium for 45 min and subjected to flow cytometry assays with HUTS21 antibody or a control antibody as in A. (C) RKO and KM12SM cells were exposed to 9 amino acid peptides (0.5 μg/mL) whose sequences include the RGD motif and flanking amino acids belonging to CDH5, CDH16 and CDH17, for 45 min and subjected to flow cytometry as in A. (D) After incubation with CDH17 DOM6 or Ecd (wt or RAD), cells were collected and subjected to cell adhesion assays to Matrigel. Adhesion was significantly enhanced by incubation with CDH17 DOM6 wt or Ecd RAD (, $p<0.01$; *, $p<0.001$).
Figure 5:
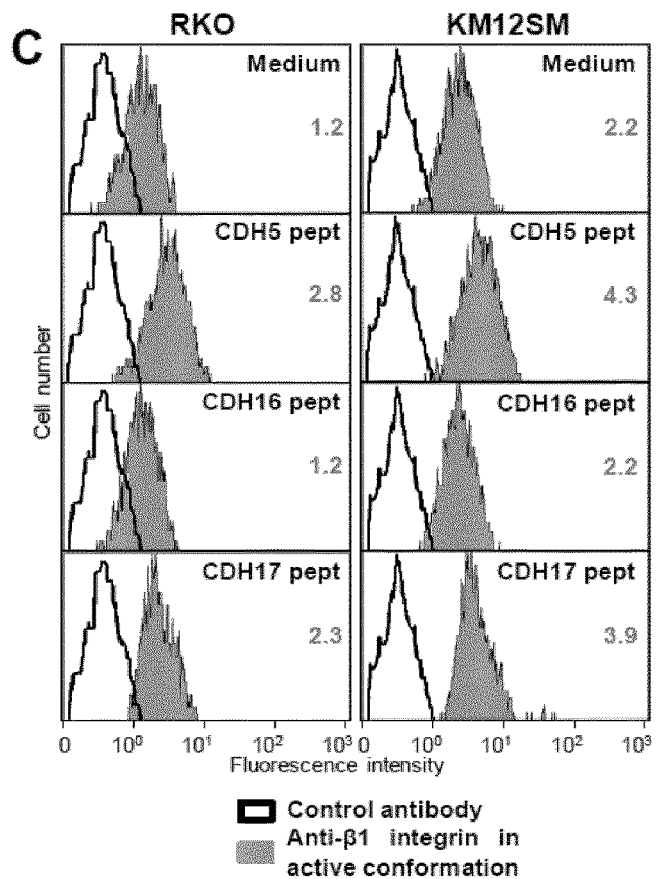
Figure 5:
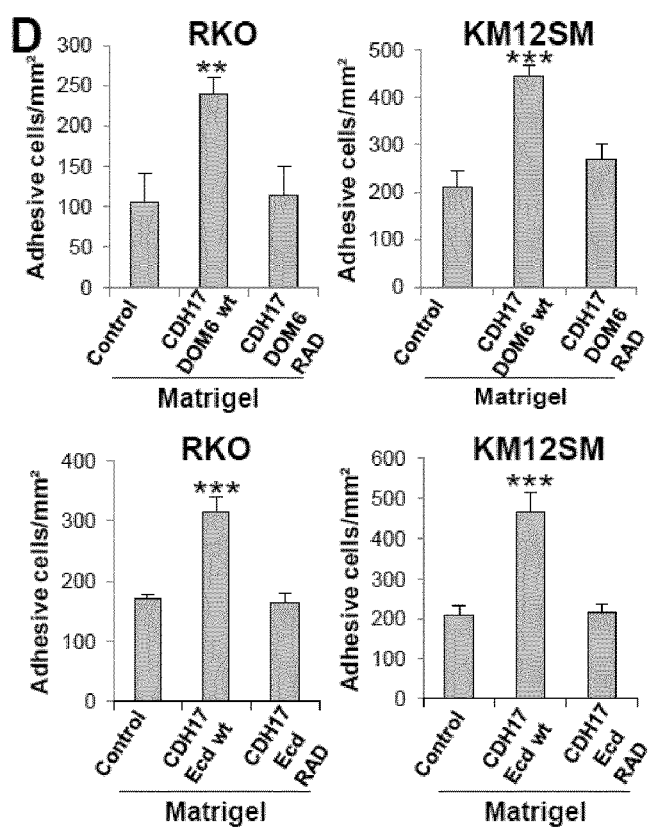

To assess the role of the RGD motif in integrin activation, we transfected both cell lines with vectors containing CDH17 wt and the RAD mutant. Expression of α2β1 integrin was not affected by altering CDH17 expression levels in colorectal cancer cells. However, CDH17-wt increased the high-affinity conformation of β1 integrin in RKO and KM12SM cells, as shown by using the HUTS21 antibody, which specifically recognizes this conformation (FIG. 5A). In contrast, cells transfected with CDH17-RAD showed similar amounts of high-affinity conformation β1 integrin than mock cells (FIG. 5A). Therefore, the RGD motif in CDH17 provoked the change to high-affinity conformation required for β1 integrin activation. In the same way, preincubation with CDH17 ectodomain or domain 6 wt enhanced the amount of β1 integrin in high-affinity conformation, while incubation with the RAD mutants had no effect (FIG. 5B). In addition, we tested the effect of the RGD flanking sequences on integrin activation. Besides CDH17 peptide, we tested CDH16 and CDH5 RGD flanking sequences. Exposition to the CDH17 peptide increased high-affinity conformation β1 integrin in both cell lines (FIG. 5C). A similar effect was observed when cells were exposed to the CDH5 RGD peptide (FIG. 5C). In contrast, CDH16 RGD had no effect on β1 integrin activation (FIG. 5C). These results confirm the relevance of the RGD flanking sequences on β1 integrin activation.

Finally, we assess if the change to high-affinity conformation of β1 integrin increased the adhesive capacity of the cells. CDH17 ectodomain and domain 6 wt caused a significant increase in cell adhesion to Matrigel, whereas the RAD mutant hardly increased the basal levels (FIG. 5D).

Example 5

The CDH17 RGD Motif is Critical for Tumour Growth and Metastasis

Figure 6:
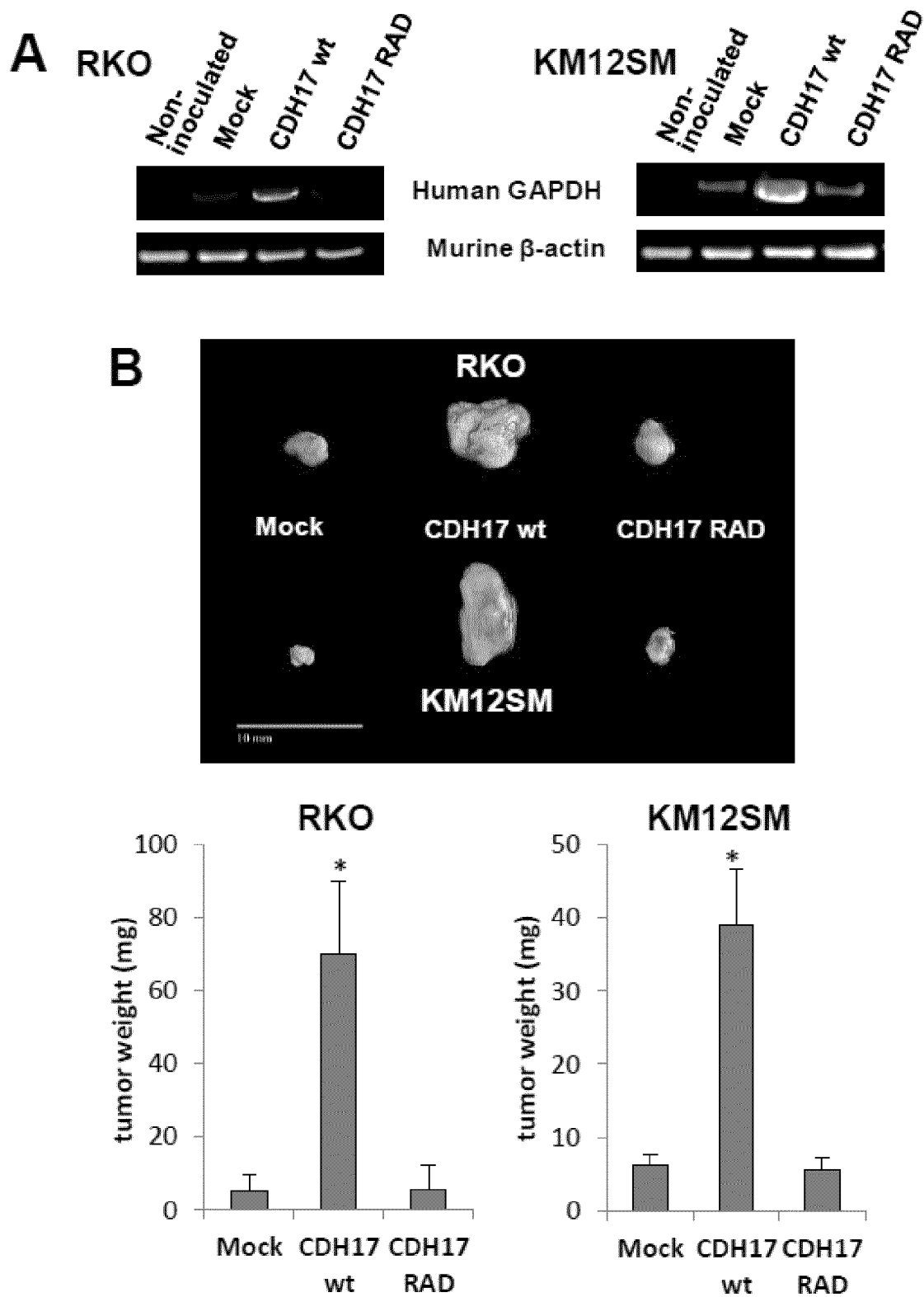
FIG. 6. RGD motif is critical for tumor growth and metastatic dissemination. (A) Swiss nude mice were inoculated intrasplenically with RKO or KM12SM cells transfected with vectors encoding for CDH17 wt, CDH17 RAD or empty vectors (Mock). Human GAPDH was RT-PCR amplified from RNA isolated from the livers 24 h after inoculation. Amplification of murine β-actin was used as a control. (B) The same transfectants were inoculated subcutaneously. (Top) Representative picture of tumors developed after 10 days. (Bottom) Tumor weight after 10 days was significantly increased in cells expressing CDH17 wt (*, $p<0.05$).

We carried out subcutaneous and intra-splenic inoculations of Swiss nude mice with RKO and KM12 cells containing CDH17 wt or mutant RAD by triplicate. Mice were sacrificed 24 h after intrasplenic injection of cells and livers collected for DNA extraction and PCR analysis (FIG. 6A). Liver DNA from mice inoculated with CDH17-RGD cells was positive by PCR using human GAPDH primers. In contrast, mice inoculated with CDH17-RAD mutant cells showed negligible DNA amplification in liver. After subcutaneous inoculation, CDH17 wt cells developed considerable tumours. In contrast, cells containing RAD mutants showed very small tumours, similar to control mock (FIG. 6B). Tumour weight corroborated these differences between CDH17-RGD and RAD cells (FIG. 6B). These results support a critical role for the RGD motif in the tumour growth and metastatic dissemination in colon cancer.

Example 6

The CDH17 RGD Motif is Relevant in Pancreatic Cancer Cells

Figure 7:
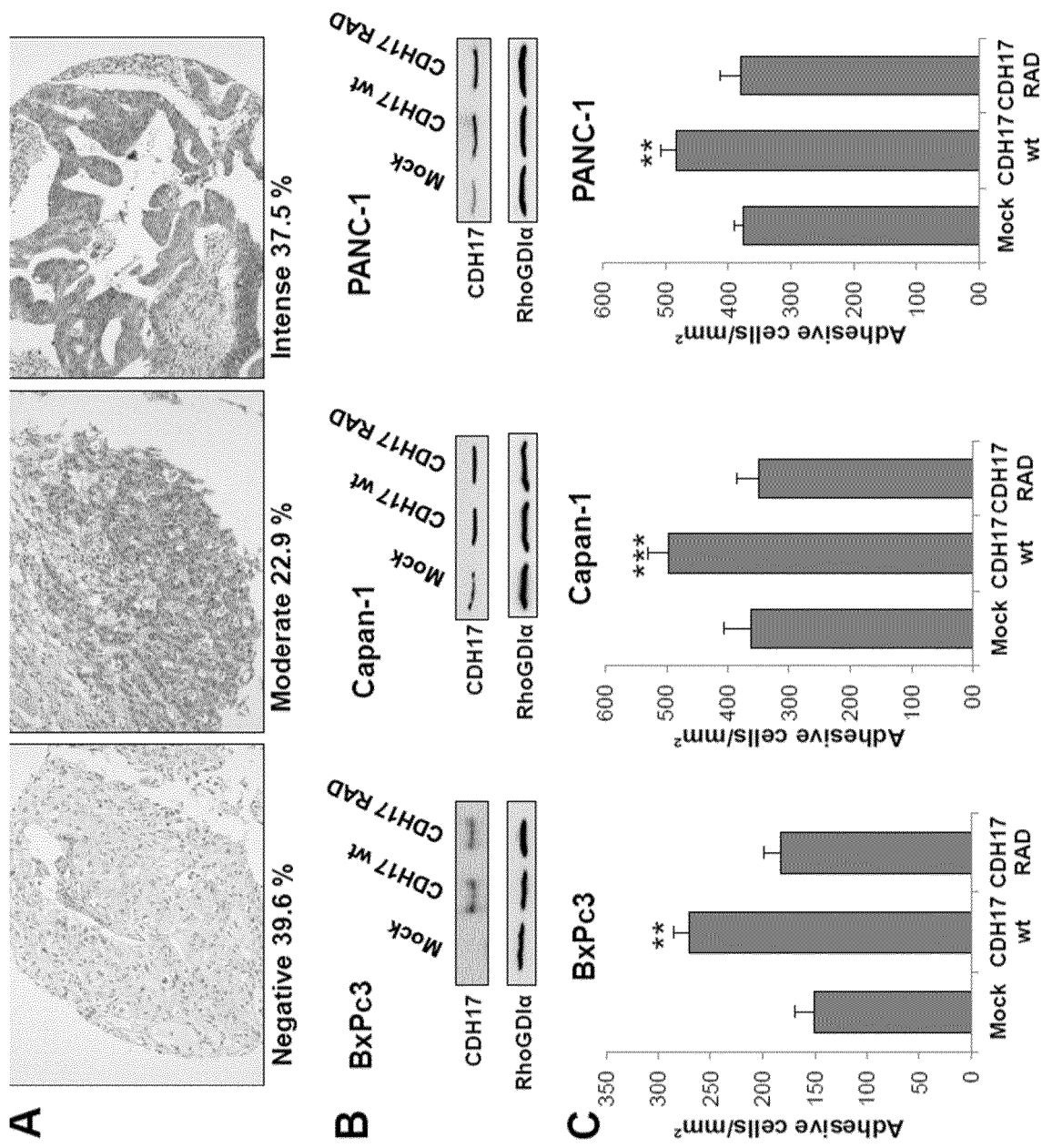
FIG. 7. CDH17 expression promotes cell adhesion and proliferation in pancreatic cancer cells. (A) Immunohistochemistry analysis of CDH17 expression in human pancreatic cancer samples (n=48), showing representative images of strong, moderate, or negative staining, and the percentage in each classification. (B) BxPc3, Capan-1 and PANC-1 were transfected with vectors encoding for CDH17 wt, CDH17 RAD or empty vectors (Mock). Transfectants were lysed and the extracts subjected to western blot analysis to confirm the overexpression of CDH17. (C) Transfectants were subjected to cell adhesion assays to Matrigel. Adhesion was significantly enhanced by overexpression of CDH17 wt (, $p<0.01$; *, $p<0.001$). (D) Transfectants were incubated in 0.5% serum for 24 h and subjected to MTT assays. Cell proliferation was significantly increased by overexpression of CDH17 wt (, $p<0.01$; *, $p<0.001$). As a control, a fraction of the cells was subjected to MTT assays at time 0.
Figure 7:
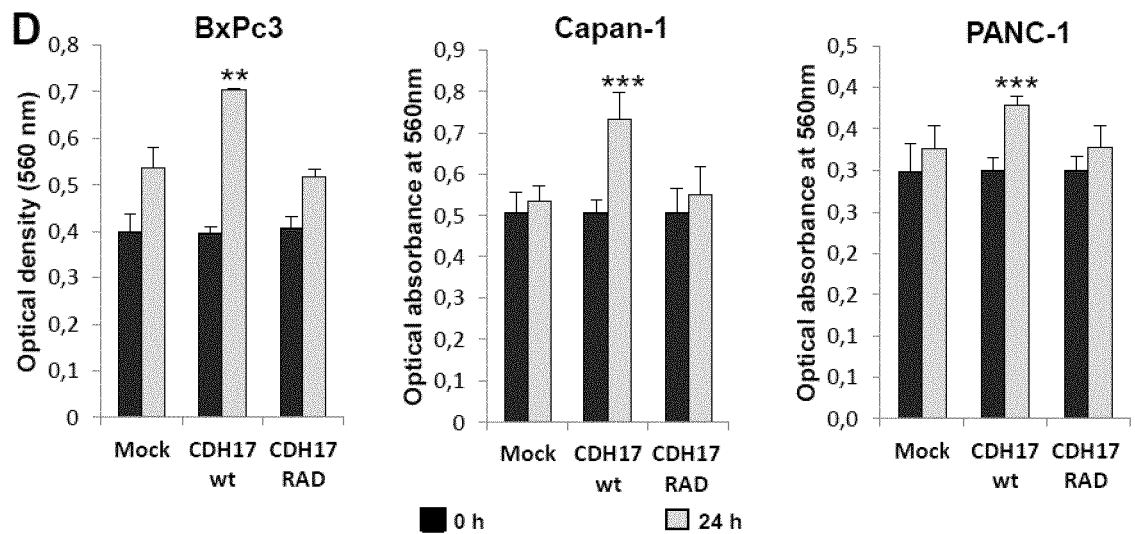

CDH17 overexpression had been reported in some pancreatic tumours. Here, in a sample set of 48 patients of pancreatic cancer, we detected CDH17 expression in 60.4% of tumours by immunohistochemistry. Among CDH17-positive tumours, a 62.1% showed intense staining, indicating overexpression of CDH17 (FIG. 7A). To learn if our findings could be extended to pancreatic cancer, we used BxPC3, PANC-1 and CAPAN pancreatic cancer cell lines. PANC-1 and CAPAN cells showed expression of CDH17, but BxPC3 did not (FIG. 7B). After transfection with CDH17-wt and CDH17-RAD mutant vectors, we observed clear differences in adhesion capacity. Where the CDH17-wt caused a clear increase in the three cell lines, the RAD mutant failed to increase adhesion above basal levels (FIG. 7C). Moreover, cell proliferation increased in CDH17-RGD transfectants, but not in cells transfected with CDH17-RAD (FIG. 7D). These results support an extension of our findings to other cancers expressing CDH17, like pancreatic cancer.

Discussion of Examples 1 to 6

We have found that the human 7D-cadherin, CDH17, contains an RGD site with capacity to act as a new ligand for integrin binding. This conclusion was obtained from the following observations: i) interaction of CDH17 with α2β1 integrin required the presence of the RGD binding site, ii) the capacity of the RGD motif to specifically bind α2β1 integrin in colon cancer cells was supported by different binding and cell adhesion assays including siRNA experiments, iii) CDH17-RGD ectodomain was able to bind colon cancer cells and activate β1 integrin when added exogenously and iv) after in vivo inoculation, tumour cells expressing mutant CDH17 RAD showed a considerable delay in tumour growth and liver colonization. In summary, RGD works as a switch that regulates the integrin activation in colon cancer metastatic cells.

Figure 8:
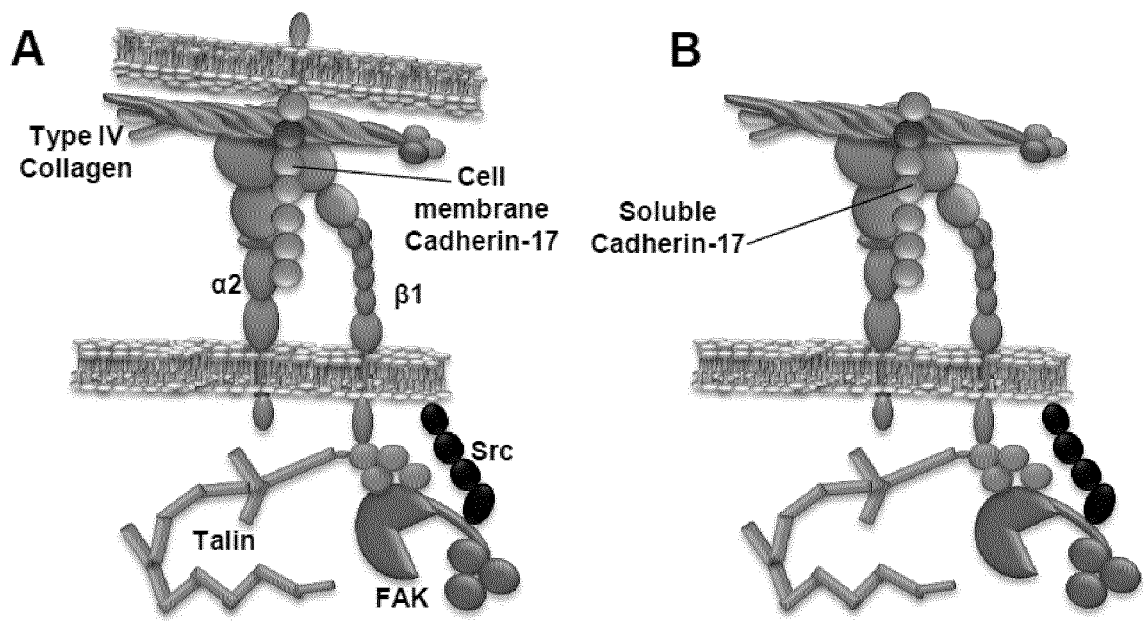
FIG. 8. Proposed models for the interaction between CDH17 and α2β1 integrin. (A, B) Either CDH17 of a contiguous cell (A) or soluble CDH17 ectodomain (B) can modulate the binding of α2β1 integrin to collagen type IV. (C) 24 h-conditioned medium from KM12SM was collected, concentrated, resolved by SDS-PAGE, and "in gel" digested with trypsin. Mass spectra were acquired on an LTQ-Orbitrap Velos mass spectrometer and the files were searched against the SwissProt database using MASCOT search engine. Peptides assigned to CDH17 are marked in red in the sequence of CDH17 (right). All detected peptides belong to the ectodomain (domains 1 to 7) of CDH17 (left). 32% of the ectodomain was detected by the proteomic analysis.
Figure 8:
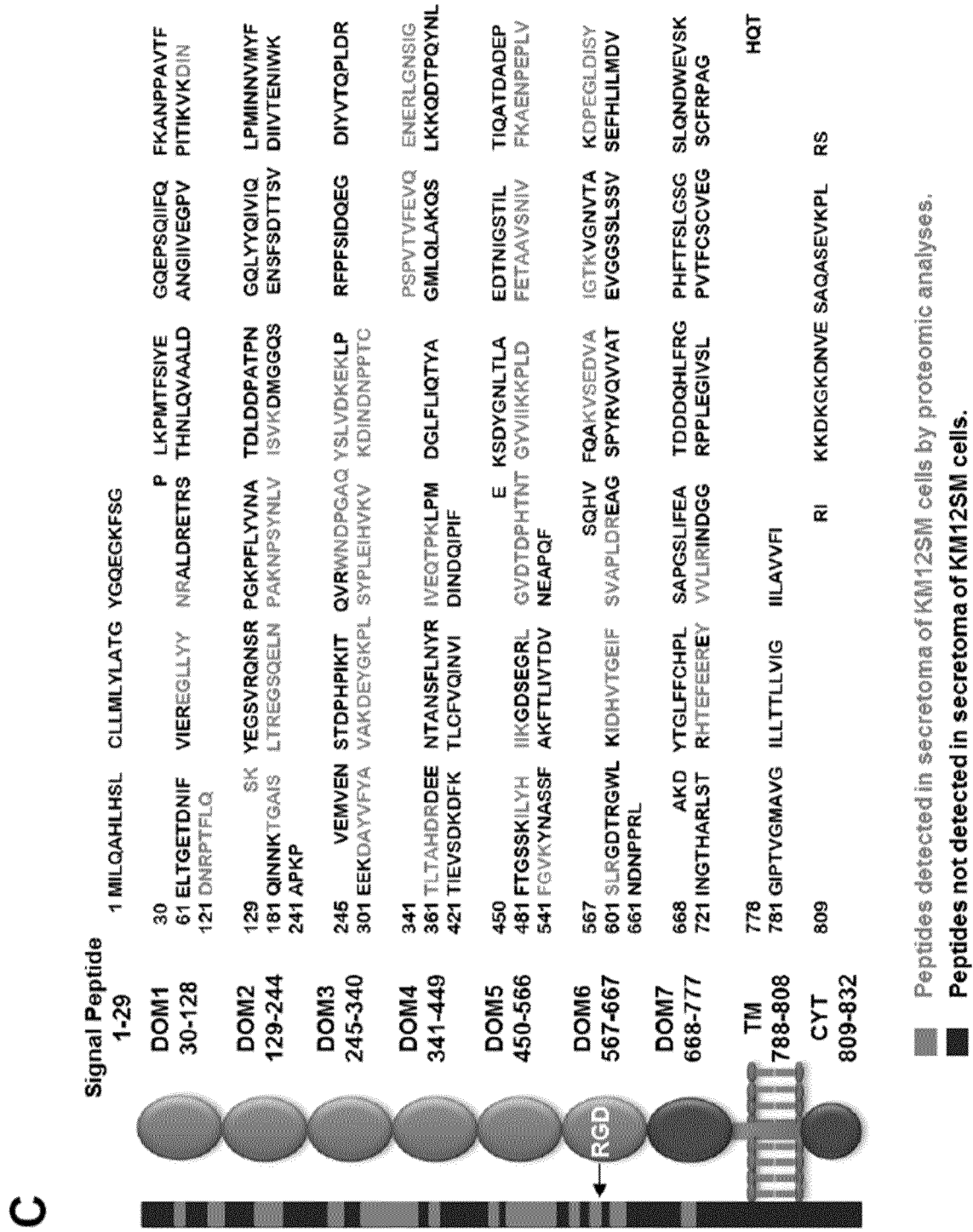

Another relevant question is whether the cadherin/integrin interaction takes place in "cis" or "trans". The "trans" model would require the presence of CDH17 in the surface of a contiguous cell (FIG. 8A) or the presence of soluble ectodomains of CDH17 (FIG. 8B) in order to facilitate the contact in the interface of α2 and β1 subunits, which is the ligand recognition site. Our data suggest that an interaction in "trans" is more probable, as incubation with soluble recombinant ectodomain followed by integrin activation would mimic the interaction with the soluble form of CDH17 after shedding of this molecule from the cell surface membrane. Furthermore, the co-culture of cells expressing only CDH17 with cells expressing only α2 integrin reflects a "trans" interaction between two cells. Still, an interaction in "cis" cannot be totally ruled out.

Other cadherins, like CDH5 (which contains two RGD motifs), CDH6 or CDH20, also contain RGD-binding sites and they could play important roles in cancer metastasis in other cancer types, where they are overexpressed. Here, we provide evidence that CDH5 RGD, but not CDH16, also activates α2β1 integrin. So, the flanking sequences of the cadherin RGD motif strongly influence the binding capacity to integrins and confer specificity to the interaction. In agreement with this hypothesis, recent studies point out a role for these cadherins in cancer and vascular damage. CDH5 and CDH6 seem to promote cancer progression, thrombus formation and vascular injury due to the induction of platelet aggregation, respectively. Some studies have reported an up-regulation of CDH5 in invasive human breast tumors and in a breast cancer model and CDH5 induction was responsible for vasculogenic mimicry in aggressive melanomas. In platelets, a previous study revealed a role for CDH6 as a novel ligand for allbβ3 integrin, being this binding responsible for platelet aggregation and thrombus formation. This interaction might play a role in the signs of thrombosis occurring in patients at metastatic stage and the contribution of platelets to tumor metastasis. Further experiments are required to clarify the integrin-binding capacity as a general mechanism of RGD-containing cadherins for the promotion of metastasis.

CDH17, as other cadherins, is a target for ectodomain shedding due to the presence of elevated protease activity in the tumor microenvironment. Previous observations confirmed the shedding of CDH17 in the conditioned medium of KM12SM cells. The secreted soluble form of CDH17 contained the RGD domain. This "shedding" in metastatic cells makes CDH17 a candidate biomarker for detection in biofluids (serum or plasma) of colon cancer patients. Then, CDH17 could be useful for patient stratification and targeted therapy.

Example 7

Figure 9:
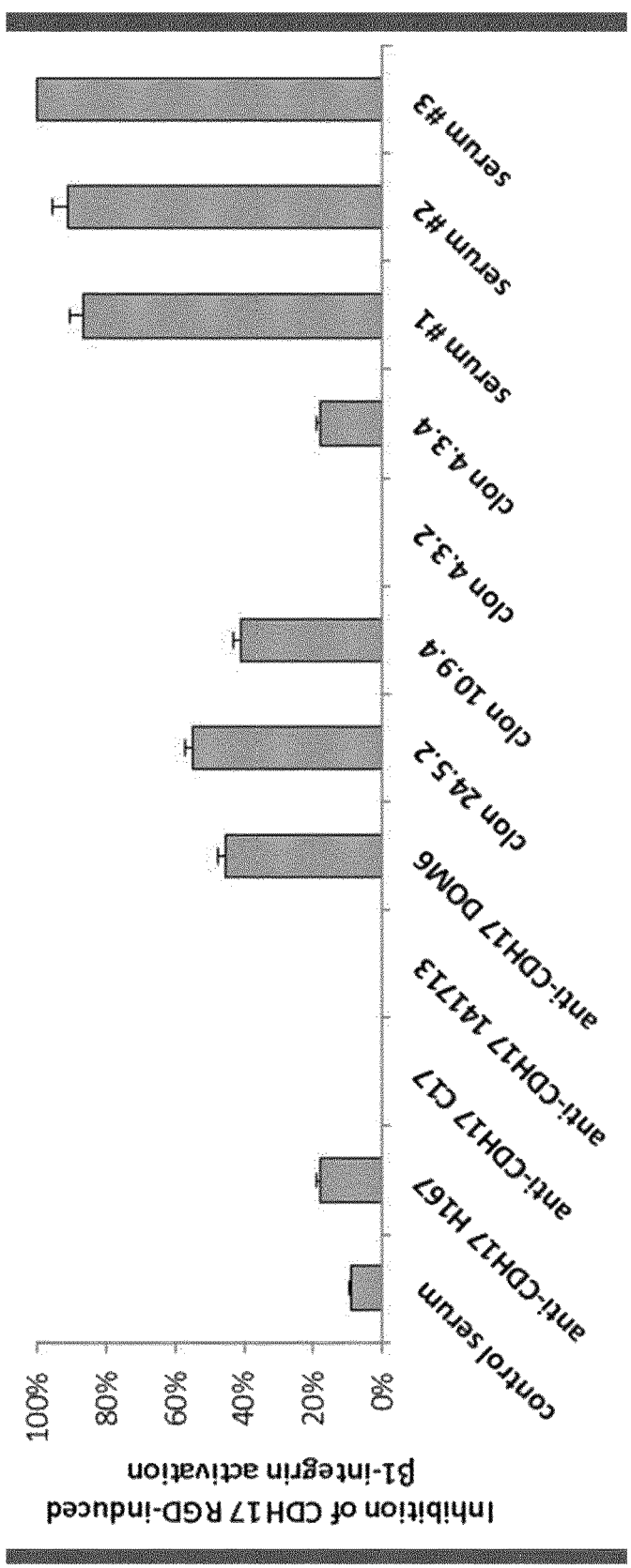
FIG. 9. Testing different antibodies for their capacity to inhibit β1 integrin activation. Inhibition of CDH17 RGD peptide-induced β1 integrin activation by different antibodies (commercial antibodies against CDH17 domain 6, supernatants from monoclonal antibodies against CDH17 RGD peptides and serum against RGD peptide) was tested in RKO cells.
Figure 10:
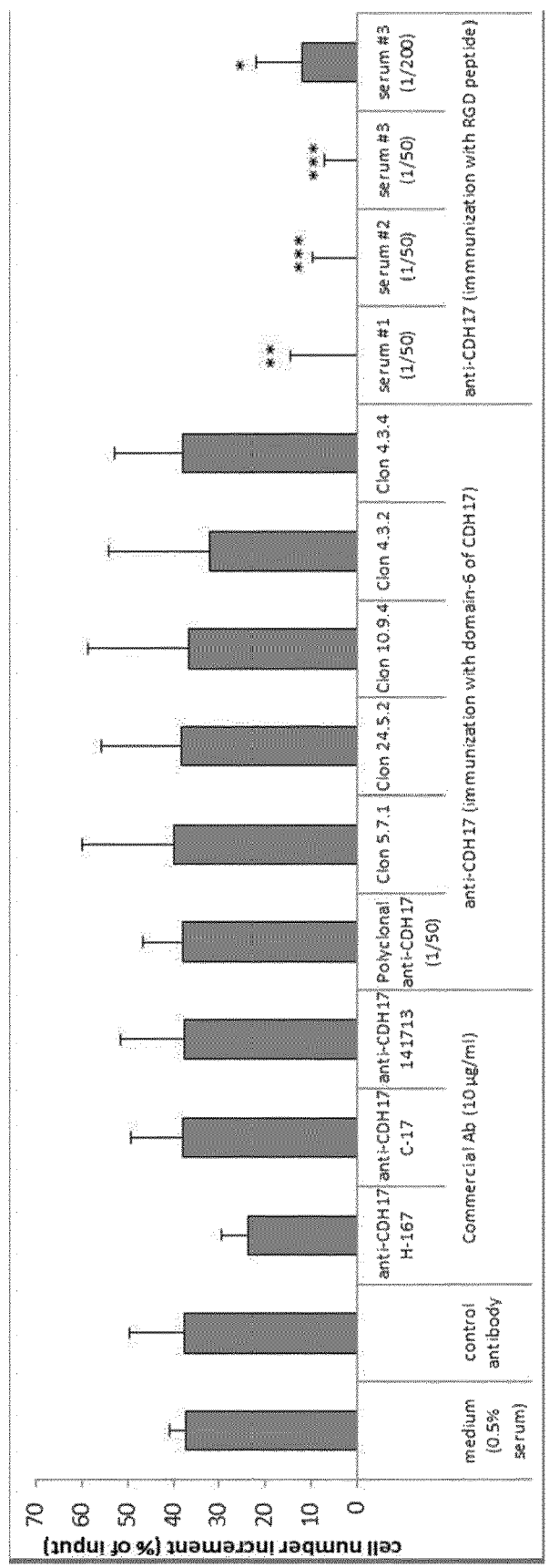
FIG. 10. Same antibodies as FIG. 10 were tested for their capacity to arrest cell proliferation. Cell growth inhibition by different antibodies (commercial, antibodies against CDH17 domain 6, supernatants from monoclonal antibodies against CDH17 domain 6 and serum against RGD peptide) was tested in KM12SM cells.

Effect of the CDH17 Sequence Used for Immunization in the Inhibition Capacity of β1 Integrin Activation We tested different antibodies for its capacity to inhibit in β1 integrin activation. Commercial antibodies (H167, C-17 or 141713) against the whole extracellular domains or the C-peptide domain of CDH17 were unable to carry out any inhibition of in β1 integrin activation (FIG. 9). Moreover, when we tested either polyclonal or monoclonal antibodies against domain 6 of the CDH17, these antibodies were able to inhibit β1 integrin activation only at a very limited extent (<50%). The increment in β1 integrin activation status leads to an increment in cell proliferation in colon cancer cells (Bartolomé et al. 2014, Oncogene 33:1658-1669). To test if the antibodies generated against Cadherin-17 RGD motif could inhibit cell proliferation, we subjected colon cancer cells to cell proliferation assays in the presence or absence of these antibodies. As expected, the antibodies were able to inhibit cell proliferation, indicating that the blocking of RGD motif in Cadherin-17 leads to an impaired cell proliferation. These commercial antibodies or antibodies against domain 6 of CDH17 did not have either any significant effect on cell proliferation or adhesion (FIG. 10).

However, polyclonal sera (#1, 2, 3) from mice immunized with peptide VSLRGDTRG (SEQ ID NO: 1) did inhibit β1 integrin activation near 100%. Mouse serum #3 completely inhibited peptide-induced activation of CDH17. Sera 1 and 2 also produced an almost complete inhibition (FIG. 9). This inhibition implies arrest of cell proliferation. In this regard, these polyclonal sera caused a complete inhibition of proliferation when tested in a MTT assay at 1:50 dilution, and almost complete at 1:200 dilution in the case of serum #3 (FIG. 10). These results are telling us that only a highly focused immune response against a purified peptide containing the CDH17 RGD motif is able to induce effective antibodies for a blocking immune response.

Example 8

Figure 11:
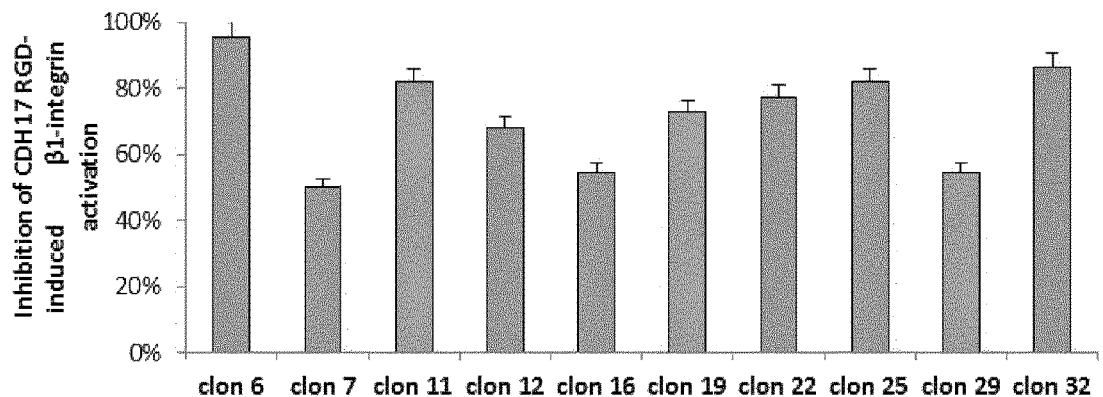
FIG. 11. Initial testing of different hybridoma clones anti RGD peptide for their capacity to inhibit in β1 integrin activation induced by CDH17 RGD peptide in RKO cells.
Figure 12:
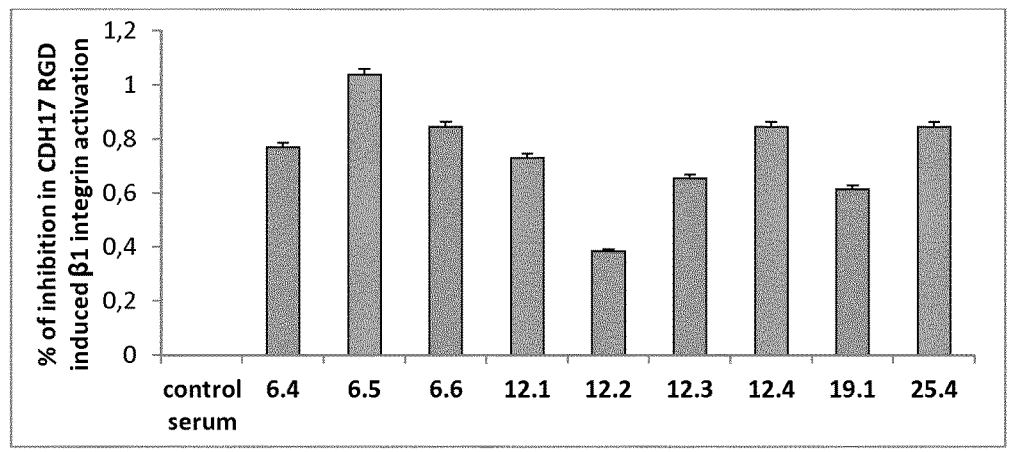
FIG. 12. Second testing of different hybridoma clones anti RGD peptide for their capacity to inhibit in β1 integrin activation induced by CDH17 RGD peptide in RKO cells.

Development of Monoclonal Antibodies with the Inhibition Capacity of β1 Integrin Activation Mouse #3 was selected for hybridoma development. An initial testing was carried out with hybridoma supernatants obtained after cell fusion producing CDH17 antibodies (FIG. 11). Clone #6 was able to inhibit near 100% β1 integrin activation. This clone together with clones 12, 19 and 25 were selected for further selection and isolation of monoclonal antibodies. A second test was carried out with these clones after first cloning step (FIG. 12). Clones 6.5, 6.6, 12.4 and 25.4 were selected for final cloning.

Figure 13:
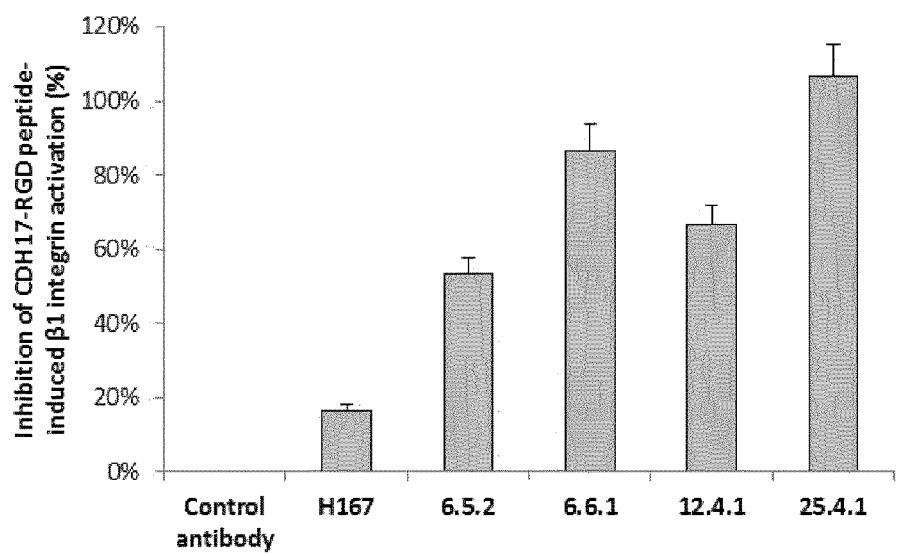
FIG. 13. Final testing of purified monoclonal antibodies on β1 integrin activation. Mab 25.4.1 showed the capacity to inhibit completely (100%) the activation of the β1 integrin, followed by 6.6.1 (90%), 12.4.1 (70%) and 6.5.2 (<60%).

After second cloning step by limiting dilution, clones 6.5.1, 6.5.2, 6.6.1, 6.6.2, 12.4.1 and 25.4.1 were selected for final characterization (Table 1). Hybridoma cells were grown according to standard procedures in RPMI-1640 with L-glutamine and sodium bicarbonate media, supplemented with 10% Foetal Bovine Serum and antibiotics. Culture supernatans were collected and monoclonal antibodies (mAbs) were purified by Protein G and dialyzed against PBS for further use. The mAbs were tested for their effect on β1 integrin activation, cell proliferation and cell adhesion. The mAb 25.4.1 showed the capacity to inhibit completely (100%) the activation of the β1 integrin, followed by 6.6.1 (90%), 12.4.1 (70%) and 6.5.2 (<60%) (FIG. 13).

Figure 14:
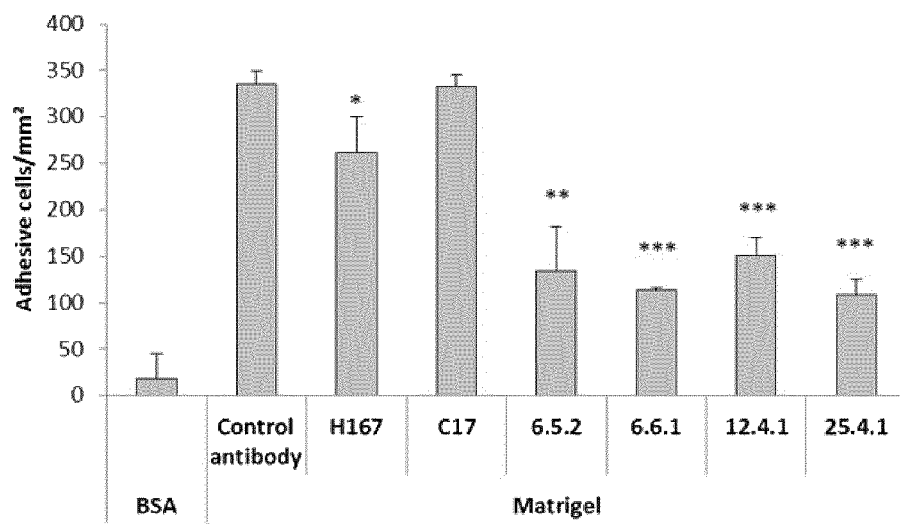
FIG. 14. Final testing of purified monoclonal antibodies on cell adhesion. Results obtained with the mAbs on cell adhesion followed the same order, but inverse, to the activation of the β1 integrin. Mab 25.4.1 provoked the major inhibition on cell adhesion, followed by the other three mAbs in the same order.

When analysing the cell adhesion, as expected, the results obtained with mAbs followed the same order, but inverse, to the activation of the β1 integrin. Mab 25.4.1 provoked the major inhibition on cell adhesion, followed by the other three mAbs in the same order. They were much more effective than commercial anti-CDH17 antibodies and control antibody (FIG. 14).

Figure 15:
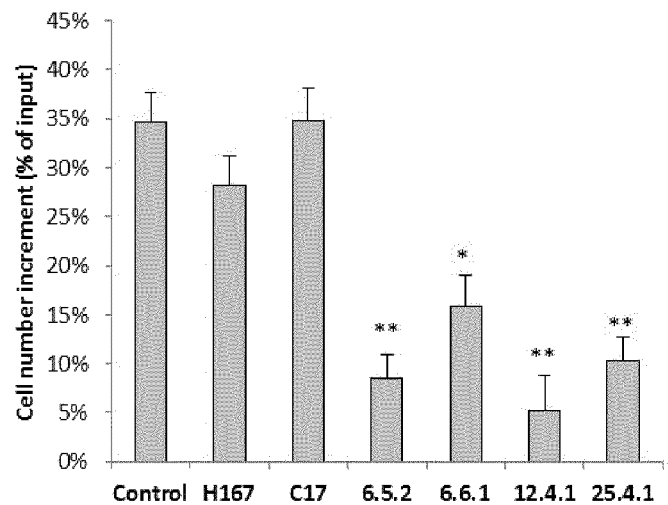
FIG. 15. Final testing of purified monoclonal antibodies on cell proliferation. Mab 12.4.1 was the most effective in decreasing cell proliferation, followed by 6.5.2, 25.4.1 and 6.6.1.

Regarding cell proliferation, mAb 12.4.1 was the most effective in decreasing cell proliferation, followed by 6.5.2, 25.4.1 and 6.6.1 (FIG. 15).

In summary, 25.4.1 seems to be particularly useful for inhibition of the β1 integrin activation and the cell adhesion. In contrast, 12.4.1 seems particularly useful for blocking cell proliferation.

TABLE 1

Summary of results obtained with the anti-RGD CDH17 peptide mAbs.

| Mab | Isotype | ELISA indirect vs CDH17 (E. coli) DO492nm | ELISA indirect vs BSA-peptide | Flow cytometry KM12SM | B1 inhibition RKO |
|---|---|---|---|---|---|
| PA383-6.5.1 | IgG1 kappa | 1.3 | 0.65 | 14% | 72% |
| PA383-6.5.2 | IgG1 kappa | 1.05 | 0.68 | 14% | 106% |
| PA383-6.6.1 | IgG1 kappa | 1.5 | 0.48 | 14% | 50% |
| PA383-6.6.2 | IgG1 kappa | 1.2 | 0.49 | 14% | 69% |
| PA383-12.4.1 | IgG1-2a/Kappa-Lambda | 0.45 | 0.49 | 6% | 78% |
| PA383-25.4.1 (DSM ACC3266) | Non reactive to IsoQuick ™kit | 0.3 | 0.19 | 19% | 92% |

Example 9

Sequencing and CDRs Identification

The complementarity (or specificity)-determining regions (CDRs) from the mouse-derived hybridomas were identified for clones PA383-12.4.1, PA383-6.6.1 and PA383-6.5.2 following the set of rules of Kabat and Chothia numbering schemes. Resulting sequences are as follow:

| $V_L$ - CDRs hybridoma PA383-12.4.1: | | |
|---|---|---|
| CDR-L1 | CDR-L2 | CDR-L3 |
| RASENIYSYLA (SEQ ID NO: 8) | NAKTLAE (SEQ ID NO: 9) | QHHYGTPT (SEQ ID NO: 10) |

| $V_H$ - CDRs hybridoma PA383-12.4.1: | | |
|---|---|---|
| CDR-H1 | CDR-H2 | CDR-H3 |
| GYTFTNYWMH (SEQ ID NO: 2) | EINPSNGRTNYNEKFKS (SEQ ID NO: 3) | GSYGNYLPFAY (SEQ ID NO: 4) |

| $V_L$ - CDRs hybridomas PA383-6.6.1 and PA383-6.5.2: | | |
|---|---|---|
| CDR-L1 | CDR-L2 | CDR-L3 |
| KASQSVSNDVA (SEQ ID NO: 11) | YTSNRST (SEQ ID NO: 12) | QQDYSSPLT (SEQ ID NO: 13) |

| $V_H$ - CDRs hybridomas PA383-6.6.1 and PA383-6.5.2: | | |
|---|---|---|
| CDR-H1 | CDR-H2 | CDR-H3 |
| GYSFTGYSMN (SEQ ID NO: 5) | LINPYNGGTSYNQKFKG (SEQ ID NO: 6) | KALRRDWLAMDY (SEQ ID NO: 7) |

Since the amplification of VH and VL from hybridoma PA383-25.4.1 was not possible, this cell culture was deposited with reference PA383-25.4.1 under Accession number DSM ACC3266 on 9 Apr. 2015 at the Leibniz Institut DSMZ—Deutsche Sammlung von Mikroorganismen and Zellkulturen GmbH for the purpose of patent procedure according to the Budapest Treaty on the International Recognition of the Deposit of Microorganisms.

Example 10

Cadherin RGD Motifs (Except from CDH16) Promoted (β1-Integrin Activation

Figure 16:
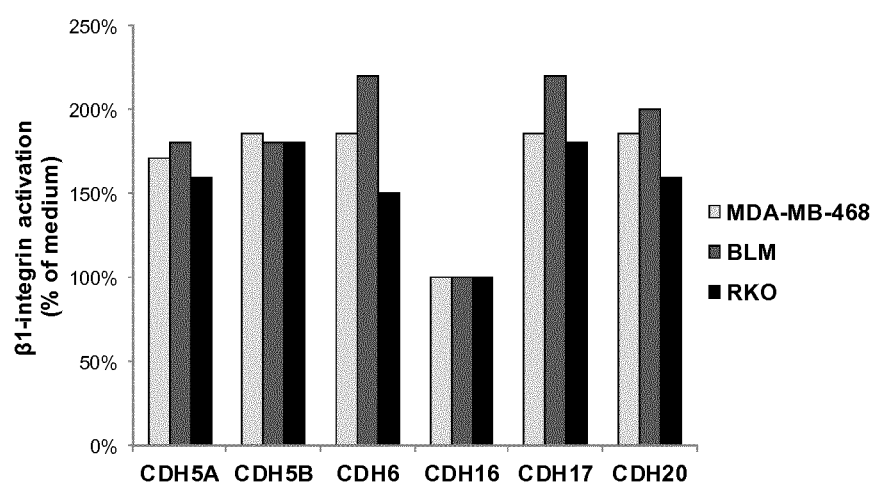
FIG. 16. Cadherin RGD motifs (except from CDH16) promoted β1-integrin activation.

Treatment with 9 aa peptides containing the RGD motif and the flanking sequences of cadherin 5 (SEQ ID NO: 37 for the RGD motif of domain 2 (CDH5A), and SEQ ID: 19 for the RGD motif of domain 3 (CDH5B), cadherin 6 (SEQ ID NO: 38), cadherin 17 (SEQ ID NO: 1) and cadherin 20 (SEQ ID NO: 39), but not cadherin 16 (SEQ ID NO: 31, RAIRGDTEG), induced the conformational change of β1-integrin into a high affinity conformation, detected by Huts21 β1-antibody in a flow cytometer in MDA-MB-468 (a breast cancer cell line), BLM (a melanoma cell line), and RKO (a colon cancer cell line) cells (FIG. 16).

Example 11

Figure 17:
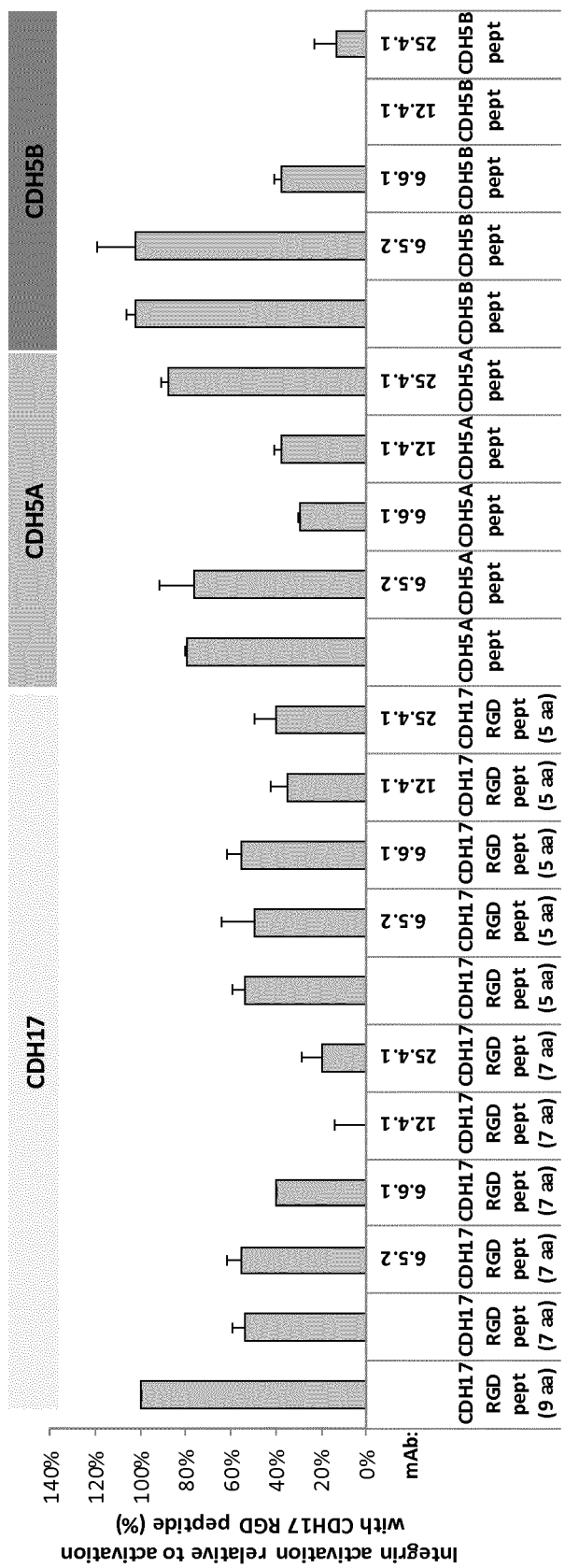
FIG. 17. Monoclonal antibodies against CDH17 RGD motif inhibited β1-integrin activation induced by CDH5 RGD peptides and by shorter CDH17 RGD peptides.

Monoclonal Antibodies Against CDH17 RGD Motif Inhibited β1-Integrin Activation Induced by CDH5 RGD Peptides and by Shorter CDH17 RGD Peptides RKO colon cancer cells were treated with the 9 aa RGD peptides of CDH17 (SEQ ID NO: 1), CDH5A (SEQ ID NO: 37) or CDH5B (SEQ ID NO: 19), or shorter forms of CDH17 RGD peptides of only 7 aa or 5 aa and simultaneously with the indicated antibodies, and subjected to flow cytometry assays as before. Data were shown in relation to integrin activation induced by 9 aa CDH17 RGD peptide (SEQ ID NO: 1) (taken as 100%), 7 aa peptide: SLRGDTR (SEQ ID NO: 32), 5 aa peptide: LRGDT (SEQ ID NO: 14) (FIG. 17). These data demonstrate i) that 7 and 5 aa peptides from CDH17 are able to induce efficiently the integrin activation, ii) 12.4.1 and 25.4.1 mAbs are more effective blocking these short peptides, iii) peptides containing both RGDs from CDH5 are able to activate beta1 integrin and iv) 12.4.1 and 25.4.1 are effective with region B (domain 3) and 6.6.1 with region A (domain 2). This result confirms the usefulness of anti-CDH17 mAbs against other cadherins.

Example 12

Expression of CDH5 in Melanoma and Breast Cancer Cell Lines

Figure 18:
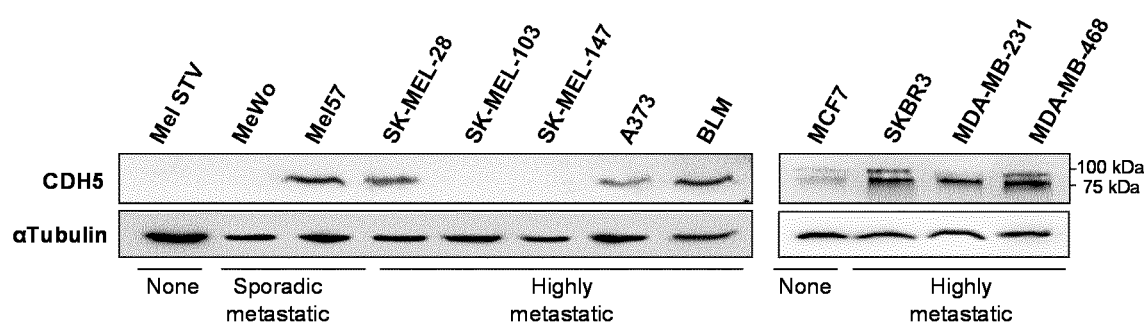
FIG. 18. Expression of CDH5 in melanoma and breast cancer cell lines.

Various melanoma and breast cancer cells lines known to be classified as sporadic metastatic or highly metastatic were analysed in order to determine their expression of CDH5. Results shown in FIG. 18 reflect that 4 out of 7 melanoma cell lines and all the breast cancer cells lines tested were positive for CDH5 expression.

Deposit of Biological Material According to the Budapest Treaty

Hybridoma PA383-25.4.1 was deposited with reference PA383-25.4.1 on 9 Apr. 2015 at the Leibniz Institut DSMZ Deutsche Sammlung von Mikroorganismen and Zellkulturen GmbH for the purpose of patent procedure according to the Budapest Treaty on the International Recognition of the Deposit of Microorganisms. All restrictions on the accessibility of the deposit will be irrevocably withdrawn by the applicant upon the granting of a patent, and the deposit will be replaced if viable samples cannot be dispensed by the depository.

The invention claimed is:

1. An agent binding specifically to an epitope comprising residues 603 to 605 of human cadherin 17 (CDH17), and/or to an epitope comprising residues 236 to 238 or residues 299 to 301 of human cadherin 5 (CDH5), and/or to an epitope comprising residues 83 to 85 of human cadherin 6 (CDH6) and/or to an epitope comprising residues 89 to 91 of human cadherin 20 (CDH20), wherein said agent is an antibody or an antigen-binding fragment of said antibody selected from the group consisting of:
   (i) an antibody or an antigen-binding fragment comprising, within the heavy chain:
      a CDR comprising the amino acid sequence shown in SEQ ID NO: 2 [CDR-H1], a CDR comprising the amino acid sequence shown in SEQ ID NO: 3 [CDR-H2], and a CDR comprising the amino acid sequence shown in SEQ ID NO: 4 [CDR-H3],
   or
      a CDR comprising the amino acid sequence shown in SEQ ID NO: 5 [CDR-H1], a CDR comprising the amino acid sequence shown in SEQ ID NO: 6 [CDR-H2], and a CDR comprising the amino acid sequence shown in SEQ ID NO: 7 [CDR-H3],
   and
   (ii) an antibody produced by the hybridoma cell line with reference PA383-25.4.1, deposited under Accession number DSM ACC3266 of 9 Apr. 2015 at the Deutsche Sammlung von Mikroorganismen and Zellkulturen GmbH.

2. The agent according to claim 1, wherein the epitope comprises the sequence shown in SEQ ID NO: 1 (VSL-RGDTRG).

3. The agent according to claim 1, wherein said antigen-binding fragment is selected from the group consisting of Fv, Fab, F(ab')₂, and Fab'.

4. The agent according to claim 1, wherein said antibody or the said antigen-binding fragment comprises
   within the heavy chain, a CDR-H1 comprising the amino acid sequence shown in SEQ ID NO: 2, a CDR-H2 comprising the amino acid sequence shown in SEQ ID NO: 3, and a CDR-H3 comprising the amino acid sequence shown in SEQ ID NO: 4, and within the light chain, a CDR-L1 comprising the amino acid sequence shown in SEQ ID NO: 8, a CDR-L2 comprising the amino acid sequence shown in SEQ ID NO: 9, and a CDR-L3 comprising the amino acid sequence shown in SEQ ID NO: 10, or
   within the heavy chain, a CDR comprising the amino acid sequence shown in SEQ ID NO: 5 [CDR-H1], a CDR comprising the amino acid sequence shown in SEQ ID NO: 6 [CDR-H2], and a CDR comprising the amino acid sequence shown in SEQ ID NO: 7 [CDR-H3], and within the light chain, a CDR-L1 comprising the amino acid sequence shown in SEQ ID NO: 11, a CDR-L2 comprising the amino acid sequence shown in SEQ ID NO: 12, and a CDR-L3 comprising the amino acid sequence shown in SEQ ID NO: 13.

5. The agent according to claim 1, wherein said antibody or said antigen-binding fragment is humanised.

6. The agent according to claim 1, wherein said antibody or antigen-binding fragment is an immunoglobulin new antigen receptor (IgNAR) or a camelid antibody.

7. An antibody construct comprising the antigen-binding fragment according to claim 1, wherein the antibody construct is selected from the group consisting of scFv, scFv-Fc, minibody, (scFv)₂ and diabody.

8. The hybridoma cell line with reference PA383-25.4.1, deposited under Accession number DSM ACC3266 on 9 Apr. 2015 at the Deutsche Sammlung von Mikroorganismen and Zellkulturen GmbH.

9. A pharmaceutical composition comprising a therapeutically effective amount of the agent according to claim 1 together with a pharmaceutically acceptable excipient or carrier.

* * * * *

```
                       SEQUENCE LISTING

<160> NUMBER OF SEQ ID NOS: 39

<210> SEQ ID NO 1
<211> LENGTH: 9
<212> TYPE: PRT
<213> ORGANISM: Homo sapiens

<400> SEQUENCE: 1

Val Ser Leu Arg Gly Asp Thr Arg Gly
1               5

<210> SEQ ID NO 2
<211> LENGTH: 10
<212> TYPE: PRT
<213> ORGANISM: Artificial Sequence
<220> FEATURE:
<223> OTHER INFORMATION: CDR-H1

<400> SEQUENCE: 2

Gly Tyr Thr Phe Thr Asn Tyr Trp Met His
1               5                   10

<210> SEQ ID NO 3
<211> LENGTH: 17
<212> TYPE: PRT
<213> ORGANISM: Artificial Sequence
<220> FEATURE:
<223> OTHER INFORMATION: CDR-H3

<400> SEQUENCE: 3

Glu Ile Asn Pro Ser Asn Gly Arg Thr Asn Tyr Asn Glu Lys Phe Lys
1               5                   10                  15

Ser

<210> SEQ ID NO 4
<211> LENGTH: 11
<212> TYPE: PRT
<213> ORGANISM: Artificial Sequence
<220> FEATURE:
<223> OTHER INFORMATION: CDR-H3

<400> SEQUENCE: 4

Gly Ser Tyr Gly Asn Tyr Leu Pro Phe Ala Tyr
1               5                   10

<210> SEQ ID NO 5
<211> LENGTH: 10
<212> TYPE: PRT
<213> ORGANISM: Artificial Sequence
<220> FEATURE:
<223> OTHER INFORMATION: CDR-H1

<400> SEQUENCE: 5
```

```
Gly Tyr Ser Phe Thr Gly Tyr Ser Met Asn
1               5                   10

<210> SEQ ID NO 6
<211> LENGTH: 17
<212> TYPE: PRT
<213> ORGANISM: Artificial Sequence
<220> FEATURE:
<223> OTHER INFORMATION: CDR-H2

<400> SEQUENCE: 6

Leu Ile Asn Pro Tyr Asn Gly Gly Thr Ser Tyr Asn Gln Lys Phe Lys
1               5                   10                  15

Gly

<210> SEQ ID NO 7
<211> LENGTH: 12
<212> TYPE: PRT
<213> ORGANISM: Artificial Sequence
<220> FEATURE:
<223> OTHER INFORMATION: CDR-H3

<400> SEQUENCE: 7

Lys Ala Leu Arg Arg Asp Trp Leu Ala Met Asp Tyr
1               5                   10

<210> SEQ ID NO 8
<211> LENGTH: 11
<212> TYPE: PRT
<213> ORGANISM: Artificial Sequence
<220> FEATURE:
<223> OTHER INFORMATION: CDR-L1

<400> SEQUENCE: 8

Arg Ala Ser Glu Asn Ile Tyr Ser Tyr Leu Ala
1               5                   10

<210> SEQ ID NO 9
<211> LENGTH: 7
<212> TYPE: PRT
<213> ORGANISM: Artificial Sequence
<220> FEATURE:
<223> OTHER INFORMATION: CDR-L2

<400> SEQUENCE: 9

Asn Ala Lys Thr Leu Ala Glu
1               5

<210> SEQ ID NO 10
<211> LENGTH: 8
<212> TYPE: PRT
<213> ORGANISM: Artificial Sequence
<220> FEATURE:
<223> OTHER INFORMATION: CDR-L3

<400> SEQUENCE: 10

Gln His His Tyr Gly Thr Pro Thr
1               5

<210> SEQ ID NO 11
<211> LENGTH: 11
<212> TYPE: PRT
<213> ORGANISM: Artificial Sequence
<220> FEATURE:
<223> OTHER INFORMATION: CDR-L1
```

-continued

<400> SEQUENCE: 11

Lys Ala Ser Gln Ser Val Ser Asn Asp Val Ala
1               5                   10

<210> SEQ ID NO 12
<211> LENGTH: 7
<212> TYPE: PRT
<213> ORGANISM: Artificial Sequence
<220> FEATURE:
<223> OTHER INFORMATION: CDR-L2

<400> SEQUENCE: 12

Tyr Thr Ser Asn Arg Ser Thr
1               5

<210> SEQ ID NO 13
<211> LENGTH: 9
<212> TYPE: PRT
<213> ORGANISM: Artificial Sequence
<220> FEATURE:
<223> OTHER INFORMATION: CDR-L3

<400> SEQUENCE: 13

Gln Gln Asp Tyr Ser Ser Pro Leu Thr
1               5

<210> SEQ ID NO 14
<211> LENGTH: 5
<212> TYPE: PRT
<213> ORGANISM: Homo sapiens

<400> SEQUENCE: 14

Leu Arg Gly Asp Thr
1               5

<210> SEQ ID NO 15
<211> LENGTH: 5
<212> TYPE: PRT
<213> ORGANISM: Homo sapiens

<400> SEQUENCE: 15

Leu Arg Gly Asp Ser
1               5

<210> SEQ ID NO 16
<211> LENGTH: 5
<212> TYPE: PRT
<213> ORGANISM: Homo sapiens

<400> SEQUENCE: 16

Leu Arg Gly Asp Tyr
1               5

<210> SEQ ID NO 17
<211> LENGTH: 5
<212> TYPE: PRT
<213> ORGANISM: Homo sapiens

<400> SEQUENCE: 17

Asp Arg Gly Asp Gly
1               5

<210> SEQ ID NO 18
<211> LENGTH: 4
<212> TYPE: PRT

```
<213> ORGANISM: Artificial Sequence
<220> FEATURE:
<223> OTHER INFORMATION: Synthetic peptide

<400> SEQUENCE: 18

Arg Ala Asp Ser
1

<210> SEQ ID NO 19
<211> LENGTH: 9
<212> TYPE: PRT
<213> ORGANISM: Homo sapiens

<400> SEQUENCE: 19

Ser Ile Leu Arg Gly Asp Tyr Gln Asp
1               5

<210> SEQ ID NO 20
<211> LENGTH: 10
<212> TYPE: PRT
<213> ORGANISM: Homo sapiens

<400> SEQUENCE: 20

Arg Ala Ile Arg Arg Gly Asp Thr Glu Gly
1               5                   10

<210> SEQ ID NO 21
<211> LENGTH: 35
<212> TYPE: DNA
<213> ORGANISM: Artificial Sequence
<220> FEATURE:
<223> OTHER INFORMATION: RT-PCR primer to amplify CDH17

<400> SEQUENCE: 21
agctcgagga tctgagttga tcaatctgct tagtg                              35

<210> SEQ ID NO 22
<211> LENGTH: 30
<212> TYPE: DNA
<213> ORGANISM: Artificial Sequence
<220> FEATURE:
<223> OTHER INFORMATION: RT-PCR primer to amplify CDH17

<400> SEQUENCE: 22
cgggtaccat gagatggttg ttgctgaaat                                    30

<210> SEQ ID NO 23
<211> LENGTH: 40
<212> TYPE: DNA
<213> ORGANISM: Artificial Sequence
<220> FEATURE:
<223> OTHER INFORMATION: Mutagenesis primer

<400> SEQUENCE: 23
ggacataagc tattcactga gggcagacac aagaggttgg                         40

<210> SEQ ID NO 24
<211> LENGTH: 40
<212> TYPE: DNA
<213> ORGANISM: Artificial Sequence
<220> FEATURE:
<223> OTHER INFORMATION: Mutagenesis primer

<400> SEQUENCE: 24
ccaacctctt gtgtctgccc tcagtgaata gcttatgtcc                         40
```

<210> SEQ ID NO 25
<211> LENGTH: 20
<212> TYPE: DNA
<213> ORGANISM: Artificial Sequence
<220> FEATURE:
<223> OTHER INFORMATION: CDH6 amplification primer

<400> SEQUENCE: 25
gtcatcaccg accaggaaac                                          20

<210> SEQ ID NO 26
<211> LENGTH: 20
<212> TYPE: DNA
<213> ORGANISM: Artificial Sequence
<220> FEATURE:
<223> OTHER INFORMATION: CDH6 amplification primer

<400> SEQUENCE: 26
tgcagggtct gaatcaactg                                          20

<210> SEQ ID NO 27
<211> LENGTH: 19
<212> TYPE: DNA
<213> ORGANISM: Artificial Sequence
<220> FEATURE:
<223> OTHER INFORMATION: CDH20 amplification primer

<400> SEQUENCE: 27
agaggagctg ggtttggaa                                           19

<210> SEQ ID NO 28
<211> LENGTH: 20
<212> TYPE: DNA
<213> ORGANISM: Artificial Sequence
<220> FEATURE:
<223> OTHER INFORMATION: CDH20 amplification primer

<400> SEQUENCE: 28
gcatctgtgg ctgtcacttg                                          20

<210> SEQ ID NO 29
<211> LENGTH: 4
<212> TYPE: PRT
<213> ORGANISM: Artificial Sequence
<220> FEATURE:
<223> OTHER INFORMATION: Artificial peptide

<400> SEQUENCE: 29

Arg Gly Asp Ser
1

<210> SEQ ID NO 30
<211> LENGTH: 4
<212> TYPE: PRT
<213> ORGANISM: Artificial Sequence
<220> FEATURE:
<223> OTHER INFORMATION: Reducing active site of Thioredoxin A

<400> SEQUENCE: 30

Cys Gly Pro Cys
1

<210> SEQ ID NO 31
<211> LENGTH: 9
<212> TYPE: PRT
<213> ORGANISM: Homo sapiens

<400> SEQUENCE: 31

Arg Ala Ile Arg Gly Asp Thr Glu Gly
1               5

<210> SEQ ID NO 32
<211> LENGTH: 7
<212> TYPE: PRT
<213> ORGANISM: Homo sapiens

<400> SEQUENCE: 32

Ser Leu Arg Gly Asp Thr Arg
1               5

<210> SEQ ID NO 33
<211> LENGTH: 7
<212> TYPE: PRT
<213> ORGANISM: Homo sapiens

<400> SEQUENCE: 33

Gly Leu Arg Gly Asp Ser Gly
1               5

<210> SEQ ID NO 34
<211> LENGTH: 7
<212> TYPE: PRT
<213> ORGANISM: Homo sapiens

<400> SEQUENCE: 34

Ile Leu Arg Gly Asp Tyr Gln
1               5

<210> SEQ ID NO 35
<211> LENGTH: 7
<212> TYPE: PRT
<213> ORGANISM: Homo sapiens

<400> SEQUENCE: 35

Gln Asp Arg Gly Asp Gly Ser
1               5

<210> SEQ ID NO 36
<211> LENGTH: 7
<212> TYPE: PRT
<213> ORGANISM: Homo sapiens

<400> SEQUENCE: 36

Met Asp Arg Gly Asp Gly Ser
1               5

<210> SEQ ID NO 37
<211> LENGTH: 9
<212> TYPE: PRT
<213> ORGANISM: Homo sapiens

<400> SEQUENCE: 37

Gln Gly Leu Arg Gly Asp Ser Gly Thr
1               5

<210> SEQ ID NO 38
<211> LENGTH: 9
<212> TYPE: PRT
<213> ORGANISM: Homo sapiens

<400> SEQUENCE: 38

```
Asp Gln Asp Arg Gly Asp Gly Ser Leu
1               5

<210> SEQ ID NO 39
<211> LENGTH: 9
<212> TYPE: PRT
<213> ORGANISM: Homo sapiens

<400> SEQUENCE: 39

Asp Met Asp Arg Gly Asp Gly Ser Ile
1               5
```